United States Patent [19]

Olson et al.

[11] Patent Number: 4,874,896

[45] Date of Patent: Oct. 17, 1989

[54] PROCESS FOR THE PRODUCTION OF ALKYLAMINES

[75] Inventors: Kurt D. Olson, Cross Lanes; Steven W. Kaiser, South Charleston, both of W. Va.

[73] Assignee: UOP, Des Plaines, Ill.

[21] Appl. No.: 137,198

[22] Filed: Dec. 23, 1987

[51] Int. Cl.$^4$ .................. C07C 85/06; B61J 27/182
[52] U.S. Cl. ..................... 564/479; 564/480; 502/214
[58] Field of Search .............. 564/479, 480; 502/214, 502/202, 210, 213

[56] References Cited

U.S. PATENT DOCUMENTS

| | | | |
|---|---|---|---|
| 4,082,805 | 4/1978 | Kaeding | 564/474 |
| 4,254,061 | 3/1981 | Weigert | 564/479 |
| 4,398,041 | 8/1983 | Cochran et al. | 564/479 |
| 4,434,300 | 2/1984 | Deeba et al. | 564/479 |
| 4,760,184 | 7/1988 | Pierantozzi | 564/409 |

FOREIGN PATENT DOCUMENTS

| | | |
|---|---|---|
| 0039918 | 11/1981 | European Pat. Off. . |
| 0064380 | 11/1982 | European Pat. Off. . |
| 0076034 | 4/1983 | European Pat. Off. . |
| 0101921 | 3/1984 | European Pat. Off. . |
| 0107457 | 5/1984 | European Pat. Off. . |
| 125616 | 11/1984 | European Pat. Off. . |
| 0130407 | 1/1985 | European Pat. Off. . |
| 0183423 | 4/1986 | European Pat. Off. . |
| 0180983 | 5/1986 | European Pat. Off. . |
| 7169444 | 10/1982 | Japan . |
| 9227841 | 12/1984 | Japan . |

OTHER PUBLICATIONS

Mochida, I., Yasutake, A., Fujitsu, H. and Takeshita, K., Journal of Catalysis 82, 313-321 (1983).

*Primary Examiner*—Paul Lieberman
*Assistant Examiner*—Christine A. Skane
*Attorney, Agent, or Firm*—Thomas K. McBride

[57] ABSTRACT

This invention relates to a process for preparing an alkylamine by contacting an alcohol and at least one of ammonia, a primary amine, a secondary amine or a tertiary amine with a non-zeolitic molecular sieve under conditions effective to produce the alkylamine.

62 Claims, No Drawings

PROCESS FOR THE PRODUCTION OF ALKYLAMINES

BRIEF SUMMARY OF THE INVENTION

1. Technical Field

This invention relates to a process for the production of alkylamines. More specifically, this invention relates to a process for the reaction of an alcohol with ammonia by contacting the alcohol and ammonia with a non-zeolitic molecular sieve. The process of this invention is particularly, though not exclusively, intended for the reaction of methanol with ammonia to selectively produce monomethylamine.

2. Background of the Invention

Lower aliphatic alkylamines, that is methyl-, ethyl and propylamines, are large volume commodity chemicals. Processes for their manufacture include, for example, the reaction of methanol and ammonia over an acidic dehydration catalyst and the reaction of ethanol or propanol and ammonia over either an acidic dehydration catalyst or a reductive amination catalyst.

These processes suffer from the disadvantage that the alkylamine products generally are not produced in relative amounts corresponding to market demands. For example, the reaction of methanol with ammonia gives monomethylamine as the primary product. Monomethylamine, however, is more reactive than ammonia so it reacts readily with methanol to give dimethylamine. Similarly, dimethylamine reacts with methanol to give trimethylamine. This tends to favor production of di- and trimethylamine to a larger extent than the market demands. Many catalysts give an equilibrium distribution of alkylamine products. When utilizing these processes known in the art, it is possible to increase the yield of monomethylamine by (i) running the reaction with a large excess of ammonia, (ii) running the reaction at low conversion, and (iii) recycling di- and trimethylamine to force the production of monomethylamine.

Various processes are known which describe the production of alkylamines from ammonia and alcohols using aluminosilicate zeolites. For example, U.S. Pat. No. 4,254,061 discloses a catalytic process for producing monomethylamine from methanol and ammonia by reacting methanol and ammonia in such amounts so as to provide a carbon/nitrogen (C/N) ratio from the methanol and ammonia reactants of 0.5-1.5 over a catalyst selected from: (a) mordenite wherein the primary cation is Li, Na, HNa having at least 2% Na by weight, K, Ca, Sr, Ba, Ce, Zn or Cr; (b) ferrierite wherein the primary metal cation is Li, Na, K, Ca, Sr, Ba, Ce or Fe; (c) erionite ore; (d) calcium erionite; and (e) clinoptilolite ore; at a temperature of 250°-475° C., a pressure of 7-7000 kPa, a contact time normalized to 7 kPa of 0.1 to 60 seconds and a methanol conversion of 15-95%.

European Patent Application No. 0 183 423 describes a process for producing dimethylamine by reacting methanol and/or dimethylether and ammonia in amounts sufficient to provide a carbon/nitrogen (C/N) ratio of from about 0.2 to about 1.5 at a temperature from about 250° C. to about 450° C. in the presence of a catalytic amount of zeolite catalyst selected from: (a) acidic zeolite rho; (b) acidic zeolite zk 5; and (c) acidic natural, H-exchanged and M exchanged chabazites, each having a geometric selectivity index greater than about 3, wherein M is one or more alkali metal ions selected from the group consisting of Na, K, Rb and Cs.

European Pat. No. 064 380 discloses amorphous aluminosilicate catalysts containing 0.1-6% by weight of Na, K, Li, Ba or Sr which are useful for the preparation of monomethylamine, dimethylamine and trimethylamine from methanol or dimethylether and ammonia. It is disclosed that such catalysts allow the monomethylamine:dimethylamine: trimethylamine weight ratio (normally 15:23:62) to be altered at will.

U.S. Pat. No. 4,434,300 describes a process for improving the methanol conversion rate in the reaction of methanol and ammonia to produce methylamines by effecting the reaction in the presence of a macroporous, highly acidic aluminosilicate catalyst. Macroporous H-chabaziteerionite is described as the preferred catalyst.

U.S. Pat. No. 4,398,041 discloses a process for converting a $C_1$–$C_4$ alcohol to a non-equilibrium controlled distribution of mono, di- and trialkylamines. A mixture of the alcohol and ammonia is reacted in a first conversion reactor containing a shape selective crystalline aluminosilicate zeolite catalyst to yield a first product stream comprising the mono- and disubstituted alkylamines and substantially no trisubstituted alkylamine. A predetermined fraction of the first product stream is removed and the remainder of the stream is reacted in a second conversion reactor containing a catalyst which yields a second product stream comprising an equilibrium controlled distribution of the mono-, di- and trisubstituted alkylamine. The fraction of the first product stream and the second product stream are combined to yield an alkylamines stream comprising a non-equilibrium controlled alkylamines distribution.

European Patent Application No. 0 180 983 discloses a catalytic process for the amination of $C_{2-8}$ alkanols, the catalyst being a dealuminized zeolite having an increased Si:Al molar ratio over the original zeolite. A dealuminized H-mordenite catalyst is described as particularly effective for the amination of ethanol to give selectively mono and diethylamine without the formation of triethylamine.

European Patent Application No. 0 101 921 describes an improvement in the vapor phase catalytic production of an amine by the reaction of a mixture comprising a $C_{2-4}$ olefin and ammonia. The improvement which provides for high conversion and selectivity to the amine resides in the use of an acidic offretite as the catalyst.

European Patent Application No. 0 039 918 discloses the vapor phase catalytic production of an amine by the reaction of a mixture comprising an olefin having from 2 to 8 carbon atoms and ammonia or ammonia type compound. The formation of polymers is prevented by applying a temperature ranging from 200° to 500° C., a pressure of from 300 to 6,000 psig and an aluminosilicate zeolite catalyst.

European Patent Application No. 0 107 457 describes a process for producing methylamines from methanol and/or dimethylether and ammonia by reaction over a synthetic levynite-type zeolite. It is disclosed that such catalysts give a good yield of monomethylamine in preference to dimethylamine and very little trimethylamine.

European Patent Application No. 0 076 034 discloses a process for the manufacture of methylamines which involves reacting a feed containing methanol and/or dimethylether and ammonia over a binderless zeolite A catalyst, preferably a binderless zeolite 5A catalyst. Use of binderless zeolite 5A makes the process selective to dimethylamine in preference to mono and trimethylamine. It is disclosed that if the catalyst is essentially free of alkali metal it is not only more active than similar catalysts containing alkali metal but also more selective.

U.S. Pat. No. 4,082,805 describes a process for the production of aliphatic amines by reaction of a $C_1$–$C_5$ alcohol or ether with ammonia in the presence of a catalyst comprising a crystalline aluminosilicate having the structure of ZSM-5, ZSM-11 or ZSM-21, said reaction being effected at a temperature between about 300° and about 500° C., a pressure between atmospheric and 1000 psig with the relative feed rates, expressed in grams per hour, of (1) alcohol or ether and (2) ammonia being within the approximate range of 1:1 to 5:1.

European Patent Application No. 0 130 407 and Japan Pat. No. 5 9227 841 disclose a process for producing dimethylamine by the gas phase reaction of ammonia and methanol over a zeolite catalyst (mordenite, clinoptilolite, erionite) treated with an atmosphere containing steam at 250° C.–700° C.

European Patent Application No. 0 125 616 describes a process for producing dimethylamine with high selectivity by reaction between (a) methanol and ammonia; (b) methanol, a mixture of methylamines and ammonia; or (c) a mixture of methylamines and ammonia; in gas phase over a solid catalyst which is a mordenite type zeolite. The catalyst has a sodium content of 0.2–3.9 grams per 100 grams of catalyst and an alkali metal total content of 0.01–0.20 mole per 100 grams of catalyst. The alkali metal is sodium, potassium or lithium.

Japan Pat. No. 5 7169 444 describes the preparation of methylamine by reacting methanol and ammonia in the presence of a mordenite type zeolite, preferably naturally occurring mordenite or a synthetic small pore mordenite with a part of its alkali metal ions displaced with a hydrogen ion or a di- or trivalent metal. It is disclosed that a mordenite type zeolite inhibits formation of trimethylamine (TMA) which is of low commercial value and has a specific selectivity to dimethylamine (DMA) which is of high commercial value.

Mochida, I., Yasutake, A., Fujitsu, H. and Takeshita, K., Journal of Catalysis 82, 313 321 (1983) disclose the selective production of dimethylamine (DMA) from methanol and ammonia over some zeolites and metal oxides at a temperature range of 300° to about 450° C. under ambient pressures. Proton or alkali-earth ion exchanged zeolites were found to show considerable selectivity around 50% (product mole base) at 400° C. The selectivity for the sum of DMA and monomethylamine (MMA) which can be recycled again for DMA production was over 85% at the conversion level of 90%, indicating suppression of trimethylamine (TMA) formation over the zeolite. The selectivity is discussed in terms of the type, strength, and steric environment of the acidic active sites. The activation of ammonia, desorption of DMA, and the shape selective discrimination of the pore structure for TMA are discussed as factors for the selectivity.

It has now been discovered that the reaction of methanol with ammonia to selectively produce monomethylamine can be efficiently conducted using non zeolitic molecular sieves as catalysts. The same catalysts can be used for the reaction of other alcohols with ammonia to produce alkylamines.

DISCLOSURE OF THE INVENTION

This invention relates to a process for the reaction of an alcohol with at least one of ammonia, a primary amine, a secondary amine or a tertiary amine by contacting the alcohol and at least one of ammonia, a primary amine, a secondary amine or a tertiary amine with a non zeolitic molecular sieve under conditions effective to produce alkylamines. In particular, this invention relates to a process for the reaction of methanol with ammonia by contacting methanol and ammonia with a non zeolitic molecular sieve under conditions effective to selectively produce monomethylamine.

DETAILED DESCRIPTION

As indicated above, this invention relates to a process for preparing an alkylamine, which process comprises contacting an alcohol and at least one of ammonia, a primary amine, a secondary amine or a tertiary amine with a non zeolitic molecular sieve under conditions effective to produce the alkylamine. In a preferred embodiment, this invention relates to a process for selectively producing monomethylamine, which process comprises contacting methanol and ammonia with a non zeolitic molecular sieve under conditions effective to selectively produce monomethylamine.

The process of this invention represents a highly desirable route to alkylamines. In particular, the process of this invention represents a highly desirable route to monomethylamine in high selectivities.

Alcohols suitable for use as reactants in the process of this invention have the general formula $R_1OH$ wherein $R_1$ is an alkyl radical, straight or branched chain, having from 1 to 12 carbon atoms. Illustrative alcohols include methanol, ethanol, n propanol, isopropanol, n-butanol, isobutanol, sec-butanol, tert-butanol and the like. Methanol is the preferred alcohol for use in the process of this invention.

Ammonia and the primary, secondary and tertiary amines which are used as reactants in the process of this invention are represented by the formula:

$$N-(R')_3.$$

wherein the R' groups can be the same or different and are hydrogen or an alkyl ($C_1$ to $C_{12}$) radical, preferably a lower alkyl ($C_1$ to $C_4$) radical such as methyl or ethyl. Illustrative primary and secondary amines include monomethylamine, dimethylamine, monoethylamine, diethylamine and the like.

The alcohol:ammonia (C/N) mole ratio utilized in the process of this invention can vary over a wide range depending on the mix of mono-, di- and trialkylamines desired. For example, in the preparation of methylamines, a high C/N ratio will give a product high in trimethylamine while a low C/N ratio will give a product high in monomethylamine. C/N ratios above about 2.0 will give predominantly di- and trimethylamine. C/N ratios below about 0.1 will give predominantly monomethylamine. Intermediate C/N ratios will give intermediate product mixes. There is generally no incentive to use C/N ratios much above about 5.0 as little extra di- and trimethylamines are formed but the cost of recycling the methanol increases. Similarly, there is generally no incentive to use C/N ratios much below about 0.05 as little extra monomethylamine is formed but the cost of recycling the ammonia increases.

The optimum C/N ratio depends not only on the product ratio desired but also on the other reaction conditions. At high pressure, the cost of recycling ammonia or methanol increases. Since the product ratio changes with changing methanol conversion, the optimum C/N ratio for any desired product mix will change with pressure or temperature or anything else that affects the conversion.

The alkylamines which can be produced by the process of this invention include, for example, methylamines, ethylamines, n-propylamines, i-propylamines, n-butylamines and the like. The monosubsituted:disubstituted:trisubstituted alkylamine ratio can be controlled; for example, high selectivities of monomethylamine versus dimethylamine and trimethylamine can be obtained by the process of this invention.

The non zeolitic molecular sieves used as catalysts in the process of this invention include a large number of aluminophosphates and silicoaluminophosphates having a variety of crystal structures, which may include one or more other elements in addition to aluminum, phosphorous and silicon. Accordingly, the manner in which the non-zeolitic molecular sieves are used as catalysts in the process of this invention will first be described, and thereafter the chemical nature and methods for the preparation of the non-zeolitic molecular sieves will be described.

As already mentioned, in the process of this invention an alcohol and ammonia are contacted with a non-zeolitic molecular sieve under conditions effective to produce alkylamines. As is well known to those familiar with the use of molecular sieves as catalysts, the reaction rate and product distribution of a molecular sieve catalyzed reaction is strongly influenced by the pore size of the molecular sieve, since the catalytic activity of molecular sieves appears to depend upon the ability of the reactants and products to diffuse through the pores of the molecular sieve. The pore sizes of the non zeolitic molecular sieves vary over a wide range and, since amination of alcohols such as methanol with ammonia to give alkylamines such as monomethylamine involves the diffusion of molecules of moderately small size through the non zeolitic molecular sieve, the non zeolitic molecular sieve used as catalyst in the process of this invention should be selected to provide a sufficient pore size to accommodate these molecules.

The non zeolitic molecular sieves may be divided into small, medium and large pore materials. The small pore materials are those having, in their calcined form, an adsorption of isobutane of less than about 2 percent by weight of the non zeolitic molecular sieve at a partial pressure of 500 torr and a temperature of 20° C. The medium pore materials are those having, in their calcined form, an adsorption of isobutane of at least about 2 percent, and preferably at least about 4 percent, and an adsorption of triethylamine of less than 5 percent by weight of the non zeolitic molecular sieve at a partial pressure of 2.6 torr and a temperature of 22° C. The large pore materials are those having, in their calcined form, an adsorption of isobutane of at least about 2 percent, and an adsorption of triethylamine of at least 5 percent, by weight of the non zeolitic molecular sieve at a partial pressure of 2.6 torr and a temperature of 22° C. Empirically, it appears that in the reaction of methanol with ammonia, small pore materials tend to give better selectivities to monomethylamine than medium pore materials.

As synthesized by the methods described below, the non-zeolitic molecular sieves normally contain within their internal pore systems at least one form of the organic templating agent employed in their formation. Before being used in the process of this invention, the non zeolitic molecular sieves need to have this templating agent removed. Preferably, the templating agent is removed by calcining the as-synthesized non-zeolitic molecular sieve at an elevated temperature, normally at least 500° C., before the non zeolitic molecular sieve is used in the process of the present invention. Alternatively, if the process of this invention is to be conducted under conditions (especially temperature) which are sufficient to remove the templating agent from the as synthesized non-zeolitic molecular sieve, the non-zeolitic molecular sieve may be placed in the reactor to be used for the process and the templating agent thus removed in situ during the process. However, such in situ removal of the templating agent is usually less desirable than prior calcination of the non zeolitic molecular sieve.

Specific preferred non zeolitic molecular sieves for use in the process of this invention are SAPO-11 and SAPO-34 (for descriptions of these SAPO materials see U.S. Pat. No. 4,400,871).

Selection of the temperature at which the process of this invention is to be conducted involves a compromise between selectivity to the desired alkylamine product and conversion of the alcohol used as starting material. It is recommended that the process of this invention be conducted at a temperature in the range of about 250° C. to about 500° C.; below this temperature range, the reaction tends to proceed too slowly, while at very high temperatures, the selectivity to the desired monomethylamine product tends to decrease. The preferred temperature range is from about 300° C. to about 450° C. For obvious reasons, it is desirable to adjust the temperature and other reaction parameters discussed below so as to ensure that the reaction is run at a methanol conversion of at least about 10%, and preferably at least about 20%, and at a selectivity to monomethylamine of at least about 40%, and preferably at least about 50%. It should be noted that the conversion and selectivity achieved with a given material may vary considerably with its exact composition and the procedure and raw materials used to prepare a given specimen of the material.

The process of this invention can be run over a wide range of pressures ranging from sub-atmospheric pressures to 1000 psig (6.9 MPa.) or more. However, since the use of very high pressures does not confer any significant advantages but increases equipment costs, it is recommended that the process of the present invention be carried out at a pressure of from about atmospheric pressure to about 500 psig (about 0.7 MPa.). It has been found that satisfactory conversions and selectivities can be achieved by running the process of the invention under atmospheric pressure. Because the rate of reaction should increase at higher pressures, it may be advantageous to run at somewhat elevated pressures. But this advantage is offset by the higher cost of equipment required for high pressure operations.

The process of the present invention can also be carried out over a wide range of weight hourly space velocities of the alcohol. For example, weight hourly space velocities of from about 0.1 to about 50 may be employed, with the preferred range of weight hourly space velocity being from about 0.5 to about 10. At high weight hourly space velocities the conversion tends to decrease, and at low weight hourly space velocities the catalyst productivity tends to be low. The optimum weight hourly space velocity will depend on the temperature and pressure of the reaction.

The non zeolitic molecular sieve catalysts used in the process of this invention enable the reaction to be carried out at high selectivities. As illustrated in the Examples below, the process of this invention can be carried out with a selectivity to monoethylamine of at least about 60%.

As with some reactions catalyzed by non zeolitic molecular sieves, the conversion achieved in the process of the present invention may fall as the time for which the non zeolitic molecular sieve catalyst has been used in the process increases. If the non zeolitic molecular sieve catalysts become deactivated, the deactivated catalyst can readily be regenerated by heating in air at an appropriate temperature (typically about 500° C.) and for an appropriate period (typically one hour).

The non zeolitic molecular sieve may be modified by depositing or impregnating the non-zeolitic molecular sieve with cations, anions or salts so as to improve its efficacy as a catalyst in the process of this invention. Techniques which may be employed to effect the deposition or impregnation of a non zeolitic molecular sieve are generally known in the art. Such techniques may involve such procedures as (1) impregnating the non-zeolitic molecular sieve with a solution comprising a solvent or solubilizing agent of one or more such modifying materials in an amount sufficient to deposit the desired weight of such materials in the non-zeolitic molecular sieve and/or (2) exchanging the non-zeolitic molecular sieve with a solution containing the modifying material. The impregnation or deposition of the modifying materials may generally be accomplished by heating the non-zeolitic molecular sieve at an elevated temperature to evaporate any liquid present to effect deposition or impregnation of the modifying material on to the interior and/or exterior surface of the non zeolitic molecular sieve, or by the exchange of cations present in the non-zeolitic molecular sieve with cations that provide for the desired properties (provided of course that the non-zeolitic molecular sieve is one having a significant ion exchange capacity). Alternatively, the modifying material may be formed on the non-zeolitic molecular sieve from a solution or an emulsion or a slurry containing the modifying material by conventional methods known in the art. Impregnation or exchange procedures are generally the preferred techniques because they utilize and introduce the modifying material more efficiently than other procedures such as coating procedures since a coating procedure is generally not able to effect substantial introduction of the modifying material on to the interior surfaces of the non zeolitic molecular sieve. In addition, coated materials are more generally susceptible to the loss of the modifying materials by abrasion.

Suitable modifying materials include alkali metals, alkaline earth metals, transition metals and the salts thereof including inorganic and organic salts such as nitrates, halides, hydroxides, sulfates and carboxylates. Other modifying materials generally employed in the art are also believed to be employable in the non zeolitic molecular sieves.

In carrying out the process of this invention, the non zeolitic molecular sieves may be admixed (blended) or provided sequentially to other materials which may provide some property which is beneficial under process conditions, such as improved temperature resistance or improved catalyst life by minimization of coking, or which are simply inert under the process conditions used. Such materials may include synthetic or naturally-occurring substances such as clays, silicas, aluminas, metal oxides and mixtures thereof. In addition, the non zeolitic molecular sieves may be formed with materials such as silica, alumina, silica alumina, silica magnesia, silica-zirconia, silica-thoria, silica berylia, and silica titania, as well as ternary compositions, such as silica-alumina thoria, silica alumina zirconia and clays present as binders. The relative proportions of the above materials and the non-zeolitic molecular sieves may vary widely with the non zeolitic molecular sieve content ranging between about 1 and about 99 percent by weight of the composite.

The process of this invention may be carried out using, for example, a fixed bed reactor, a fluid bed reactor, or a slurry reactor. The optimum size and shape of the catalyst particle will depend on the type of reactor used. In general, for fluid bed reactors, a small, spherical catalyst particle is preferred for easy fluidization. With fixed bed reactors, larger catalyst particles are preferred so the back pressure within the reactor is kept reasonably low.

The process of this invention can be conducted in a batch or continuous fashion. The reaction can be conducted in a single reaction zone or in a plurality of reaction zones, in series or in parallel or it may be conducted batchwise or continuously in an elongated tubular zone or series of such zones. The materials of construction employed should be inert to the reactants during the reaction and the fabrication of the equipment should be able to withstand the reaction temperatures and pressures. Means to introduce and/or adjust the quantity of reactions or ingredients introduced batchwise or continuously into the reaction zone during the course of the reaction can be conveniently utilized in the process especially to maintain the desired molar ratio of the reactants.

The process may be conducted in either glass lined, stainless steel or similar type reaction equipment. The reaction zone may be fitted with one or more internal and/or external heat exchanger(s) in order to control undue temperature fluctuations, or to prevent any possible "runaway" reaction temperatures.

The following is a description of the chemical nature and methods for preparation of the non-zeolitic molecular sieves used as catalysts in the process of this invention.

NON ZEOLITIC MOLECULAR SIEVES

The term "non zeolitic molecular sieves" or "NZMS" is defined in the instant invention to include the "SAPO" molecular sieves of U.S. Pat. No. 4,440,871 and U.S. Ser. No. 575,745, filed Jan. 31, 1984, "ELAPSO" molecular sieves as disclosed in U.S. Ser. No. 600,312, filed Apr. 13, 1984, and certain "AlPO$_4$", "MeAPO", "FeAPO", "TAPO" and "ELAPO" molecular sieves, as hereinafter described. Crystalline "AlPO$_4$" aluminophosphates are disclosed in U.S. Pat. No. 4,310,440 issued Jan. 12, 1982, and in U.S. Ser. No. 880,559, filed June 30, 1986; crystalline metal aluminophosphates (MeAPOs where "Me" is at least one of Mg, Mn, Co and Zn) are disclosed in U.S. Pat. No. 4,567,029, issued Jan. 28, 1986; crystalline ferroaluminophosphates (FeAPOs) are disclosed in U.S. Pat. No. 4,554,143, issued Nov. 19, 1985; titanium aluminophosphates (TAPOs) are disclosed in U.S. Pat. No. 4,500,651, issued Feb. 19, 1985; certain non-zeolitic molecular sieves ("ELAPO") are disclosed in EPC Patent Application No. 85104386.9 (Publication No. 0158976, published Oct. 13, 1985) and 85104388.5 (Publication No. 158349, published Oct. 16, 1985); and ELAPSO molecular sieves are disclosed in copending U.S. Ser. No. 600,312, filed Apr. 13, 1984 (EPC Publication No. 0159624, published Oct. 30, 1985). The aforementioned applications and patents are incorporated herein by reference thereto. The nomenclature employed herein to refer to the members of the aforementioned NZMSs is consistent with that employed in the aforementioned applications or patents. A particular member of a class is generally referred to as a "−n" species wherein "n" is an integer, e g , SAPO-11, MeAPO-11 and ELAPSO-31. In the following discussion on NZMSs set forth hereinafter the mole fraction of the NZMSs are defined as compositional values which are plotted in phase diagrams in each of the identified patents, published applications or copending applications.

ELAPSO MOLECULAR SIEVES

"ELAPSO" molecular sieves are described in copending U.S. Ser. No. 600,312, filed Apr. 13, 1984, (EPC Publication No. 0159,624, published Oct. 30, 1985, incorporated herein by reference) as crystalline molecular sieves having three-dimensional microporous framework structures of $ELO_2$, $AlO_2$, $PO_2$, $SiO_2$ oxide units and having an empirical chemical composition on an anhydrous basis expressed by the formula:

mR: $(EL_wAl_xP_ySi_z)O_2$ wherein "R" represents at least one organic templating agent present in the intracrystalline pore system; "m" represents the molar amount of "R" present per mole of $(EL_wAl_xP_ySi_z)$ and has a value of from zero to about 0.3; "EL" represents at least one element capable of forming a three dimensional oxide framework, "EL" being characterized as an element having a mean "T-O" distance in tetrahedral oxide structures between about 1.51 Angstroms and about 2.06 Angstroms, "EL" having a cation electronegativity between about 125 Kcal/g atom to about 310 Kcal/gm atom and "EL" being capable of forming stable M-O-P, M-O-Al or M-O-M bonds in crystalline three dimensional oxide structures having a "M-O" bond dissociation energy greater than about 59 kcal/g atom at 298° K.; and "w", "x", "y" and "z" represent the mole fractions of "EL", aluminum, phosphorus and silicon, respectively, present as framework oxides, said mole fractions being within the limiting compositional values or points as follows:

| Point | Mole Fraction | | |
|---|---|---|---|
| | x | y | (z + w) |
| A | 0.60 | 0.39−(0.01)p | 0.01(p + 1) |
| B | 0.39−(0.01p) | 0.60 | 0.01(p + 1) |
| C | 0.01 | 0.60 | 0.39 |
| D | 0.01 | 0.01 | 0.98 |
| E | 0.60 | 0.01 | 0.39 | where "p" is an integer corresponding to the number of elements "El" in the $(El_wAl_xP_ySi_z)O_2$ constituent.

The "ELAPSO" molecular sieves are also described as crystalline molecular sieves having three-dimensional microporous framework structures of $ELO_2$, $AlO_2$, $SiO_2$ and $PO_2$ tetrahedral oxide units and having an empirical chemical composition on an anhydrous basis expressed by the formula:

mR: $(EL_wAl_xP_ySi_z)O_2$ wherein "R" represents at least one organic templating agent present in the intracrystalline pore system; "m" represents the molar amount of "R" present per mole of $(EL_wAl_xP_ySi_z)O_2$ and has a value of from zero to about 0.3; "EL" represents at least one element capable of forming a framework tetrahedral oxide and is selected from the group consisting of arsenic, beryllium, boron, chromium, cobalt, gallium, germanium, iron, lithium, magnesium, manganese, titanium and zinc; and "w", "x", "y" and "z" represent the mole fractions of "EL", aluminum, phosphorus and silicon, respectively, present as tetrahedral oxides, said mole fractions being within the limiting compositional values or points as follows:

| Point | Mole Fraction | | |
|---|---|---|---|
| | x | y | (z + w) |
| a | 0.60 | 0.39−(0.01)p | 0.01(p + 1) |
| b | 0.39−(0.01p) | 0.60 | 0.01(p + 1) |
| c | 0.10 | 0.55 | 0.35 |
| d | 0.55 | 0.10 | 0.35 | where "p" is as above defined.

The "ELAPSO" molecular sieves include numerous species which are intended herein to be within the scope of the term "non zeolitic molecular sieves" such being disclosed in the following copending and commonly assigned applications, incorporated herein by reference thereto [(A) following a serial number indicates that the application is abandoned, while (CIP) following a serial number indicates that the application is a continuation-in part of the immediately preceding application and (C) indicates that the application is a continuation of the immediately preceding application]:

| U.S. Ser. No. | Filed | NZMS |
|---|---|---|
| 599,808(a) | April 13, 1984 | AsAPSO |
| 845,484(CIP) | March 31, 1986 | AsAPSO |
| 600,177(A) | April 13, 1984 | BAPSO |
| 845,255(CIP) | March 28,1986 | BAPSO |
| 600,176(A) | April 13, 1984 | BeAPSO |
| 841,752(CIP) | March 20,1986 | BeAPSO |
| 599,830(A) | April 13, 1984 | CAPSO |
| 852,174(CIP) | April 15, 1986 | CAPSO |
| 599,925(A) | April 13, 1984 | GaAPSO |
| 845,985(CIP) | March 31, 1986 | GaAPSO |
| 599,971(A) | April 13, 1984 | GeAPSO |
| 852,175(CIP) | April 15, 1986 | GeAPSO |
| 599,952(A) | April 13, 1984 | LiAPSO |
| 847,227(CIP) | April 2, 1986 | LiAPSO |
| 600,179 | April 13, 1984 | TiAPSO |
| (now U.S. Pat. No. 4,684,617 issued August 4, 1987) | | |
| 049,274(C) | May 13, 1987 | TiAPSO |
| 600,180 | April 13, 1984 | MgAPSO |
| 600,175 | April 13, 1984 | MnAPSO |
| (now U.S. Pat. No. 4,686,092 issued August 11, 1987) | | |
| 600,174 | April 13, 1984 | CoAPSO |
| 600,170 | April 13, 1984 | ZnAPSO |
| 600,173 | April 13, 1984 | FeAPSO |
| (now U.S. Pat. No. 4,683,217 issued July 28, 1987) | | |
| 600,168(A) | April 13, 1984 | QuinAPSO |
| 063,791(C) | June 22, 1987 | QuinAPSO |
| 600,181 | April 13, 1984 | QuinAPSO |
| 600,182 | April 13, 1984 | CoMnMgAPSO |
| 057,648(C) | June 9, 1987 | CoMnMgAPSO |
| 600,183 | April 13, 1984 | SenAPSO |

TiAPSO MOLECULAR SIEVES

The TiAPSO molecular sieves of U.S. Ser. No. 600,179, filed Apr. 13, 1984 (now U.S. Pat. No. 4,684,617), and U.S. Ser. No. 049,274, filed May 13, 1987, have three dimensional microporous framework structures of $TiO_2$, $AlO_2^-$, $PO_2^+$ $SiO_2$ tetrahedral oxide units having an empirical chemical composition on an anhydrous basis expressed by the formula:

$$mR: (Ti_wAl_xP_ySi_z)O_2$$

wherein "R" represents at least one organic templating agent present in the intracrystalline pore system; "m" represents the molar amount of "R" present per mole of $(Ti_wAl_xP_ySi_z)O_2$ and has a value of from zero to about 0.3; and "w", "x", "y" and "z" represent the mole fractions of titanium, aluminum phosphorus and silicon, respectively, present as tetrahedral oxides and each has a value of at least 0.01. The mole fractions "w", "x", "y" and "z" are generally defined as being within the limiting compositional values or points as follows:

| Point | Mole Fraction | | |
|---|---|---|---|
| | x | y | (z + w) |
| A | 0.60 | 0.38 | 0.02 |
| B | 0.38 | 0.60 | 0.02 |
| C | 0.01 | 0.60 | 0.39 |
| D | 0.01 | 0.01 | 0.98 |
| E | 0.60 | 0.01 | 0.39 |

In a subclass of TiAPSO molecular sieves the values "w", "x", "y" and "z" in the above formula are within the tetragonal compositional area defined by points a, b, c and d, said points a, b, c and d representing the following values for "w", "x", "y" and "z":

| Point | Mole Fraction | | |
|---|---|---|---|
| | x | y | (z + w) |
| a | 0.55 | 0.43 | 0.02 |
| b | 0.43 | 0.55 | 0.02 |
| c | 0.10 | 0.55 | 0.35 |
| d | 0.55 | 0.10 | 0.35 |

TiAPSO compositions are generally synthesized by hydrothermal crystallization from a reaction mixture containing active sources of titanium, silicon, aluminum and phosphorus, and preferably an organic templating, i.e., structure directing, agent, preferably a compound of an element of Group VA of the Periodic Table, and/or optionally an alkali or other metal. The reaction mixture is generally placed in a sealed pressure vessel, preferably lined with an inert plastic material such as polytetrafluoroethylene and heated, preferably under autogenous pressure at a temperature between 50° C. and 250° C., and preferably between 100° C. and 200° C. until crystals of the TiAPSO product are obtained, usually a period of from hours to several weeks. Generally, the crystallization time is from about 2 hours to about 30 days and typically from about 4 hours to about 20 days. The product is recovered by any convenient method such as centrifugation or filtration.

In synthesizing the TiAPSO, it is preferred to employ a reaction mixture composition expressed in terms of the molar ratios as follows:

$$aR: (Ti_wAl_xP_ySi_z)O_2: bH_2O$$

wherein "R" is an organic templating agent; "a" is the amount of organic templating agent "R" and has a value of from zero to about 6 and is preferably an effective amount within the range of greater than zero (0) to about 6; "b" has a value of from zero (0) to about 500, preferably between about 2 and about 300; and "w", "x", "y" and "z" represent the mole fractions of titanium, aluminum, phosphorus and silicon, respectively, and each has a value of at least 0.01.

In one embodiment the reaction mixture is selected such that the mole fractions "w", "x", "y" and "z" are generally defined as being within the limiting compositional values or points as follows:

| Point | Mole Fraction | | |
|---|---|---|---|
| | x | y | (z + w) |
| F | 0.60 | 0.38 | 0.02 |
| G | 0.38 | 0.60 | 0.02 |
| H | 0.01 | 0.60 | 0.39 |
| I | 0.01 | 0.01 | 0.98 |
| J | 0.60 | 0.01 | 0.39 |

In the foregoing expression of the reaction composition, the reactants are normalized with respect to the total of "w", "x", "y" and "z" such that $(w+x+y+z)=1.00$ mole. Molecular sieves containing titanium, aluminum, phosphorus and silicon as framework tetrahedral oxides are prepared as follows:

Preparative Reagents

TiAPSO compositions are typically prepared using numerous reagents. Typical reagents which may be employed and abbreviations employed in U.S. Ser. No. 600,179 for such reagents are as follows:

(a) Alipro: aluminum isopropoxide;
(b) LUDOX LS: LUDOX LS is the tradename of DuPont for an aqueous solution of 30 weight percent $SiO_2$ and 0.1 weight percent $Na_2O$;
(c) $H_3PO_4$: 85 weight percent aqueous phosphoric acid;
(d) Tiipro: titanium isopropoxide;
(e) TEAOH: 40 weight percent aqueous solution of tetraethylammonium hydroxide;
(f) $Pr_2NH$: di-n-propylamine, $(C_3H_7)_2NH$:
(g) $Pr_3NH$: tri-n-propylamine, $(C_3H_7)_3N$;
(h) Quin: Quinuclidine, $(C_7H_{13}N)$;
(i) MQuin: Methyl Quinuclidine hydroxide, $(C_7H_{13}NCH_3OH)$; and
(j) C-hex: cyclohexylamine.

Preparative Procedures

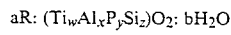

TiAPSOs may be prepared by forming a starting reaction mixture by adding the $H_3PO_4$ and the water. This mixture is mixed and to this mixture aluminum isopropoxide is added. This mixture is then blended until a homogeneous mixture is observed. To this mixture the LUDOX LS is added and the resulting mixture blended (about 2 minutes) until a homogeneous mixture is observed.

The titanium isopropoxide is added to the above mixture and the resulting mixture blended until a homogeneous mixture is observed. The organic templating agent is then added to the resulting mixture and the resulting mixture blended until a homogeneous mixture is observed, i.e., about 2 to 4 minutes. When the organic templating agent is quinuclidine the procedure is modified such that the quinuclidine is dissolved in about one half the water and accordingly the $H_3PO_4$ is mixed with about one half the water. (The pH of the mixture is measured and adjusted for temperature). The mixture is then placed in a lined (polytetrafluoroethylene) lined stainless steel pressure vessel and digested at a temperature (150° C. or 200° C.) for a time or placed in lined screw top bottles for digestion at 100° C. Digestions are typically carried out under autogenous pressure.

The products are removed from the reaction vessel and cooled.

MgAPSO MOLECULAR SIEVES

The MgAPSO molecular sieves of U.S. Ser. No. 600,180, filed Apr. 13, 1984 have three-dimensional microporous framework structures of $MgO_2^{-2}$, $AlO_2^{-}$, $PO_2^{+}$ and $SiO_2$ tetrahedral oxide units and have an empirical chemical composition on an anhydrous basis expressed by the formula:

$$mR: (Mg_2Al_xP_ySi_z)O_2$$

wherein "R" represents at least one organic templating agent present in the intracrystalline pore system; "m" represents the molar amount of "R" present per mole of $(Mg_wAl_xP_ySi_z)O_2$ and has a value from zero (0) to about 0.3; and "w", "x", "y" and "z" represent the mole fractions of magnesium, aluminum, phosphorus and silicon, respectively, present as tetrahedral oxides and each preferably has a value of at least 0.01. The mole fractions "w", "x", "y" and "z" are generally defined as being within the limiting compositional values or points as follows:

| | Mole Fraction | | |
|---|---|---|---|
| Point | x | y | (z + w) |
| A | 0.60 | 0.38 | 0.02 |
| B | 0.39 | 0.59 | 0.02 |
| C | 0.01 | 0.60 | 0.39 |
| D | 0.01 | 0.01 | 0.98 |
| E | 0.60 | 0.01 | 0.39 |

In a preferred subclass of the MgAPSO molecular sieves the values "w", "x", "y" and "z" in the above formula are within the limiting compositional values or points as follows:

| | Mole Fraction | | |
|---|---|---|---|
| Point | x | y | (z + w) |
| a | 0.55 | 0.43 | 0.02 |
| b | 0.43 | 0.55 | 0.02 |
| c | 0.10 | 0.55 | 0.35 |
| d | 0.55 | 0.10 | 0.35 |

MgAPSO compositions are generally synthesized by hydrothermal crystallization for an effective time at effective pressures and temperatures from a reaction mixture containing reactive sources of magnesium, silicon, aluminum and phosphorus, an organic templating, i.e., structure-directing, agent, preferably a compound of an element of Group VA of the Periodic Table, and may be an alkali or other metal. The reaction mixture is generally placed in a sealed pressure vessel, preferably lined with an inert plastic material such as polytetrafluoroethylene and heated, preferably under autogenous pressure at a temperature between 50° C. and 250° C., and preferably between 100° C. and 200° C. until crystals of the MgAPSO product are obtained, usually a period of from several hours to several weeks. Generally, the crystallization period will be from about 2 hours to about 30 days with it typically being from about 4 hours to about 20 days for obtaining MgAPSO crystals. The product is recovered by any convenient method such as centrifugation or filtration.

In synthesizing the MgAPSO compositions, it is preferred to employ reaction mixture compositions expressed in terms of the molar ratios as follows:

$$aR: (Mg_wAl_xP_ySi_z)O_2: bH_2O$$

wherein "R" is an organic templating agent; "a" is the amount of organic templating agent "R" and can have a value within the range of from zero (0) to about 6 and is more preferably an effective amount greater than zero to about 6; "b" has a value of from zero (0) to about 500, preferably between about 2 and about 300; and "w", "x", "y" and "z" represent the mole fractions of magnesium, aluminum, phosphorus and silicon, respectively, and each has a value of at least 0.01.

In one embodiment the reaction mixture is selected such that the mole fractions "w", "x", "y" and "z" are generally defined as being within the limiting compositional values or points as follows:

| | Mole Fraction | | |
|---|---|---|---|
| Point | x | y | (z + w) |
| F | 0.60 | 0.38 | 0.02 |
| G | 0.38 | 0.60 | 0.02 |
| H | 0.01 | 0.60 | 0.39 |
| I | 0.01 | 0.01 | 0.98 |
| J | 0.60 | 0.01 | 0.39 |

In the foregoing expression of the reaction composition, the reactants are normalized with respect to the total of "w", "x", "y" and "z" such that (w+x+y+z)=1.00 mole. Molecular sieves containing magnesium, aluminum, phosphorus and silicon as framework tetrahedral oxides are prepared as follows:

Preparative Reagents

MgAPSO compositions are prepared using numerous reagents. Typical reagents which may be employed to prepare MgAPSOs include:

(a) Alipro: aluminum isopropoxide;
(b) CATAPAL: Trademark of Condea for hydrated pseudoboehmite;
(c) LUDOX LS: Trademark of DuPont for an aqueous solution of 30 weight percent $SiO_2$ and 0.1 weight percent $Na_2O$;
(d) $Mg(Ac)_2$: magnesium acetate tetrahydrate, $Mg(C_2H_3O_2.4H_2O)$;
(e) $H_3PO_4$: 85 weight percent aqueous phosphoric acid in water;
(f) TBAOH: tetrabutylammonium hydroxide (40 wt. % in water);
(g) $Pr_2NH$: di-n-propylamine;
(h) $Pr_3NH$: tri-n-propylamine;
(i) Quin: Quinuclidine;
(j) MQuin: Methyl Quinuclidine hydroxide, (17.9%) in water);
(k) C-hex: cyclohexylamine;
(l) TEAOH: tetraethylammonium hydroxide (40 wt. % in water);
(m) DEEA: Diethylethanolamine;
(n) i-$Pr_2NH$: di-isopropylamine;
(o) TEABr: tetraethylammonium bromide; and
(p) TPAOH: tetrapropylammonium hydroxide (40 wt. % in water).

Preparative Procedures

The MgAPSO compositions may be prepared by preparing reaction mixtures having a molar composition expressed as:

eR:fMgO:hAl$_2$O$_3$:iP$_2$O$_5$:gSiO$_2$:jH$_2$O wherein e, f, g, h, i and j represent the moles of template R, magnesium (expressed as the oxide), SiO$_2$, Al$_2$O$_3$, P$_2$O$_5$ (H$_3$PO$_4$ expressed as P$_2$O$_5$) and H$_2$O, respectively.

The reaction mixtures may be prepared by the following representative procedures, designated hereinafter as Methods A, B and C.

Method A

The reaction mixture is prepared by mixing the ground aluminum source (alipro or CATAPAL) with the H$_3$PO$_4$ and water on a gradual basis with occasional cooling with an ice bath. The resulting mixture is blended until a homogeneous mixture is observed. When the aluminum source is CATAPAL the water and H$_3$PO$_4$ are first mixed with the CATAPAL added thereto. The magnesium acetate is dissolved in a portion of the water and is then added followed by addition of the LUDOX LS. The combined mixture is blended until a homogeneous mixture is observed. The organic templating agent is added to this mixture and blended until a homogeneous mixture is observed. The resulting mixture (final reaction mixture) is placed in a lined (polytetrafluoroethylene) stainless steel pressure vessel and digested at a temperature (150° C. or 200° C.) for an effective time. Alternatively, if the digestion temperature is 100° C. the final reaction mixture is placed in a lined (polytetrafluoroethylene) screw top bottle for a time. Digestions are typically carried out under autogenous pressure. The products are removed from the reaction vessel, cooled and evaluated as set forth hereinafter.

Method B

When method B is employed the organic templating agent is di-n propylamine. The aluminum source, silicon source and one half of the water are first mixed and blended until a homogeneous mixture is observed. A second solution was prepared by mixing the remaining water, the H$_3$PO$_4$ and the magnesium acetate. This solution is then added to the above mixture. The magnesium acetate and H$_3$PO$_4$ solution is then added to the above mixture and blended until a homogeneous mixture is observed. The organic templating agent(s) is/are then added and the resulting reaction mixture digested and product recovered as in Method A.

Method C

Method C is carried out by mixing aluminum isopropoxide, LUDOX LS and water in a blender or by mixing water and aluminum iso-propoxide in a blender followed by addition of the LUDOX LS. H$_3$PO$_4$ and magnesium acetate are then added to the resulting mixture. The organic templating agent is then added to the resulting mixture and digested and product recovered as in Method A.

MnAPSO MOLECULAR SIEVES

The MnAPSO molecular sieves of U.S. Ser. No. 600,175, filed Apr. 13, 1984 (now U.S. Pat. No. 4,686,092 issued Aug. 11, 1987), have a framework structure of MnO$_2^{-1}$, AlO$_2^-$, PO$_2^+$, and SiO$_2$ tetrahedral units having an empirical chemical composition on an anhydrous basis expressed by the formula:

mR: (Mn$_w$Al$_x$P$_y$Si$_z$)O$_2$ wherein "R" represents at least one organic templating agent present in the intracrystalline present pore system; "m" represents the molar amount of "R" present per mole of (Mn$_w$Al$_x$P$_y$Si$_z$)O$_2$ and has a value of zero to about 0.3; and "w", "x", "y" and "z" represent the mole fractions of the elements manganese, aluminum, phosphorus and silicon, respectively, present as tetrahedral oxides. The mole fractions "w", "x", "y" and "z" are generally defined as being within the limiting compositional values or points as follows:

| Point | Mole Fraction | | |
|---|---|---|---|
| | x | y | (z + w) |
| A | 0.60 | 0.38 | 0.02 |
| B | 0.38 | 0.60 | 0.02 |
| C | 0.01 | 0.60 | 0.39 |
| D | 0.01 | 0.01 | 0.98 |
| E | 0.60 | 0.01 | 0.39 |

The values of w, x, y and z may be as follows:

| Point | Mole Fraction | | |
|---|---|---|---|
| | x | y | (z + w) |
| a | 0.55 | 0.43 | 0.02 |
| b | 0.43 | 0.55 | 0.02 |
| c | 0.10 | 0.55 | 0.35 |
| d | 0.55 | 0.10 | 0.35 |

MnAPSO compositions are generally synthesized by hydrothermal crystallization from a reaction mixture containing reactive sources of manganese, silicon, aluminum and phosphorus, preferably an organic templating, i.e., structure directing, agent, preferably a compound of an element of Group VA of the Periodic Table, and/or optionally an alkali or other metal. The reaction mixture is generally placed in a sealed pressure vessel, preferably lined with an inert plastic material such as polytetrafluoroethylene and heated, preferably under autogenous pressure at a temperature between about 50° C. and about 250° C., and preferably between about 100° C. and about 200° C. until crystals of the MnAPSO product are obtained, usually a period of from several hours to several weeks. Typical effective times of from 2 hours to about 30 days, generally from about 4 hours to about 20 days, have been observed. The product is recovered by any convenient method such as centrifugation or filtration.

In synthesizing the MnAPSO compositions, it is preferred to employ a reaction mixture composition expressed in terms of the molar ratios as follows:

aR: (Mn$_w$Al$_x$P$_y$Si$_z$)O$_2$: bH$_2$O wherein "R" is an organic templating agent; "a" is the amount of organic templating agent "R" and has a value of from zero to about 6 and is preferably an effective amount within the range of greater than zero (0) to about 6; "b" has a value of zero (0) to about 500, preferably between about 2 and about 300; and "w", "x", "y" and "z" represent the mole fractions of manganese, aluminum, phosphorus and silicon, respectively, and each has a value of at least 0.01.

In one embodiment the reaction mixture is selected such that the mole fractions "w", "x", "y" and "z" are generally defined as being within the limiting compositional values or points as follows:

| Point | Mole Fraction | | |
|---|---|---|---|
| | x | y | (z + w) |
| F | 0.60 | 0.38 | 0.02 |
| G | 0.38 | 0.60 | 0.02 |
| H | 0.01 | 0.60 | 0.39 |
| I | 0.01 | 0.01 | 0.98 |
| J | 0.60 | 0.01 | 0.39 |

In the foregoing expression of the reaction composition, the reactants are normalized with respect to the total of "w", "x", "y" and "z" such that $(w+x+y+z)=1.00$ mole. Molecular sieves containing manganese, aluminum, phosphorus and silicon as framework tetrahedral oxide units are prepared as follows:

Preparative Reagents

MnAPSO compositions may be prepared by using numerous reagents. Reagents which may be employed to prepare MnAPSOs include:
(a) Alipro: aluminum isopropoxide;
(b) CATAPAL: Trademark of Condea Corporation for hydrated pseudoboehmite;
(c) LUDOX LS: LUDOX LS is the tradename of DuPont for an aqueous solution of 30 weight percent $SiO_2$ and 0.1 weight percent $Na_2O$;
(d) $H_3PO_4$: 85 weight percent aqueous phosphoric acid;
(e) MnAc: Manganese acetate, $Mn(C_2H_3O_2)_2.4H_2O$;
(f) TEAOH: 40 weight percent aqueous solution of tetraethylammonium hydroxide;
(g) TBAOH: 40 weight percent aqueous solution of tetrabutylammonium hydroxide;
(h) $Pr_2NH$: di-n-propylamine, $(C_3H_7)_2NH$;
(i) $Pr_3N$: tri-n-propylamine, $(C_3H_7)_3N$;
(j) Quin: Quinuclidine, $(C_7H_{13}N)$;
(k) MQuin: Methyl Quinuclidine hydroxide, $(C_7H_{13}NCH_3OH)$;
(l) C-hex: cyclohexylamine;
(m) TMAOH: tetramethylammonium hydroxide;
(n) TPAOH: tetrapropylammonium hydroxide; and
(o) DEEA: 2 diethylaminoethanol.

Preparative Procedures

MnAPSOs are prepared by forming a starting reaction mixture by adding the $H_3PO_4$ to one half of the quantity of water. This mixture is mixed and to this mixture the aluminum isopropoxide or CATAPAL is added. This mixture is then blended until a homogeneous mixture is observed. To this mixture the LUDOX LS is added and the resulting mixture blended (about 2 minutes) until a homogeneous mixture is observed. A second mixture is prepared using the manganese acetate and the remainder (about 50%) of the water. The two mixtures are admixed and the resulting mixture blended until a homogeneous mixture is observed. The organic templating agent is then added to the resulting mixture and the resulting mixture blended until a homogeneous mixture is observed, i.e., about 2 to 4 minutes. (The pH of the mixture is measured and adjusted for temperature). The mixture is then placed in a lined (polytetrafluoroethylene) stainless steel pressure vessel and digested at a temperature (150° C. or 200° C.) for a time or placed in lined screw top bottles for digestion at 100° C. Digestions are typically carried out at the autogenous pressure.

CoAPSO MOLECULAR SIEVES

The CoAPSO molecular sieves of U.S. Ser. No. 600,174, filed Apr. 13, 1984 have three-dimensional microporous framework structures of $CoO_2^{-2}$, $AlO_2^{-}$, $PO_2^{+}$ and $SiO_2$ tetrahedral units and have an empirical chemical composition on an anhydrous basis expressed by the formula:

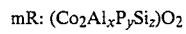

$$mR: (Co_2Al_xP_ySi_z)O_2$$

wherein "R" represents at least one organic templating agent present in the intracrystalline pore system; "m" represents the molar amount of "R" present per mole of $(Co_2Al_xP_ySi_z)O_2$ and has a value of from zero a 0.3; and "w", "x", "y" and "z" represent the mole fractions of cobalt, aluminum, phosphorus and silicon, respectively, present as tetrahedral oxides, where the mole fractions "w", "x", "y" and "z" are each at least 0.01 and are generally defined, as being within the limiting compositional values or points as follows:

| Point | Mole Fraction | | |
|---|---|---|---|
| | x | y | (z + w) |
| A | 0.60 | 0.38 | 0.02 |
| B | 0.38 | 0.60 | 0.02 |
| C | 0.01 | 0.60 | 0.39 |
| D | 0.01 | 0.01 | 0.98 |
| E | 0.60 | 0.01 | 0.39 |

In a preferred subclass of the CoAPSO molecular sieves the values of "w", "x", "y" and "z" in the above formula are within the limiting compositional values or points as follows:

| Point | Mole Fraction | | |
|---|---|---|---|
| | x | y | (z + w) |
| a | 0.55 | 0.43 | 0.02 |
| b | 0.43 | 0.55 | 0.02 |
| c | 0.10 | 0.55 | 0.35 |
| d | 0.55 | 0.10 | 0.35 |

CoAPSO compositions are generally synthesized by hydrothermal crystallization from a reaction mixture containing reactive sources of cobalt, silicon, aluminum and phosphorus, an organic templating, i.e., structure directing, agent, preferably a compound of an element of Group VA of the Periodic Table, and optionally an alkali metal. The reaction mixture is generally placed in a sealed pressure vessel, preferably lined with an inert plastic material such as polytetrafluoroethylene and heated, preferably under autogenous pressure at an effective temperature which is generally between 50° C. and 250° C. and preferably between 100° C. and 200° C. until crystals of the CoAPSO product are obtained, usually for an effective time of from several hours to several weeks. Generally the effective crystallization time will be from about 2 hours to about 30 days and typically from about 4 hours to about 20 days. The product is recovered by any convenient method such as centrifugation or filtration.

In synthesizing the CoAPSO, it is preferred to employ a reaction mixture composition expressed in terms of the molar ratios as follows:

$$aR: (Co_wAl_xP_ySi_z)O_2: bH_2O$$

wherein "R" is an organic templating agent; "a" is the amount of organic templating agent "R" and has a value of from zero to about 6 and is preferably an effective amount within the range of greater than zero (0) to about 6; "b" has a value of from zero (0) to about 500, preferably between about 2 and 300; and "w", "x", "y" and "z" represent the mole fractions of cobalt, aluminum, phosphorus and silicon, respectively, and each has a value of at least 0.01. In a preferred embodiment the reaction mixture is selected such that the mole fractions "w", "x", "y" and "z" are generally defined as being within the limiting compositional values or points as follows:

| Point | Mole Fraction | | |
|---|---|---|---|
| | x | y | (z + w) |
| F | 0.60 | 0.38 | 0.02 |
| G | 0.38 | 0.60 | 0.02 |
| H | 0.01 | 0.60 | 0.39 |
| I | 0.01 | 0.01 | 0.98 |
| J | 0.60 | 0.01 | 0.39 |

In the foregoing expression of the reaction composition, the reactants are normalized with respect to the total of "w", "x", "y" and "z" such that (w+x+y+z)=1.00 mole. Molecular sieves containing cobalt, aluminum, phosphorus and silicon as framework tetrahedral oxide units are prepared as follows:

Preparative Reagents

CoAPSO compositions may be prepared using numerous reagents. Reagents which may be employed to prepare CoAPSOs include:
(a) Alipro: aluminum isopropoxide;
(b) CATAPAL: Trademark of Condea Corporation for pseudoboehmite;
(c) LUDOX LS: Trademark of DuPont for an aqueous solution of 30 weight percent $SiO_2$ and 0.1 weight percent $Na_2O$;
(d) $Co(Ac)_2$: cobalt acetate, $Co(C_2H_3O_2)_2.4H_2O$;
(e) $CoSO_4$: cobalt sulfate, $(CoSO_4.7H_2O)$;
(f) $H_3PO_4$: 85 weight percent phosphoric acid in water;
(g) TBAOH: tetrabutylammonium hydroxide (25 wt % in methanol);
(h) $Pr_2NH$: di n propylamine, $(C_3H_7)_2NH$;
(i) $Pr_3N$: tri n-propylamine, $(C_3H_7)_3N$;
(j) Quin: Quinuclidine $(C_7H_{13}N)$;
(k) MQuin: Methyl Quinuclidine hydroxide, $(C_7H_{13}NCH_3OH)$:
(l) C-hex: cyclohexylamine;
(m) TEAOH: tetraethylammonium hydroxide (40 wt. % in water);
(n) DEEA: diethanolamine;
(o) TPAOH: tetrapropylammonium hydroxide (40 wt. % in water); and
(p) TMAOH: tetramethylammonium hydroxide (40 wt. % in water).

Preparative Procedure

CoAPSO compositions may be prepared by preparing reaction mixtures having a molar composition expressed as:

$$eR:fCoO:hAl_2O_3:iP_2O_5:gSiO_2:jH_2O$$

wherein e, f, h, i, g and j represent the moles of template R, cobalt (expressed as the oxide), $Al_2O_3$, $P_2O_5$ ($H_3PO_4$ expressed as $P_2O_5$), $SiO_2$ and $H_2O$, respectively.

The reaction mixtures are prepared by forming a starting reaction mixture comprising the $H_3PO_4$ and one half of the water. This mixture is stirred and the aluminum source (Alipro or CATAPAL) added. The resulting mixture is blended until a homogeneous mixture is observed. The LUDOX-LS is then added to the resulting mixture and the new mixture blended until a homogeneous mixture is observed. The cobalt source (e.g., $Co(Ac)_2$, $Co(SO_4)$ or mixtures thereof) is dissolved in the remaining water and combined with the first mixture. The combined mixture is blended until a homogeneous mixture is observed. The organic templating agent is added to this mixture and blended for about two to four minutes until a homogeneous mixture is observed. The resulting mixture (final reaction mixture) is placed in a lined (polytetrafluoroethylene) stainless steel pressure vessel and digested at a temperature (150° C., 200° C. or 225° C.) for a time. Digestions are typically carried out at the autogenous pressure. The products are removed from the reaction vessel and cooled.

ZnAPSO MOLECULAR SIEVES

The ZnAPSO molecular sieves of U.S. Ser. No. 600,170, filed Apr. 13, 1984 comprise framework structures of $ZnO_2^{-2}$, $AlO_2^-$, $PO_2^+$ $SiO_2$ tetrahedral units having an empirical chemical composition on an anhydrous basis expressed by the formula:

$$mR: (Zn_wAl_xP_ySi_z)O_2$$

wherein "R" represents at least one organic templating agent present in the intracrystalline pore system; "m" represents the molar amount of "R" present per mole of $(Zn_wAl_xP_ySi_z)O_2$ and has a value of zero to about 0.3; and "w", "x", "y" and "z" represent the mole fractions of zinc, aluminum, phosphorus and silicon, respectively, present as tetrahedral oxides and each has a value of at least 0.01. The mole fractions "w", "x", "y" and "z" are generally defined being within the limiting compositional values or points as follows:

| Point | Mole Fraction | | |
|---|---|---|---|
| | x | y | (z + w) |
| A | 0.60 | 0.38 | 0.02 |
| B | 0.38 | 0.60 | 0.02 |
| C | 0.01 | 0.60 | 0.39 |
| D | 0.01 | 0.01 | 0.98 |
| E | 0.60 | 0.01 | 0.39 |

In a preferred subclass of ZnAPSO molecular sieves the values "w", "x", "y" and "z" in the above formula are within the limiting compositional values or points as follows:

| Point | Mole Fraction | | |
|---|---|---|---|
| | x | y | (z + w) |
| a | 0.55 | 0.43 | 0.02 |
| b | 0.43 | 0.55 | 0.02 |
| c | 0.10 | 0.55 | 0.35 |
| d | 0.55 | 0.10 | 0.35 |

ZnAPSO compositions are generally synthesized by hydrothermal crystallization at effective process conditions from a reaction mixture containing active sources of zinc, silicon, aluminum and phosphorus, preferably an organic templating, i.e., structure directing, agent, preferably a compound of an element or Group VA of the Periodic Table, and/or optionally an alkali or other metal. The reaction mixture is generally placed in a sealed pressure vessel, preferably lined with an inert plastic material such as polytetrafluoroethylene and heated, preferably under autogenous pressure, at a temperature between 50° C. and 250° C., and preferably between 100° C. and 200° C. until crystals of the ZnAPSO product are obtained, usually a period of from several hours to several weeks. Generally the effective crystallization period is from about 2 hours to about 30 days with typical periods of from about 4 hours to about 20 days being employed to obtain ZnAPSO products. The product is recovered by any convenient method such as centrifugation or filtration.

In synthesizing the ZnAPSO compositions, it is preferred to employ a reaction mixture composition expressed in terms of the molar ratios as follows:

aR: $(Zn_wAl_xP_ySi_z)O_2$: $bH_2O$ wherein "R" is an organic templating agent; "a" is the amount of organic templating agent "R" and has a value of from zero to about 6 and is preferably an effective amount within the range of greater than zero (0) to about 6; "b" has a value of from zero (0) to about 500, more preferably between about 2 and about 300; and "w", "x", "y" and "z" represent the mole fractions of zinc, aluminum, phosphorus and silicon, respectively, and each has a value of at least 0.01. In a preferred embodiment the reaction mixture is selected such that the mole fractions "w", "x", "y" and "z" are generally defined as being within the limiting compositional values or points as follows:

| Point | Mole Fraction | | |
|---|---|---|---|
| | x | y | (z + w) |
| F | 0.60 | 0.38 | 0.02 |
| G | 0.38 | 0.60 | 0.02 |
| H | 0.01 | 0.60 | 0.39 |
| I | 0.01 | 0.01 | 0.98 |
| J | 0.60 | 0.01 | 0.39 |

In the foregoing expression of the reaction composition, the reactants are normalized with respect to the total of "w", "x", "y" and "z" such that (w+x+y+z)=1.00 mole. Molecular sieves containing zinc, aluminum, phosphorus and silicon as framework tetrahedral oxide units are prepared as follows:

Preparative Reagents

ZnAPSO compositions are typically prepared using numerous reagents. Reagents which may be employed to prepare ZnAPSOs include:

(a) Alipro: aluminum isopropoxide;
(b) LUDOX LS: LUDOX LS is the trade name of DuPont for an aqueous solution of 30 weight percent $SiO_2$ and 0.1 weight percent $Na_2O$;
(c) CATAPAL: Trademark of Condea Corporation for hydrated pseudoboehmite;
(d) $H_3PO_4$: 85 weight percent aqueous phosphoric acid;
(e) ZnAc: Zinc Acetate, $Zn(C_2H_3O_2)_2.4H_2O$;
(f) TEAOH: 40 weight percent aqueous solution of tetraethylammonium hydroxide;
(g) TBAOH: 40 weight percent aqueous solution of tetrabutylammonium hydroxide;
(h) TMAOH: Tetramethylammonium hydroxide pentahydrate, $(CH_3)_4NOH.5H_2O$;
(i) TPAOH: 40 weight percent aqueous solution of tetrapropylammonium hydroxide, $(C_3H_7)_4NOH$;
(j) $Pr_2NH$: Di-n-propylamine, $(C_3H_7)_2NH$;
(k) $Pr_3N$: Tri-n propylamine, $(C_3H_7)_3N$;
(l) Quin: Quinuclidine, $(C_7H_{13}N)$;
(m) C hex: cyclohexylamine; and
(n) DEEA: diethylethanolamine, $(C_2H_5)_2NC_2H_5OH$.

Preparative Procedure

ZnAPSO compositions are typically prepared by forming reaction mixtures having a molar composition expressed as:

$eR:fZnO:gAl_2O_3:hP_2O_5:iSiO_2:jH_2O$ wherein e, f, g, h, i and j represent the moles of template R, zinc (expressed as the oxide), $Al_2O_3$, $P_2O_5$ ($H_3PO_4$ expressed as $P_2O_5$), $SiO_2$ and $H_2O$, respectively.

The reaction mixtures are generally prepared by forming a starting reaction mixture comprising the $H_3PO_4$ and a portion of the water. This mixture is stirred and the aluminum source added. The resulting mixture is blended until a homogeneous mixture is observed. The LUDOX LS is then added to the resulting mixture and the new mixture blended until a homogeneous mixture is observed. The zinc source (zinc acetate) is dissolved in the remaining water and combined with the first mixture. The combined mixture is blended until a homogeneous mixture is observed. The organic templating agent is added to this mixture and blended for about two to four minutes until a homogeneous mixture is observed. The resulting mixture (final reaction mixture) is placed in a lined (polytetrafluoroethylene) stainless steel pressure vessel and digested at an effective temperature for an effective time. Digestions are typically carried out under autogenous pressure. The products are removed from the reaction vessel and cooled.

FeAPSO MOLECULAR SIEVES

The FeAPSO molecular sieves of U.S. Ser. No. 600,173, filed Apr. 13, 1984 (now U.S. Pat. No. 4,683,217) have three-dimensional microporous crystal framework structures of $FeO_2^{-2}$, (and or $FeO_2^-$), $AlO_2^-$, $PO_2^+$ and $SiO_2$ tetrahedral oxide units and having a unit empirical formula, on an anhydrous basis, of:

$mR: (Fe_2Al_xP_ySi_z)O_2$ wherein "R" represents at least one organic templating agent present in the intracrystalline pore system; "m" represents the moles of "R" present per mole of $(Fe_wAl_xP_ySi_z)O_2$ and has a value of from zero (0) to about 0.3; the maximum value of "m" in each case depends upon the molecular dimensions of the templating agent and the available void volume of the pore system of the particular molecular sieve involved; and "w", "x", "y" and "z" represent the mole fractions of iron, aluminum, phosphorus and silicon, respectively, present as tetrahedral oxides, said mole fractions being such that they are within the limiting compositional values or points as follows:

| Point | Mole Fraction | | |
|---|---|---|---|
| | x | y | (z + w) |
| A | 0.60 | 0.38 | 0.02 |
| B | 0.38 | 0.60 | 0.02 |
| C | 0.01 | 0.60 | 0.39 |
| D | 0.01 | 0.01 | 0.98 |
| E | 0.60 | 0.01 | 0.39 |

The values of w, x, y and z may be as follows:

| Point | Mole Fraction | | |
|---|---|---|---|
| | x | y | (z + w) |
| a | 0.55 | 0.43 | 0.02 |
| b | 0.43 | 0.55 | 0.02 |
| c | 0.10 | 0.55 | 0.35 |
| d | 0.55 | 0.10 | 0.35 |

The FeAPSOs of the instant invention are generally synthesized by hydrothermal crystallization from a reaction mixture comprising reactive sources of iron, aluminum, phosphorus and silicon, and preferably one or more organic templating agents. Optionally, alkali or other metal(s) may be present in the reaction mixture and may act as templating agents. The reaction mixture is generally placed in a pressure vessel, preferably lines wiht an inert plastic material, such as polytetrafluoroethylene, and heated, preferably under autogenous pressure, at an effective temperature which is generally between about 50° C. and about 250° C., and preferably between about 100° C. and 200° C., until crystals of the FeAPSO product are obtained, usually a period of from several hours to several weeks. Molecular sieves containing iron, aluminum, phosphorus and silicon as framework tetrahedral oxide units are typically prepared as follows:

Preparative Reagents

FeAPSO compositions may be prepared using numerous reagents. Reagents which may be employed to prepare FeAPSOs include:

(a) Alipro: aluminum isopropoxide Al(OCH(CH$_3$)$_2$)hd 3;
(b) LUDOX-LS: LUDOX LS is the trademark of Du-Pont for an aqueous solution of 30 weight percent SiO$_2$ and 0.1 weight percent Na$_2$O;
(c) CATAPAL: trademark for hydrated aluminum oxide containing about 75 wt. percent Al$_2$O$_3$ (pseudoboehmite phase) and about 25 wt. percent water;
(d) Fe(Ac)$_2$: Iron (II) acetate;
(e) FeSO$_4$: Iron (II) sulfate hexahydrate;
(f) H$_3$PO$_4$: 85 weight percent phosphoric acid in water;
(g) TEAOH: 40 weight percent aqueous solution of tetraethylammonium hydroxide;
(h) TBAOH: 40 weight percent aqueous solution of tetrabutylammonium hydroxide;
(i) Pr$_2$NH: di-n-propylamine, ((C$_3$H$_7$)$_2$NH);
(j) Pr$_3$N: tri n propylamine, ((C$_3$H$_7$($_3$N);
(k) Quin: Quinuclidine (C
(l) MQuin: Methyl Quinuclidine hydroxide (C$_7$H$_{13}$NCH$_3$OH);
(m) TMAOH: tetramethylammonium hydroxide pentahydrate, and
(n) C-hex: cyclohexylamine.

Preparative Procedures (a) Reaction mixtures to prepare FeAPSOs are typically prepared by grinding an aluminum isopropoxide in a blender followed by slowly adding a H$_3$PO$_4$ solution with mixing. A solution/dispersion of iron acetate in water is added and then a silica (e.g., LUDOX-LS) is added. The organic templating agent is then added to this mixture, or in some cases one-half of this mixture, and the mixture blended to form a homogeneous mixture. For example, in one embodiment, the number of moles of each component in the reaction mixture is as follows:

| Component | Moles |
|---|---|
| Al$_2$O$_3$ | 0.9 |
| P$_2$O$_5$ | 0.9 |
| SiO$_2$ | 0.2 |
| FeO* | 0.2 |
| TEAOH | 1.0 |
| H$_2$O | 50 |

*Iron (II) acetate reported as Iron (II) oxide.

The reaction mixture is sealed in a stainless steel pressure vessel lined with polytetrafluoroethylene and heated in an oven at a temperature, time and under autogenous pressure. The solid reaction product is recovered by filtration, washed with water and dried at room temperature.

(b) In another embodiment, reaction mixtures are prepared by grinding the aluminum isopropoxide in a blender followed by addition of a solution/dispersion of iron (II) acetate. H$_3$PO$_4$ is added to this mixture and the resulting mixture blended to form a homogeneous mixture. A silica (e.g., LUDOX-LS) is added to this mixture except that in some instances the silica may be added with the H$_3$PO$_4$. The resulting mixtures were blended until a homogeneous mixture is observed. Organic templating agent is added to each mixture and the resulting mixtures placed in a stainless steel pressure vessel lined with polytetrafluoroethylene and heated, washed and the product recovered. In this embodiment the number of moles of each component in the reaction mixture is as follows:

| Component | Moles |
|---|---|
| Al$_2$O$_3$ | 0.9 |
| P$_2$O$_5$ | 0.9 |
| SiO$_2$ | 0.2 |
| FeO* | 0.2 |
| Template | 1.0 |
| H$_2$O | 50 |

*Iron (II) acetate reported as Iron (II) oxide.

QUINARY MOLECULAR SIEVES

The QuinAPSO quinary molecular sieves of U.S. Ser. Nos. 600,168 and 600,181, both filed Apr. 13, 1984, have three dimensional microporous framework structures of MO$_2^n$, AlO$_2^-$, PO$_2^+$ and SiO$_2$ tetrahedral units, where "n" is −3, −2, −1, 0, or +1, an empirical chemical composition on an anhydrous basis expressed by the formula:

$$mR: (M_wAl_xP_ySi_z)O_2$$

wherein "R" represents at least one organic templating agent present in the intracrystalline pore system; "m" represents the molar amount of "R" present per mole of $(M_wAl_xP_ySi_z)O_2$ and has a value of from zero (0) to about 0.3; M represents at least two elements selected from the group consisting of arsenic, beryllium, boron, chromium, cobalt, gallium, germanium, iron, lithium, magnesium, manganese, titanium, vanadium and zinc; and "w", "x", "y" and "z" represent the mole fractions of M, aluminum, phosphorus and silicon, respectively, present as tetrahedral oxides. Preferably, M represents the combination of cobalt and manganese. The mole fractions "w", "x", "y", and "z" are generally defined as being within the limiting compositional values or points as follows:

| Point | Mole Fraction | | |
|---|---|---|---|
| | x | y | (z + w) |
| A | 0.60 | 0.37 | 0.03 |
| B | 0.37 | 0.60 | 0.03 |
| C | 0.01 | 0.60 | 0.39 |
| D | 0.01 | 0.01 | 0.98 |
| E | 0.60 | 0.01 | 0.39 |

Preferably the mole fractions w, x, y and z will fall within the limiting compositional values or points as follows:

| Point | Mole Fraction | | |
|---|---|---|---|
| | x | y | (z + w) |
| a | 0.60 | 0.37 | 0.03 |
| b | 0.37 | 0.60 | 0.03 |
| c | 0.01 | 0.60 | 0.39 |
| d | 0.01 | 0.39 | 0.60 |
| e | 0.39 | 0.01 | 0.60 |
| f | 0.60 | 0.01 | 0.39 |

QuinAPSO compositions are generally synthesized by hydrothermal crystallization from a reaction mixture containing reactive sources of the elements M, aluminum, phosphorus and silicon and preferably an organic templating agent, i.e., structure-directing, agent. The structure-directing agents are preferably a compound of an element of Group VA of the Periodic Table, and may be an alkali or other metal. The reaction mixture is generally placed in a sealed pressure vessel, preferably lined with an inert plastic material such as polytetrafluoroethylene and heated, preferably under autogenous pressure and at typical effective temperatures between 50° C. and 250° C., preferably between 100° C. and 200° C., until crystals of the QuinAPSO product are obtained, usually over a period of from several hours to several weeks. Typical effective crystallization times are from about 2 hours to 30 days with from about 4 hours to about 20 days being generally employed to obtain QuinAPSO products. The product is recovered by any convenient method such as centrifugation or filtration.

In synthesizing the QuinAPSO compositions, it is preferred to employ a reaction mixture composition expressed in terms of the molar ratios as follows:

$$aR: (M_wAl_xP_ySi_z)O_2bH_2O$$

wherein "R" is an organic templating agent; "a" is the amount of organic templating agent "R" and has a value of from zero to about 6 and is preferably an effective amount within the range of greater than zero (0) to about 6; "b" has a value of from zero (0) to about 500, preferably between about 2 and about 300; and "w", "x", "y" and "z" represent the mole fractions of elements M, aluminum, phosphorus and silicon, respectively, and each has a value of at least 0.01.

In one embodiment the reaction mixture is selected such that the mole fractions "w", "x", "y" and "z" are generally defined as being within the limiting compositional values or points as follows:

| Point | Mole Fraction | | |
|---|---|---|---|
| | x | y | (z + w) |
| F | 0.60 | 0.37 | 0.03 |
| G | 0.37 | 0.60 | 0.03 |
| H | 0.01 | 0.60 | 0.39 |
| I | 0.01 | 0.01 | 0.98 |
| J | 0.60 | 0.01 | 0.39 |

In the foregoing expression of the reaction composition, the reactants are normalized with respect to the total of "w", "x", "y" and "z" such that (w+x+y+z)=1.00 mole. QuinAPSO compositions were prepared using numerous regents; the appropriate sources of the various elements M are the same as those used in the preparation of the various APO and APSO molecular sieves containing the same elements, as described in detail above and below.

Reagents which may be employed to prepare QuinAPSOs include:
(a) Alipro: aluminum isopropoxide;
(b) LUDOX-LS: LUDOX-LS is the tradename of DuPont for an aqueous solution of 30 $SiO_2$ and 0.1 weight weight percent percent of $Na_2O$;
(c) $H_3PO_4$: 85 weight percent phosphoric acid;
(d) MnAc: Manganese acetate, Mn $(C_2H_3O_2)_2.4H_2O$ (for QuinAPSOs containing manganese);
(e) CoAc: Cobalt Acetate, $Co(C_2H_3O_2)_2.4H_2O$ (for QuinAPSOs containing cobalt);
(f) TEAOH: 40 weight percent aqueous solution of tetraethylammonium hydroxide; and
(g) $Pr_2NH$: di propylamine, $(C_3H_7)_2NH$.

Preparative procedures

QuinAPSOs may be prepared by forming a starting reaction mixture by adding $H_3PO_4$ and one half of the quantity of water. To this mixture an aluminum isopropoxide is added. This mixture is then blended until a homogeneous mixture is observed. To this mixture a silica (e.g., LUDOX-LS) is added and the resulting mixture blended (about 2 minutes) until a homogeneous mixture is observed. A second mixture is prepared using manganese acetate (or a appropriate source of another element M) and one half of the remaining water. A third mixture is prepared using cobalt acetate (or a appropriate source of another element M) and one half of the remaining water. The three mixtures are admixed and the resulting mixture blended until a homogeneous mixture is observed. The organic templating agent is then added to the resulting mixture and the resulting mixture blended until homogeneous mixture is observed, i.e., about 2 to 4 minutes. The $pH_3PO_4$ of the mixture is then placed in a lined (polytetrafluoroethylene) stainless steel pressure vessel and digested at an effective temperature for an effective time. Digestions are typically carried out under autogeneous pressure.

CoMnMgAPSO MOLECULAR SIEVES

The CoMnMgAPSO senary molecular sieves of U.S. Ser. No. 600,182, filed Apr. 13, 1984, and three dimensional microporous framework structures of $CoO_2^{-2}$, $MnO_2^{-2}$, $AlO_2$, $PO_2$ and $SiO_2$ tetrahedral oxide units having an empirical chemical composition on an anhydrous basis expressed by the formula:

$$mR : (Co_tMn_uMg_vAl_xP_ySi_z)O_2$$

wherein "R" represents at least one organic templating agent present in the intracrystalline pore system; "m" represents the molar amount of "R" present per mole of $(Co_tMn_uMg_vAl_xP_ySi_z)O_2$ and has a value of from zero (0) to about 0.3; "t", "u", "v", "x", "y" and "z" represent the mole fractions of cobalt, manganese, magnesium, aluminum, phosphorus and silicon, respectively, present as tetrahedral oxides and each has a value of at least 0.01. The mole fractions "w", "x", "y" and "z", where "w" is the sum of "t"+"u"+"v", are generally defined as being within the limiting compositional values or points as follows:

| Point | Mole Fraction | | |
|---|---|---|---|
| | x | y | (z + w) |
| A | 0.60 | 0.36 | 0.04 |
| B | 0.36 | 0.60 | 0.04 |
| C | 0.01 | 0.60 | 0.39 |
| D | 0.01 | 0.01 | 0.98 |
| E | 0.60 | 0.01 | 0.39 |

In a preferred subclass of the CoMnMgAPSO molecular sieves the values of "w", "x", "y" and "z" in the above formula are within the limiting compositional values or points as follows:

| Point | Mole Fraction | | |
|---|---|---|---|
| | x | y | (z + w) |
| a | 0.55 | 0.41 | 0.04 |
| b | 0.41 | 0.55 | 0.04 |
| c | 0.10 | 0.55 | 0.35 |
| d | 0.55 | 0.10 | 0.35 |

CoMnMgAPSO compositions are generally synthesized by hydrothermal crystallization from a reaction mixture containing reactive sources of cobalt, manganese, magnesium, aluminum, phosphorus and silicon, and preferably an organic templating agent, i.e., structure directing agent. The structure directing agents are preferably a compound of an element of Group VA of the Periodic Table, and/or optionally an alkali or other metal. The reaction mixture is generally placed in a sealed pressure vessel, preferably lined with an inert plastic material such as polytetrafluoroethylene and heated, preferably under autogenous pressure at a temperature between 50° C. and 250° C., and preferably between 100° C. and 200° C., until crystals of the CoMnMgAPSO product are obtained, usually over a period of from several hours to several weeks. Typical crystallization times are from about 2 hours to about 30 days with from about 4 hours to about 20 days generally being employed to obtain CoMnMgAPSO products. The product is recovered by any convenient method such as centrifugation or filtration.

In synthesizing the CoMnMgAPSO compositions, it is preferred to employ a reaction mixture composition expressed in terms of the molar ratios as follows:

$$aR: (Co_tMn_uMg_vAl_xP_ySi_z)O_2:bH_2O$$

wherein "R" is an organic templating agent; "a" is the amount of organic templating agent "R" and has a value of from zero to about 6 and is preferably an effective amount within the range of greater than zero (0) to about 6 and more preferably from greater than zero to about 2; "b" has a value of from zero (0) to about 500, preferably between about 2 and about 300; and "t", "u", "v", "x", "y", and "z" represent the mole fractions of cobalt, manganese, magnesium, aluminum, phosphorus and silicon, respectively, and each has a value of at least 0.01.

In a preferred embodiment the reaction mixture is selected such that the mole fractions "w", "x", "y" and "z", where "w" is the sum of "t"+"u"+"v", are generally defined as being within the limiting compositional values or points as follows:

| Point | Mole Fraction | | |
|---|---|---|---|
| | x | y | (z + w) |
| F | 0.60 | 0.36 | 0.04 |
| G | 0.36 | 0.60 | 0.04 |
| H | 0.01 | 0.60 | 0.39 |
| I | 0.01 | 0.01 | 0.98 |
| J | 0.60 | 0.01 | 0.39 |

In the foregoing expression of the reaction composition, the reactants are normalized with respect to the total of "t", "u", "v", "x", "y" and "z" such that $(t+u+v+x+y+z)=1.00$ mole. Molecular sieves containing cobalt, manganese, magnesium, aluminum, phosphorus and silicon as framework tetrahedral oxide units are prepared as follows:

Preparative Reagents

CoMnMgAPSO compositions may be prepared by using numerous reagents. Reagents which may be employed to prepare CoMnMgAPSOs include:
(a) Alipro: aluminum isopropoxide;
(b) LUDOX-LS: LUDOX-LS is the tradename of DuPont for an aqueous solution of 30 weight percent $SiO_2$ and 0.1 weight percent $Na_2O$;
(c) $H_3PO_4$: aqueous solution which is 85 weight percent phosphoric acid;
(d) MnAc: Manganese acetate, $Mn(C_2H_3O_2)_2.4H_2O$;
(e) CoAc: Cobalt Acetate, $Co(C_2H_3O_2)_2.4H_2O$;
(f) MgAc: Magnesium Acetate $Mg(C_2H_3O_2).4H_2O$;
(g) TEAOH: 40 weight percent aqueous solution of tetraethylammonium hydroxide; and
(h) $Pr_2NH$: di-n-propylamine, $(C_3H_7)_2NH$.

Preparative Procedures

CoMnMgAPSOs may be prepared by forming a starting reaction mixture by adding $H_3PO_4$ and one half of the quantity of water. To this mixture an aluminum isopropoxide is added. This mixture is then blended until a homogeneous mixture is observed. To this mixture a silica (e.g., LUDOX-LS) is added and the resulting mixture blended (about 2 minutes) until a homogeneous mixture is observed.

Three additional mixtures are prepared using cobalt acetate, magnesium acetate and manganese acetate using one third of the remainder of the water for each mixture. The four mixtures are then admixed and the resulting mixture blended until a homogeneous mixture is observed. An organic templating agent is then added to the resulting mixture and the resulting mixture blended until a homogeneous mixture is observed, i.e., about 2 to 4 minutes. The mixture is then placed in a lined (polytetrafluoroethylene) stainless steel pressure vessel and digested at a temperature for a time. Digestions are typically carried out under autogenous pressure.

SenAPSO MOLECULAR SIEVES

The SenAPSO molecular sieves of U.S. Ser. No. 600,183, filed Apr. 13, 1984 have three dimensional microporous framework structures of $MO_2^n$, $AlO_2^-$, $PO_2^+$ and $SiO_2$ tetrahedral oxide units, where "n" is $-3$, 2, 1, 0 or $+1$, and have an empirical chemical composition on an anhydrous basis expressed by the formula:

$$mR: (M_wAl_xP_ySi_z)O_2$$

wherein "R" represents at least one organic templating agent present in the intracrystalline pore system; "m" represents the molar amount of "R" present per mole of $(M_wAl_xP_ySi_z)O_2$, and has a value of from zero to about 0.3; "M" represents three elements selected from the group consisting of arsenic, beryllium, boron, chromium, cobalt, gallium, germanium, iron, lithium, magnesium, manganese, titanium, vanadium and zinc; "n" may have the aforementioned values depending upon the oxidation state of "M"; and "w", "x", "y" and "z" represent the mole fractions of elements "M", aluminum, phosphorus and silicon, respectively, present as tetrahedral oxides. The mole fractions "w", "x", "y" and "z" are generally defined as being within the limiting compositional values or points as follows, wherein "w" denotes the combined mole fractions of the three elements "M" such that "w" = "$w_1$" + "$w_2$" + "$w_3$" and each element "M" has a mole fraction of at least 0.01:

| Point | Mole Fraction | | |
|---|---|---|---|
| | x | y | (z + w) |
| A | 0.60 | 0.36 | 0.04 |
| B | 0.36 | 0.60 | 0.04 |
| C | 0.01 | 0.60 | 0.39 |
| D | 0.01 | 0.01 | 0.98 |
| E | 0.60 | 0.01 | 0.39 |

In a preferred subclass of the SenAPSO molecular sieves the values f "w", "x", "y" and "z" in the above formula are within the limiting compositional values or points as follows:

| Point | Mole Fraction | | |
|---|---|---|---|
| | x | y | (z + w) |
| a | 0.60 | 0.36 | 0.04 |
| b | 0.36 | 0.60 | 0.04 |
| c | 0.01 | 0.60 | 0.39 |
| d | 0.01 | 0.39 | 0.60 |
| e | 0.39 | 0.01 | 0.60 |
| f | 0.60 | 0.01 | 0.39 |

SenAPSO compositions are generally synthesized by hydrothermal crystallization from a reaction mixture containing reactive sources of elements "M", aluminum, phosphorus and silicon, and preferably an organic templating, i.e., structure directing, agent. The structure directing agents are preferably a compound of an element of Group VA of the Periodic Table, and/or optionally an alkali or other metal. The reaction mixture is generally placed in a sealed pressure vessel, preferably lined with an inert plastic material such as polytetrafluoroethylene and heated, preferably under autogenous pressure at a temperature between 50° C. and 250° C., and preferably between 100° C. and 200° C., until crystals of the SenAPSO product are obtained, usually over a period of from several hours to several weeks. Typical crystallization times are from about 2 hours to about 30 days with from about 4 hours to about 20 days generally being employed to obtain SenAPSO products. The product is recovered by any convenient method such as centrifugation or filtration.

In synthesizing the SenAPSO compositions, it is preferred to employ a reaction mixture composition expressed in terms of the molar ratios as follows:

$$aR: (M_wAl_xP_ySi_z)O_2: bH_2O$$

wherein "R" is an organic templating agent; "a" is the amount of organic templating agent "R" and has a value of from zero to about 6 and is preferably an effective amount within the range of greater than zero (0) to about 6 and more preferably from greater than zero to about 2; "b" has a value of from zero (0) to about 500, preferably between about 2 and about 300; and "w", "x", "y", and "z" represent the mole fractions of elements "M", aluminum, phosphorus and silicon, respectively, and each has a value of at least 0.01, with the proviso that each "M" is present in a mole fraction of at least 0.01.

In a preferred embodiment the reaction mixture is selected such that the mole fractions "w", "x", "y" and "z" are generally defined as being within the limiting compositional values or points as follows:

| Point | Mole Fraction | | |
|---|---|---|---|
| | x | y | (z + w) |
| F | 0.60 | 0.36 | 0.04 |
| G | 0.36 | 0.60 | 0.04 |
| H | 0.01 | 0.60 | 0.39 |
| I | 0.01 | 0.01 | 0.98 |
| J | 0.60 | 0.01 | 0.39 |

In the foregoing expression of the reaction composition, the reactants are normalized with respect to the total of "w", "x", "y" and "z" such that (w+x+y+z)=1.00 mole. The SenAPSO molecular sieves are prepared by preparative techniques, and using sources of the elements "M" similar to those described for the other APSO molecular sieves described above and below.

AsAPSO MOLECULAR SIEVES

The AsAPSO molecular sieves of U.S. Ser. No. 599,808, filed Apr. 13, 1984, and U.S. Ser. No. 845,484 filed Mar. 31, 1986 have a framework structure of $AsO_2^n$, $AlO_2^-$, $PO_2^+$ and $SiO_2$ tetrahedral units having an empirical chemical composition on an anhydrous basis expressed by the formula:

$$mR: (As_wAl_xP_ySi_z)O_2$$

wherein "R" represents at least one organic templating agent present in the intracrystalline pore system; "m" represents the molar amount of "R" present per mole of $(As_wAl_xP_ySi_z)O_2$ and has a value of zero to abou 0.3, but is preferably not greater than 0.15; and "w", "x", "y" and "z" represent the mole fractions of the elements arsenic, aluminum, phosphorus and silicon, respectively, present as tetrahedral oxides. The mole fractions "w", "x", "y" and "z" are generally defined as being within the limiting compositional values or points as follows:

| Point | Mole Fraction | | |
|---|---|---|---|
| | x | y | (z + w) |
| A | 0.60 | 0.38 | 0.02 |
| B | 0.38 | 0.60 | 0.02 |
| C | 0.01 | 0.60 | 0.39 |
| D | 0.01 | 0.01 | 0.98 |
| E | 0.60 | 0.01 | 0.39 |

In a preferred subclass of the AsAPSO molecular sieves, the values of w, x, y and z are as follows:

| Point | Mole Fraction | | |
|---|---|---|---|
| | x | y | (z + w) |
| a | 0.60 | 0.38 | 0.02 |
| b | 0.38 | 0.60 | 0.02 |
| c | 0.01 | 0.60 | 0.39 |
| d | 0.01 | 0.39 | 0.60 |
| e | 0.39 | 0.01 | 0.60 |
| f | 0.60 | 0.01 | 0.39 |

In an especially preferred subclass of the AsAPSO molecular sieves, the values of w, x, y and z are as follows:

| Point | Mole Fraction | | |
|---|---|---|---|
| | x | y | (z + w) |
| g | 0.50 | 0.40 | 0.10 |
| h | 0.42 | 0.48 | 0.10 |
| i | 0.38 | 0.48 | 0.14 |
| j | 0.38 | 0.37 | 0.25 |
| k | 0.45 | 0.30 | 0.25 |
| l | 0.50 | 0.30 | 0.20 |

AsAPSO compositions are generally synthesized by hydrothermal crystallization from a reaction mixture containing reactive sources of arsenic, silicon, aluminum and phosphorus, preferably an organic templating, i.e., structure-directing, agent, preferably a compound of an element of Group VA of the Periodic Table, and/or optionally an alkali or other metal. The reaction mixture is generally placed in a sealed pressure vessel, preferably lined with an inert plastic material such as polytetrafluoroethylene and heated, preferably under autogenous pressure at a temperature between about 50° C. and about 250° C., and preferably between about 100° C. and about 200° C. until crystals of the AsAPSO product are obtained, usually a period of from several hours to several weeks. Typical effective times of from 2 hours to about 30 days, generally from about 12 hours to about 10 days, have been observed. The product is recovered by any convenient method such as centrifugation or filtration.

In synthesizing the AsAPSO compositions, it is preferred to employ a reaction mixture composition expressed in terms of the molar ratios as follows:

$aR: (As_w Al_x P_y Si_z)P_2: bH_2O$ wherein "R" is an organic templating agent; "a" is the amount of organic templating agent "R" and has a value of from zero to about 6 and is preferably an effective amount within the range of greater than zero (0) to about 6, and most preferably not more than about 1.0; "b" has a value of from zero (0) to about 500, preferably between about 2 and about 300, most preferably not greater than about 60; and "w", "x", "y" and "z" represent the mole fractions of arsenic, aluminum, phosphorus and silicon, respectively, and each has a value of at least 0.01.

In one embodiment the reaction mixture is selected such that the mole fractions "w", "x", "y" and "z" are generally defined as being within the limiting compositional values or points as follows:

| Point | Mole Fraction | | |
|---|---|---|---|
| | x | y | (z + w) |
| F | 0.60 | 0.38 | 0.02 |
| G | 0.38 | 0.60 | 0.02 |
| H | 0.01 | 0.60 | 0.39 |
| I | 0.01 | 0.01 | 0.98 |
| J | 0.60 | 0.01 | 0.39 |

Especially preferred reaction mixtures are those containing from about 1 to about 2 total moles of silicon and arsenic, and from about 1 to about 2 moles of aluminum, per mole of phosphorus.

In the foregoing expression of the reaction composition, the reactants are normalized with respect to the total of "w", "x", "y" and "z" such that $(w+x+y+z)=1.00$ mole. Molecular sieves containing arsenic, aluminum, phosphorus and silicon as framework tetrahedral oxide units are prepared as follows:

Preparative Reagents

AsAPSO compositions may be prepared by using numerous reagents. Reagents which may be employed to prepare AsAPSOs include:

(a) Alipro: aluminum isopropoxide;
(b) CATAPAL: Trademark of Condea Corporation for hydrated pseudoboehmite;
(c) LUDOX-LS: LUDOX-LS is the tradename of Dupont for an aqueous solution of 30 weight percent $SiO_2$ and 0.1 weight percent $Na_2O$;
(d) $H_3PO_4$: 85 weight percent aqueous phosphoric acid;
(e) $As_2O_5$, arsenic (V) oxide;
(f) TEAOH: 40 weight percent aqueous solution of tetraethylammonium hydroxide;
(g) TBAOH: 40 weight percent aqueous solution of tetrabutylammonium hydroxide;
(h) $Pr_2NH$: di-n-propylamine, $(C_3H_7)_2NH$;
(i) $Pr_3N$: tri-n-propylamine, $(C_3H_7)_3N$;
(j) Quin: Quinuclidine, $(C_7H_{13}N)$;
(k) MQuin: Methyl Quinuclidine hydroxide, $(C_7H_{13}NCH_3OH)$;
(l) C-hex: cyclohexylamine;
(m) TMAOH: tetramethylammonium hydroxide;
(n) TPAOH: tetrapropylammonium hydroxide; and
(o) DEEA: 2-diethylaminoethanol;
(p) Tetraalkylorthosilicates, such as tetraethylorthosilicate.

Preparative Procedures

AsAPSOs may be prepared by forming a starting reaction mixture by dissolving the arsenic (V) oxide and the $H_3PO_4$ in at least part of the water. To this solution the aluminum isopropoxide or CATAPAL is added.

This mixture is then blended until a homogeneous mixture is observed. To this mixture the templating agent and then the silica is added and the resulting mixture blended until a homogeneous mixture is observed. The mixture is then placed in a lined (polytetrafluoroethylene) stainless steel pressure vessel and digested at a temperature (150° C. or 200° C.) for a time or placed in lined screw top bottles for digestion at 100° C. Digestions are typically carried out under autogenous pressure.

BAPSO MOLECULAR SIEVES

The BAPSO molecular sieves of U.S. Ser. No. 600,177, filed Apr. 13, 1984, and U.S. Ser. No. 845,255 filed Mar. 28, 1986 have a framework structure of $BO_2^-$, $AlO_2^-$, $PO_2^+$ and $SiO_2$ tetrahedral units having an empirical chemical composition on an anhydrous basis expressed by the formula:

$$mR: (B_wAl_xP_ySi_z)O_2$$

wherein "R" represents at least one organic templating agent present in the intracrystalline pore system; "m" represents the molar amount of "R" present per mole of $(B_wAl_xP_ySi_z)O_2$ and has a value of zero to about 0.3, but is preferably not greater than 0.15; and "w", "x", "y" and "z" represent the mole fractions of the elements boron, aluminum, phosphorus and silicon, respectively, present as tetrahedral oxides. The mole fractions "w", "x", "y" and "z" are generally defined as being within the limiting compositional values or points as follows:

| Point | Mole Fraction | | |
|---|---|---|---|
| | x | y | (z + w) |
| A | 0.60 | 0.38 | 0.02 |
| B | 0.38 | 0.60 | 0.02 |
| C | 0.01 | 0.60 | 0.39 |
| D | 0.01 | 0.01 | 0.98 |
| E | 0.60 | 0.01 | 0.39 |

In a preferred subclass of the BAPSO molecular sieves, the values of w, x, y and z are as follows:

| Point | Mole Fraction | | |
|---|---|---|---|
| | x | y | (z + w) |
| a | 0.60 | 0.38 | 0.02 |
| b | 0.38 | 0.60 | 0.02 |
| c | 0.01 | 0.60 | 0.39 |
| d | 0.01 | 0.39 | 0.60 |
| e | 0.39 | 0.01 | 0.60 |
| f | 0.60 | 0.01 | 0.39 |

In an especially preferred subclass of the BAPSO molecular sieves, the values of w, x, y and z are as follows:

| Point | Mole Fraction | | |
|---|---|---|---|
| | x | y | (z + w) |
| g | 0.51 | 0.42 | 0.07 |
| h | 0.45 | 0.48 | 0.07 |
| i | 0.33 | 0.48 | 0.19 |
| j | 0.33 | 0.38 | 0.29 |
| k | 0.36 | 0.35 | 0.29 |
| l | 0.51 | 0.35 | 0.14 |

BAPSO compositions are generally synthesized by hydrothermal crystallization from a reaction mixture containing reactive sources of boron, silicon, aluminum and phosphorus, preferably an organic templating, i.e., structure-directing, agent, preferably a compound of an element of Group VA of the Periodic Table, and/or optionally an alkali or other metal. The reaction mixture is generally placed in a sealed pressure vessel, preferably lined with an inert plastic material such as polytetrafluoroethylene and heated, preferably under autogenous pressure at a temperature between about 50° C. and about 250° C., and preferably between about 100° C. and about 200° C. until crystals of the BAPSO product are obtained, usually a period of from several hours to several weeks. Typical effective times of from 2 hours to about 30 days, generally from about 4 hours to about 20 days, have been observed. The product is recovered by any convenient method such as centrifugation or filtration.

In synthesizing the BAPSO compositions, it is preferred to employ a reaction mixture composition expressed in terms of the molar ratios as follows:

$$aR: (B_wAl_xP_ySi_z)O_2: bH_2O$$

wherein "R" is an organic templating agent; "a" is the amount of organic templating agent "R" and has a value of from zero to about 6 and is preferably an effective amount within the range of greater than zero (0) to about 6, and most preferably not more than about 0.5; "b" has a value of from zero (0) to about 500, preferably between about 2 and about 300, most preferably not greater than about 20; and "w", "x", "y" and "z" represent the mole fractions of boron, aluminum, phosphorus and silicon, respectively, and each has a value of at least 0.01.

In one embodiment the reaction mixture is selected such that the mole fractions "w", "x", "y" and "z" are generally defined as being within the limiting compositional values or points as follows:

| Point | Mole Fraction | | |
|---|---|---|---|
| | x | y | (z + w) |
| F | 0.60 | 0.38 | 0.02 |
| G | 0.38 | 0.60 | 0.02 |
| H | 0.01 | 0.60 | 0.39 |
| I | 0.01 | 0.01 | 0.98 |
| J | 0.60 | 0.01 | 0.39 |

Especially preferred reaction mixtures are those containing from about 1.0 to about 2 total moles of silicon and boron, and from about 0.75 to about 1.25 moles of aluminum, per mole of phosphorus.

In the foregoing expression of the reaction composition, the reactants are normalized with respect to the total of "w", "x", "y" and "z" such that (w+x+y+z)=1.00 mole. Molecular sieves containing boron, aluminum, phosphorus and silicon as framework tetrahedral oxide units are prepared as follows:

Preparative Reagents

BAPSO compositions may be prepared by using numerous reagents. Reagents which may be employed to prepare BAPSOs include:
(a) Alipro: aluminum isopropoxide;
(b) CATAPAL: Trademark of Condea Corporation for hydrated pseudoboehmite;
(c) LUDOX-LS: LUDOX-LS is the tradename of DuPont for an aqueous solution of 30 weight percent $SiO_2$ and 0.1 weight percent $Na_2O$;

(d) H₃PO₄: 85 weight percent aqueous phosphoric acid;
(e) H₃BO₃, boric acid, and trialkyl borates;
(f) TEAOH: 40 weight percent aqueous solution of tetraethylammonium hydroxide;
(g) TBAOH: 40 weight percent aqueous solution of tetrabutylammonium hydroxide;
(h) Pr₂NH: di-n-propylamine, (C₃H₇)₂NH;
(i) Pr₃N: tri-n-propylamine, (C₃H₇)₃N;
(j) Quin: Quinuclidine, (C₇H₁₃N);
(k) MQuin: Methyl Quinuclidine hydroxide, (C₇H₁₃NCH₃OH);
(l) C-hex: cyclohexylamine;
(m) TMAOH: tetramethylammonium hydroxide;
(n) TPAOH: tetrapropylammonium hydroxide; and
(o) DEEA: 2-diethylaminoethanol;
(p) Tetraalkylorthosilicates, such as tetraethylorthosilicate.

Preparative Procedures

BAPSOs may be prepared by forming a starting reaction mixture by dissolving aluminum isopropoxide in an alcohol such as isopropanol, adding the H₃PO₄ and recovering the solid which precipitates. This solid is then added to water, and trialkylborate (for example trimethyl borate) added, followed by silica and the templating agent. This mixture is then blended until a homogeneous mixture is observed. The mixture is then placed in a lined (polytetrafluoroethylene) stainless steel pressure vessel and digested at a temperature (150° C. or 200° C.) for a time or placed in lined screw top bottles for digestion at 100° C. Digestions are typically carried out under autogenous pressure.

BeAPSO MOLECULAR SIEVES

The BeAPSO molecular sieves of U.S. Ser. No. 600,176, filed Apr. 13, 1984, and U.S. Ser. No 841,752 filed Mar. 20, 1986 have a framework structure of $BeO_2^{-2}$, $AlO_2^-$, $PO_2^+$ and $SiO_2$ tetrahedral units having an empirical chemical composition on an anhydrous basis expressed by the formula:

$$mR: (Be_wAl_xP_ySi_z)O_2$$

wherein "R" represents at least one organic templating agent present in the intracrystalline pore system; "m" represents the molar amount of "R" present per mole of $(Be_wAl_xP_ySi_z)O_2$ and has a value of zero to abou 0.3, but is preferably not greater than 0.15; and "w", "x", "y" and "z" represent the mole fractions of the elements beryllium, aluminum, phosphorus and silicon, respectively, present as tetrahedral oxides. The mole fractions "w", "x", "y" and "z" are generally defined as being within the limiting compositional values or points as follows:

| Point | Mole Fraction | | |
|---|---|---|---|
| | x | y | (z + w) |
| A | 0.60 | 0.38 | 0.02 |
| B | 0.38 | 0.60 | 0.02 |
| C | 0.01 | 0.60 | 0.39 |
| D | 0.01 | 0.01 | 0.98 |
| E | 0.60 | 0.01 | 0.39 |

In a preferred subclass of the BeAPSO molecular sieves, the values of w, x, y and z are as follows:

| Point | Mole Fraction | | |
|---|---|---|---|
| | x | y | (z + w) |
| a | 0.60 | 0.38 | 0.02 |
| b | 0.38 | 0.60 | 0.02 |
| c | 0.01 | 0.60 | 0.39 |
| d | 0.01 | 0.39 | 0.60 |
| e | 0.39 | 0.01 | 0.60 |
| f | 0.60 | 0.01 | 0.39 |

BeAPSO compositions are generally synthesized by hydrothermal crystallization from a reaction mixture containing reactive sources of beryllium, silicon, aluminum and phosphorus, preferably an organic templating, i.e., structure-directing, agent, preferably a compound of an element of Group VA of the Periodic Table, and/or optionally an alkali or other metal. The reaction mixture is generally placed in a sealed pressure vessel, preferably lined with an inert plastic material such as polytetrafluoroethylene and heated, preferably under autogenous pressure at a temperature between about 50° C. and about 250° C., and preferably between about 100° C. and about 200° C., until crystals of the BeAPSO product are obtained, usually a period of from several hours to several weeks. Typical effective times of from 2 hours to about 30 days, generally from about 4 hours to about 20 days, have been observed, with from 1 to 10 days being preferred. The product is recovered by any convenient method such as centrifugation or filtration.

In synthesizing the BeAPSO compositions, it is preferred to employ a reaction mixture composition expressed in terms of the molar ratios as follows:

$$aR: (Be_wAl_xP_ySi_z)O_2: bH_2O$$

wherein "R" is an organic templating agent; "a" is the amount of organic templating agent "R" and has a value of from zero to about 6 and is preferably an effective amount within the range of greater than zero (0) to about 6, and most preferably not more than about 0.5; "b" has a value of from zero (0) to about 500, preferably between about 2 to about 300, most preferably not greater than about 20; and "w", "x", "y" and "z" represent the mole fractions of beryllium, aluminum, phosphorus and silicon, respectively, and each has a value of at least 0.01.

In one embodiment the reaction mixture is selected such that the mole fractions "w", "x", "y" and "z" are generally defined as being within the limiting compositional values or points as follows:

| Point | Mole Fraction | | |
|---|---|---|---|
| | x | y | (z + w) |
| F | 0.60 | 0.38 | 0.02 |
| G | 0.38 | 0.60 | 0.02 |
| H | 0.01 | 0.60 | 0.39 |
| I | 0.01 | 0.01 | 0.98 |
| J | 0.60 | 0.01 | 0.39 |

In the foregoing expression of the reaction composition, the reactants are normalized with respect to the total of "w", "x", "y" and "z" such that (w+x+y+z)=1.00 mole. Molecular sieves containing beryllium, aluminum, phosphorus and silicon as framework tetrahedral oxide units are prepared as follows:

Preparative Reagents

BeAPSO compositions may be prepared by using numerous reagents. Reagents which may be employed to prepare BeAPSOs include:

(a) Alipro: aluminum isopropoxide;
(b) CATAPAL: Trademark of Condea Corporation for hydrated pseudoboehmite;
(c) LUDOX-LS: LUDOX-LS is the tradename of Dupont for an aqueous solution of 30 weight percent $SiO_2$ and 0.1 weight percent $Na_2O$;
(d) $H_3PO_4$: 85 weight percent aqueous phosphoric acid;
(e) beryllium sulfate, $BeSO_4$;
(f) TEAOH: 40 weight percent aqueous solution of tetraethylammonium hydroxide;
(g) TBAOH: 40 weight percent aqueous solution of tetrabutylammonium hydroxide;
(h) $Pr_2NH$: di-n-propylamine, $(C_3H_7)_2NH$;
(i) $Pr_3N$: tri-n-propylamine, $(C_3H_7)_3N$;
(j) Quin: Quinuclidine, $(C_7H_{13}N)$;
(k) MQuin: Methyl Quinuclidine hydroxide, $(C_7H_{13}NCH_3OH)$;
(l) C-hex: cyclohexylamine;
(m) TMAOH: tetramethylammonium hydroxide;
(n) TPAOH: tetrapropylammonium hydroxide; and
(o) DEEA: 2-diethylaminoethanol;
(p) Tetraalkylorthosilicates, such as tetraethylorthosilicate.

Preparative Procedures

BeAPSOs may be prepared by forming a starting solution by mixing $H_3PO_4$ in at least part of the water. To this solution is added beryllium sulfate (or another beryllium salt) and the resultant mixture stirred until a homogeneous solution is obtained. To this solution may be added successively the aluminum oxide, the silica and the templating agent, with the mixture being stirred between each addition until it is homogeneous. The mixture is then placed in a lined (polytetrafluoroethylene) stainless steel pressure vessel and digested at a temperature (150° C. or 200° C.) for a time or placed in lined screw top bottles for digestion at 100° C. Digestions are typically carried out under autogenous pressure.

CAPSO MOLECULAR SIEVES

The CAPSO molecular sieves of U.S. Ser. No. 599,830, filed Apr. 13, 1984, and U.S. Ser. No. 852,174 filed Apr. 15, 1986 have a framework structure of $CrO_2^n$, $AlO_2^-$, $PO_2^+$ and $SiO_2$ tetrahedral units (where "n" is $-1$, 0 or $+1$) having an empirical chemical composition on an anhydrous basis expressed by the formula:

mR: $(Cr_wAl_xP_ySi_z)O_2$ wherein "R" represents at least one organic templating agent present in the intracrystalline pore system; "m" represents the molar amount of "R" present per mole of $(Cr_wAl_xP_ySi_z)O_2$ and has a value of zero to abou 0.3, but is preferably not greater than 0.15; and "w", "x", "y" and "z" represent the mole fractions of the elements chromium, aluminum, phosphorus and silicon, respectively, present as tetrahedral oxides. The mole fractions "w", "x", "y" and "z" are generally defined as being within the limiting compositional values or points as follows:

| Point | Mole Fraction | | |
|---|---|---|---|
| | x | y | (z + w) |
| A | 0.60 | 0.38 | 0.02 |
| B | 0.38 | 0.60 | 0.02 |
| C | 0.01 | 0.60 | 0.39 |
| D | 0.01 | 0.01 | 0.98 |
| E | 0.60 | 0.01 | 0.39 |

In a preferred subclass of the CAPSO molecular sieves, the values of w, x, y and z are as follows:

| Point | Mole Fraction | | |
|---|---|---|---|
| | x | y | (z + w) |
| a | 0.60 | 0.38 | 0.02 |
| b | 0.38 | 0.60 | 0.02 |
| c | 0.01 | 0.60 | 0.39 |
| d | 0.01 | 0.39 | 0.60 |
| e | 0.39 | 0.01 | 0.60 |
| f | 0.60 | 0.01 | 0.39 |

In an especially preferred subclass of the CAPSO molecular sieves, the values of x and y in the above formula are each within the range of about 0.4 to 0.5 and (z+w) is in the range of about 0.02 to 0.15.

Since the exact nature of the CAPSO molecular sieves is not clearly understood at present, although all are believed to contain $CrO_2$ tetrahedra in the three-dimensional microporous crystal framework structure, it is advantageous to characterize the CAPSO molecular sieves by means of their chemical composition. This is due to the low level of chromium present in certain of the CAPSO molecular sieves prepared to date which makes it difficult to ascertain the exact nature of the interaction between chromium, aluminum, phosphorus and silicon. As a result, although it is believed that $CrO_2$ tetrahedra are substituted isomorphously for $AlO_2$, $PO_2$ or $SiO_2$ tetrahedra, it is appropriate to characterize certain CAPSO compositions by reference to their chemical composition in terms of the mole ratios of oxides.

CAPSO compositions are generally synthesized by hydrothermal crystallization from a reaction mixture containing reactive sources of chromium, silicon, aluminum and phosphorus, preferably an organic templating, i.e., structure-directing, agent, preferably a compound of an element of Group VA of the Periodic Table, and/or optionally an alkali or other metal. The reaction mixture is eenerally placed in a sealed pressure vessel, preferably lined with an inert plastic material such as polytetrafluoroethylene and heated, preferably under autogenous pressure at a temperature between about 50° C. and about 250° C., and preferably between about 100° C. and about 200° C., until crystals of the CAPSO product are obtained, usually a period of from several hours to several weeks. Typical effective times of from 2 hours to about 30 days, generally from about 4 hours to about 20 days, and preferably about 1 to about 10 days, have been observed. The product is recovered by any convenient method such as centrifugation or filtration.

In synthesizing the CAPSO compositions, it is preferred to employ a reaction mixture composition expressed in terms of the molar ratios as follows:

aR: $(Cr_wAl_xP_ySi_z)O_2$: $bH_2O$ wherein "R" is an organic templating agent; "a" is the amount of organic templating agent "R" and has a value of from zero to about 6 and is preferably an effective amount within the range of greater than zero (0) to about 6, and most preferably not more than about 0.5; "b" has a value of from zero (0) to about 500, preferably between about 2 and about 300, most preferably not greater than about 20; and "w", "x", "y" and "z" represent the mole fractions of chromium, aluminum, phosphorus and silicon, respectively, and each has a value of at least 0.01.

In one embodiment the reaction mixture is selected such that the mole fractions "w", "x", "y" and "z" are generally defined as being within the limiting compositional values or points as follows:

| Point | Mole Fraction | | |
|---|---|---|---|
| | x | y | (z + w) |
| F | 0.60 | 0.38 | 0.02 |
| G | 0.38 | 0.60 | 0.02 |
| H | 0.01 | 0.60 | 0.39 |
| I | 0.01 | 0.01 | 0.98 |
| J | 0.60 | 0.01 | 0.39 |

Especially preferred reaction mixtures are those containing from about 0.3 to about 0.5 total moles of silicon and chromium, and from about 0.75 to about 1.25 moles of aluminum, per mole of phosphorus.

In the foregoing expression of the reaction composition, the reactants are normalized with respect to the total of "w", "x", "y" and "z" such that $(w+x+y+z)=1.00$ mole. Molecular sieves containing chromium, aluminum, phosphorus and silicon as framework tetrahedral oxide units are prepared as follows:

Preparative Reagents

CAPSO compositions may be prepared by using numerous reagents. Ragents which may be employed to prepare CAPSOs include:
(a) Alipro: aluminum isopropoxide;
(b) CATAPAL: Trademark of Condea Corporation for hydrated pseudoboehmite;
(c) LUDOX-LS: LUDOX-LS is the tradename of DuPont for an aqueous solution of 30 weight percent $SiO_2$ and 0.1 weight percent $Na_2O$;
(d) $H_3PO_4$: 85 weight percent aqueous phosphoric acid;
(e) chromium acetate, and chromium acetate hydroxide;
(f) TEAOH: 40 weight percent aqueous solution of tetraethylammonium hydroxide;
(g) TBAOH: 40 weight percent aqueous solution of tetrabutylammonium hydroxide;
(h) $Pr_2NH$: di-n-propylamine, $(C_3H_7)_2NH$;
(i) $Pr_3N$: tri-n-propylamine, $(C_3H_7)_3N$;
(j) Quin: Quinuclidine, $(C_7H_{13}N)$;
(k) MQuin: Methyl Quinuclidine hydroxide, $(C_7H_{13}NCH_3OH)$;
(l) C-hex: cyclohexylamine;
(m) TMAOH: tetramethylammonium hydroxide;
(n) TPAOH: tetrapropylammonium hydroxide; and
(o) DEEA: 2-diethylaminoethanol;
(p) Tetraalkylorthosilicates, such as tetraethylorthosilicate.

Preparative Procedures

CAPSOs may be prepared by forming a starting solution by dissolving $H_3PO_4$ in at least part of the water. To this solution the aluminum isopropoxide is added. This mixture is then blended until a homogeneous mixture is observed. To this mixture the silica, the chromium acetate or chromium acetate hydroxide and the templating agent are successively added and at each step the resulting mixture is blended until a homogeneous mixture is observed.

Alternatively, the water and aluminum isopropoxide may first be mixed, and then the silica, the chromium acetate or chromium acetate hydroxide, the phosphoric acid and the templating agent added, and again at each step the resulting mixture is blended until a homogeneous mixture is observed.

In either case, the mixture is then placed in a lined (polytetrafluoroethylene) stainless steel pressure vessel and digested at a temperature (150° C. or 200° C.) for a time or placed in lined screw top bottles for digestion at 100° C. Digestions are typically carried out under autogenous pressure.

GaAPSO MOLECULAR SIEVES

The GaAPSO molecular sieves of U.S. Ser. No. 599,925, filed Apr. 13, 1984, and U.S. Ser. No. 845,985 filed Mar. 31, 1986 have a framework structure of $GaO_2^-$, $AlO_2^-$, $PO_2^+$ and $SiO_2$ tetrahedral units having an empirical chemical composition on an anhydrous basis expressed by the formula:

$$mR: (Ga_wAl_xP_ySi_z)O_2$$

wherein "R" represents at least one organic templating agent present in the intracrystalline pore system; "m" represents the molar amount of "R" present per mole of $(Ga_wAl_xP_ySi_z)O_2$ and has a value of zero to about 0.3, but is preferably not greater than 0.2; and "w", "x", "y" and "z" represent the mole fractions of the elements gallium, aluminum, phosphorus and silicon, respectively, present as tetrahedral oxides. The mole fractions "w", "x", "y" and "z" are generally defined as being within the limiting compositional values or points as follows:

| Point | Mole Fraction | | |
|---|---|---|---|
| | x | y | (z + w) |
| A | 0.60 | 0.38 | 0.02 |
| B | 0.38 | 0.60 | 0.02 |
| C | 0.01 | 0.60 | 0.39 |
| D | 0.01 | 0.01 | 0.98 |
| E | 0.60 | 0.01 | 0.39 |

In a preferred subclass of the GaAPSO molecular sieves, the values of w, x, y and z are as follows:

| Point | Mole Fraction | | |
|---|---|---|---|
| | x | y | (z + w) |
| a | 0.60 | 0.38 | 0.02 |
| b | 0.38 | 0.60 | 0.02 |
| c | 0.01 | 0.60 | 0.39 |
| d | 0.01 | 0.39 | 0.60 |
| e | 0.39 | 0.01 | 0.60 |
| f | 0.60 | 0.01 | 0.39 |

In an especially preferred subclass of the GaAPSO molecular sieves, the values of w, x, y and z are as follows:

| Point | Mole Fraction | | |
|---|---|---|---|
| | x | y | (z + w) |
| g | 0.45 | 0.40 | 0.15 |
| h | 0.33 | 0.52 | 0.15 |
| i | 0.20 | 0.52 | 0.28 |
| j | 0.20 | 0.45 | 0.35 |
| k | 0.36 | 0.29 | 0.35 |
| l | 0.45 | 0.29 | 0.26 |

GaAPSO compositions are generally synthesized by hydrothermal crystallization from a reaction mixture containing reactive sources of gallium, silicon, aluminum and phosphorus, preferably an organic templating, i.e., structure-directing, agent, preferably a compound of an element of Group VA of the Periodic Table, and/or optionally an alkali or other metal. The reaction mixture is generally placed in a sealed pressure vessel, preferably lined with an inert plastic material such as polytetrafluoroethylene and heated, preferably under autogenous pressure at a temperature between about 50° C. and about 250° C., and preferably between about 100° C. and about 200° C., until crystals of the GaAPSO product are obtained, usually a period of from several hours to several weeks. Typical effective times of from 2 hours to about 30 days, generally from about 4 hours to about 20 days, and preferably about 2 to about 15 days, have been observed. The product is recovered by any convenient method such as centrifugation or filtration.

In synthesizing the GaAPSO compositions, it is preferred to employ a reaction mixture composition expressed in terms of the molar ratios as follows:

$$aR: (Ga_wAl_xP_ySi_z)O_2: bH_2O$$

wherein "R" is an organic templating agent; "a" is the amount of organic templating agent "R" and has a value of from zero to about 6 and is preferably an effective amount within the range of greater than zero (0) to about 6, and most preferably not more than about 1.0; "b" has a value of from zero (0) to about 500, preferably between about 2 and about 300, most preferably not greater than about 20; and "w", "x", "y" and "z" represent the mole fractions of gallium, aluminum, phosphorus and silicon, respectively, and each has a value of at least 0.01.

In one embodiment the reaction mixture is selected such that the mole fractions "w", "x", "y" and "z" are generally defined as being within the limiting compositional values or points as follows:

| Point | Mole Fraction | | |
|---|---|---|---|
| | x | y | (z + w) |
| F | 0.60 | 0.38 | 0.02 |
| G | 0.38 | 0.60 | 0.02 |
| H | 0.01 | 0.60 | 0.39 |
| I | 0.01 | 0.01 | 0.98 |
| J | 0.60 | 0.01 | 0.39 |

Especially preferred reaction mixtures are those containing from about 0.5 to about 1.0 total moles of silicon and gallium, and from about 0.75 about 1.25 moles of aluminum, per mole of phosphorus.

In the foregoing expression of the reaction composition, the reactants are normalized with respect to the total of "w", "x", "y" and "z" such that $(w+x+y+z)=1.00$ mole. Molecular sieves containing gallium, aluminum, phosphorus and silicon as framework tetrahedral oxide units are prepared as follows:

Preparative Reagents

GaAPSO compositions may be prepared by using numerous reagents. Reagents which may be employed to prepare GaAPSOs include:
(a) Alipro: aluminum isopropoxide;
(b) CATAPAL: Trademark of Condea Corporation for hydrated pseudoboehmite;
(c) LUDOX-LS: LUDOX-LS is the tradename of Dupont for an aqueous solution of 30 weight percent $SiO_2$ and 0.1 weight percent $Na_2O$;
(d) $H_3PO_4$: 85 weight percent aqueous phosphoric acid;
(e) gallium hydroxide, or gallium sulfate;
(f) TEAOH: 40 weight percent aqueous solution of tetraethylammonium hydroxide;
(g) TBAOH: 40 weight percent aqueous solution of tetrabutylammonium hydroxide;
(h) $Pr_2NH$: di-n-propylamine, $(C_3H_7)_2NH$;
(i) $Pr_3N$: tri-n-propylamine, $(C_3H_7)_2NH$;
(j) Quin: Quinuclidine, $(C_7H_{13}N)$;
(k) MQuin: Methyl Quinuclidine hydroxide, $(C_7H_{13}NCH_3OH)$;
(l) C-hex: cyclohexylamine;
(m) TMAOH: tetramethylammonium hydroxide;
(n) TPAOH: tetrapropylammonium hydroxide; and
(o) DEEA: 2-diethylaminoethanol;
(p) Tetraalkylorthosilicates, such as tetraethylorthosilicate.

Preparative Procedures

GaAPSOs may be prepared by forming a starting solution by dissolving $H_3PO_4$ in at least part of the water. To this solution the aluminum hydroxide or isopropoxide is added. This mixture is then blended until a homogeneous mixture is observed. To this mixture is added a second solution prepared by adding silica to a solution containing the gallium hydroxide and the templating agent and then the combined mixture is blended until a homogeneous mixture is observed.

Alternatively, the templating agent may be added to the solution containing the phosphoric acid and water, and a solution of gallium sulfate in water added, followed by successive additions of silica and aluminum oxide and then the combined mixture is blended until a homogeneous mixture is observed.

In either case, the mixture is then placed in a lined (polytetrafluoroethylene) stainless steel pressure vessel and digested at a temperature (150° C. or 200° C.) for a time or placed in lined screw top bottles for digestion at 100° C. Digestions are typically carried out under autogenous pressure.

GeAPSO MOLECULAR SIEVES

The GeAPSO molecular sieves of U.S. Ser. No. 599,971, filed Apr. 13, 1984, and U.S. Ser. No. 852,175 filed Apr. 15, 1986 have a framework structure of $GeO_2$, $AlO_2^-$, $PO_2^+$ and $SiO_2$ tetrahedral units having an empirical chemical composition on an anhydrous basis expressed by the formula:

$$mR: (Ge_wAl_xP_ySi_z)O_2$$

wherein "R" represents at least one organic templating agent present in the intracrystalline pore system; "m" represents the molar amount of "R" present per mole of $(Ge_wAl_xP_ySi_z)O_2$ and has a value of zero to abou 0.3, but is preferably not greater than 0.15; and "w", "x", "y" and "z" represent the mole fractions of the elements geranium, aluminum, phosphorus and silicon, respectively, present as tetrahedral oxides. The mole fractions "w", "x", "y" and "z" are generally defined as being within the limited compositional values or points as follows:

| Point | Mole Fraction | | |
|---|---|---|---|
| | x | y | (z + w) |
| A | 0.60 | 0.38 | 0.02 |
| B | 0.38 | 0.60 | 0.02 |
| C | 0.01 | 0.60 | 0.39 |
| D | 0.01 | 0.01 | 0.98 |
| E | 0.60 | 0.01 | 0.39 |

In a preferred subclass of the GeAPSO molecular sieves, the values of w, x, y and z are as follows:

| Point | Mole Fraction | | |
|---|---|---|---|
| | x | y | (z + w) |
| a | 0.60 | 0.38 | 0.02 |
| b | 0.38 | 0.60 | 0.02 |
| c | 0.01 | 0.60 | 0.39 |
| d | 0.01 | 0.39 | 0.60 |
| e | 0.39 | 0.01 | 0.60 |
| f | 0.60 | 0.01 | 0.39 |

In an especially preferred subclass of the GeAPSO molecular sieves, the values of w, x, y and z are as follows:

| Point | Mole Fraction | | |
|---|---|---|---|
| | x | y | (z + w) |
| g | 0.60 | 0.35 | 0.05 |
| h | 0.47 | 0.48 | 0.05 |
| i | 0.40 | 0.48 | 0.12 |
| j | 0.40 | 0.36 | 0.24 |
| k | 0.46 | 0.30 | 0.24 |
| l | 0.60 | 0.30 | 0.10 |

GeAPSO compositions are generally synthesized by hydrothermal crystallization from a reaction mixture containing reactive sources of geranium, silicon, aluminum and phosphorus, preferably an organic templating, i.e., structure-directing, agent, preferably a compound of an element of Group VA of the Periodic Table, and/or optionally an alkali or other metal. The reaction mixture is generally placed in a sealed pressure vessel, preferably lined with an inert plastic material such as polytetrafluoroethylene and heated, preferably under autogenous pressure at a temperature between about 50° C. and about 250° C., and preferably between about 100° C. and about 200° C., until crystals of the GeAPSO product are obtained, usually a period of from several hours to several weeks. Typical effective times of from 2 hours to about 30 days, generally from about 4 hours to about 20 days, and preferably about 12 hours to about 7 days have been observed. The product is recovered by any convenient method such as centrifugation or filtration.

In synthesizing the GaAPSO compositions, it is preferred to employ a reaction mixture composition expressed in terms of the molar ratios as follows:

aR: $(Ge_wAl_xP_ySi_z)O_2$: bH$_2$O wherein "R" is an organic templating agent; "a" is the amount of organic templating agent "R" and has a value of from zero to about 6 and is preferably an effective amount within the range of greater than zero (0) to about 6, and most preferably not more than about 0.5; "b" has a value of from zero (0) to about 500, preferably between about 2 and about 300, most preferably not greater than about 20; and desirably not greater than about 10; and "w", "x", "y" and "z" represent the mole fractions of germanium, aluminum, phosphorus and silicon, respectively, and each has a value of at least 0.01.

In one embodiment the reaction mixture is selected such that the mole fractions "w", "x", "y" and "z" are generally defined as being within the limiting compositional values or points as follows:

| Point | Mole Fraction | | |
|---|---|---|---|
| | x | y | (z + w) |
| F | 0.60 | 0.38 | 0.02 |
| G | 0.38 | 0.60 | 0.02 |
| H | 0.01 | 0.60 | 0.39 |
| I | 0.01 | 0.01 | 0.98 |
| J | 0.60 | 0.01 | 0.39 |

Especially preferred reaction mixtures are those containing from about 0.2 to about 0.3 total moles of silicon and germanium, and from about 0.75 about 1.25 moles of aluminum, per mole of phosphorus.

In the foregoing expression of the reaction composition, the reactants are normalized with respect to the total of "w", "x", "y" and "z" such that (w+x+y+z)=1.00 mole. Molecular sieves containing germanium, aluminum, phosphorus and silicon as framework tetrahedral oxide units are prepared as follows:

Preparative Reagents

GeAPSO compositions may be prepared by numerous reagents. Reagents which may be employed to prepare GeAPSOs include:
(a) Alipro: aluminum isopropoxide;
(b) CATAPAL: Trademark of Condea Corporation for hydrated pseudoboehmite;
(c) LUDOX-LS: LUDOX-LS is the tradename of DuPont for an aqueous solution of 30 weight percent SiO$_2$ and 0.1 weight percent Na$_2$O;
(d) H$_3$PO$_4$: 85 weight percent aqueous phosphoric acid;
(e) germanium tetrachloride or germanium ethoxide;
(f) TEAOH: 40 weight percent aqueous solution of tetraethylammonium hydroxide;
(g) TBAOH: 40 weight percent aqueous solution of tetrabutylammonium hydroxide;
(h) Pr$_2$NH: di-n-propylamine, (C$_3$H$_7$)2NH;
(i) Pr$_3$N: tri-n-propylamine, (C$_3$H$_7$)$_3$N;
(j) Quin: Quinuclidine, (C$_7$H$_{13}$N);
(k) MQuin: Methyl Quinuclidine hydroxide, (C$_7$H$_{13}$NCH$_3$OH);
(l) C-hex: cyclohexylamine;
(m) TMAOH: tetramethylammonium hydroxide;
(n) TPAOH: tetrapropylammonium hydroxide; and
(o) DEEA: 2-diethylaminoethanol;
(p) Tetraalkylorthosilicates, such as tetraethylorthosilicate; and
(q) aluminum chlorhydrol.

Preparative Procedures

In some cases, it may be advantageous, when synthesizing the GeAPSO compositions, to first combine sources of germanium and aluminum, or of germanium, aluminum and silicon, to form a mixed germanium-/aluminum or germanium/aluminum/silicon compound (this compound being typically a mixed oxide) and thereafter to combine this mixed compound with a source of phosphorus to form the final GeAPSO composition. Such mixed oxides may be prepared for example by hydrolyzing aqueous solutions containing germanium tetrachloride and aluminum chlorhydrol, or germanium ethoxide, tetraethylorthosilicate, and aluminum tri-sec-butoxide.

GeAPSOs may be prepared by forming a starting solution by dissolving $H_3PO_4$ in at least part of the water. To this solution the aluminum isopropoxide or CATAPAL is added. This mixture is then blended until a homogeneous mixture is observed. To this mixture is the templating agent and then a solution containing tetraethylorthosilicate and germanium ethoxide, and the resulting mixture blended until a homogeneous mixture is observed.

Alternatively, the phosphoric acid may first be mixed with the templating agent, and then a solution containing tetraethylorthosilicate and germanium ethoxide combined with the phosphoric acid/templating agent solution. Then the aluminum oxide is added and the resultant mixture blended until homogeneous.

In a third procedure, the phosphoric acid may first be mixed with the templating agent and water, and to the resultant solution is added the solid aluminum/silicon/germanium mixed oxide prepared as described above. The resultant mixture is then blended until homogeneous.

Whichever procedure is adopted, the final mixture is then placed in a lined (polytetrafluoroethylene) stainless steel pressure vessel and digested at a temperature (150° C. or 200° C.) for a time or placed in lined screw top bottles for digestion at 100° C. Digestions are typically carried out under autogenous pressure.

LiAPSO MOLECULAR SIEVES

The LiAPSO molecular sieves of U.S. Ser. No. 599,952, filed Apr. 13, 1984, and U.S. Ser. No. 847,227 filed Apr. 2, 1986 have a framework structure of $LiO_2^{-3}$, $AlO_2^{-}$, $PO_2^{+}$ and $SiO_2$ tetrahedral units having an empirical chemical composition on an anhydrous basis expressed by the formula:

wherein "R" represents at least one organic templating agent present in the intracrystalline pore system; "m" represents the molar amount of "R" present per mole of $(Li_wAl_xP_ySi_z)O_2$ and has a value of zero to about 0.3, but is preferably not greater than 0.15; and "w", "x", "y" and "z" represent the mole fractions of the elements lithium, aluminum, phosphorus and silicon, respectively, present as tetrahedral oxides. The mole fractions "w", "x", "y" and "z" are generally defined as being within the limiting compositional values or points as follows:

| Point | Mole Fraction | | |
|---|---|---|---|
| | x | y | (z + w) |
| A | 0.60 | 0.38 | 0.02 |
| B | 0.38 | 0.60 | 0.02 |
| C | 0.01 | 0.60 | 0.39 |
| D | 0.01 | 0.01 | 0.98 |
| E | 0.60 | 0.01 | 0.39 |

In a preferred subclass of the LiAPSO molecular sieves, the values of w, x, y and z are as follows

| Point | Mole Fraction | | |
|---|---|---|---|
| | x | y | (z + w) |
| a | 0.60 | 0.38 | 0.02 |
| b | 0.38 | 0.60 | 0.02 |
| c | 0.01 | 0.60 | 0.39 |
| d | 0.01 | 0.39 | 0.60 |
| e | 0.39 | 0.01 | 0.60 |
| f | 0.60 | 0.01 | 0.39 |

In an especially preferred subclass of the LiAPSO molecular sieves, the value of w+z is not greater than about 0.20.

Since the exact nature of the LiAPSO molecular sieves is not clearly understood at present, although all are believed to contain $LiO_2$ tetrahedra in the three-dimensional microporous crystal framework structure, it is advantageous to characterize the LiAPSO molecular sieves by means of their chemical composition. This is due to the low level of lithium present in certain of the LiAPSO molecular sieves prepared to date which makes it difficult to ascertain the exact nature of the interaction between lithium, aluminum, phosphorus and silicon. As a result, although it is believed that $LiO_2$ tetrahedra are substituted isomorphously for $AlO_2$, $PO_2$ or $SiO_2$ tetrahedra, it is appropriate to characterize certain LiAPSO compositions by reference to their chemical composition in terms of the mole ratios of oxides.

LiAPSO compositions are generally synthesized by hydrothermal crysallization from a reaction mixture containing reactive sources of lithium, silicon, aluminum and phosphorus, preferably an organic templating, i.e., structure directing, agent, preferably a compound of an element of Group VA of the Periodic Table, and-/or optionally an alkali or other metal. The reaction mixture is generally placed in a sealed pressure vessel, preferably lined with an inert plastic material such as polytetrafluoroethylene and heated, preferably under autogenous pressure at a temperature between about 50° C. and about 250° C., and preferably between about 100° C. and about 200° C. until crystals of the LiAPSO product are obtained, usually a period of from several hours to several weeks. Typical effective times of from 2 hours to about 30 days, generally from about 4 hours to about 20 days, and preferably about 1 to about 10 days, have been observed. The product is recovered by any convenient method such as centrifugation or filtration.

In synthesizing the LiAPSO compositions, it is preferred to employ a reaction mixture composition expressed in terms of the molar ratios as follows:

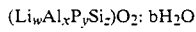

wherein "R" is an organic templating agent; "a" is the amount of organic templating agent "R" and has a value of from zero to about 6 and is preferably an effective amount within the range of greater than zero (0) to about 6, and most preferably not more than about 0.5; "b" has a value of from zero (0) to about 500, preferably between about 2 and about 300, most preferably not greater than about 20, and most desirably not greater than about 10; and "w", "x", "y" and "z" represent the mole fractions of lithium, aluminum, phosphorus and silicon, respectively, and each has a value of at least 0.01.

In one embodiment the reaction mixture is selected such that the mole fractions "w", "x", "y" and "z" are generally defined as being within the limiting compositional values or points as follows:

|       | Mole Fraction |      |         |
|-------|------|------|---------|
| Point | x    | y    | (z + w) |
| F     | 0.60 | 0.38 | 0.02    |
| G     | 0.38 | 0.60 | 0.02    |
| H     | 0.01 | 0.60 | 0.39    |
| I     | 0.01 | 0.01 | 0.98    |
| J     | 0.60 | 0.01 | 0.39    |

In the foregoing expression of the reaction composition, the reactants are normalized with respect to the total of "w", "x", "y" and "z" such that (w+x+y+z)=1.00 mole. Molecular sieves containing lithium, aluminum, phosphorus and silicon as framework tetrahedral oxide units are prepared as follows:

preparative Reagents

LiAPSO compositions may be prepared by using numerous reagents. Reagents which may be employed to prepare LiAPSOs include:
(a) Alipro: aluminum isopropoxide;
(b) CATAPAL: Trademark of Condea Corporation for hydrated pseudoboehmite;
(c) LUDOX-LS: LUDOX-LS is the tradename of DuPont for an aqueous solution of 30 weight percent $SiO_2$ and 0.1 weight percent $Na_2O$;
(d) $H_3PO_4$: 85 weight percent aqueous-phosphoric acid;
(e) lithium orthophosphate;
(f) TEAOH: 40 weight percent aqueous solution of tetraethylammonium hydroxide;
(g) TBAOH: 40 weight percent aqueous solution of tetrabutylammonium hydroxide;
(h) $Pr_2NH$: di-n-propylamine, $(C_3H_7)_2NH$;
(i) $Pr_3N$: tri-n-propylamine, $(C_3H_7)_3N$;
(j) Quin: Quinuclidine, $(C_7H_{13}N)$;
(k) MQuin: Methyl Quinuclidine hydroxide, $(C_7H_{13}NCH_3OH)$;
(l) C-hex: cyclohexylamine;
(m) TMAOH: tetramethylammonium hydroxide;
(n) TPAOH: tetrapropylammonium hydroxide; and
(o) DEEA: 2 diethylaminoethanol;
(p) Tetraalkylorthosilicates, such as tetraethylorthosilicate.

Preparative Procedures

LiAPSOs may be prepared by forming a starting reaction mixture mixing lithium phosphate and aluminum oxide, then adding the resultant mixture to the $H_3PO_4$. To the resultant mixture is added silica and the templating agent and the resulting mixture is blended until a homogeneous mixture is observed. The mixture is then placed in a lined (polytetrafluoroethylene) stainless steel pressure vessel and digested at a temperature (150° C. or 200° C.) for a time or placed in lined screw top bottles for digestion at 100° C. Digestions are typically carried out under autogenous pressure.

$AlPO_4$ ALUMINOPHOSPHATE MOLECULAR SIEVES

The $AlPO_4$ aluminophosphate molecular sieves of U.S. Pat. No. 4,310,440 and U.S. Ser. No. 880,559, filed June 30, 1986 are disclosed as microporous crystalline aluminophosphates having an essential crystalline framework structure whose chemical composition, expressed in terms of molar ratios of oxides, is:

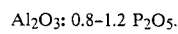
$Al_2O_3$: 0.8–1.2 $P_2O_5$.

The pores of the framework structure are uniform and in each species have nominal diameters of from 3 to 10 Angstroms; the aluminophosphates have an intracrystalline adsorption capacity for water at 4.6 Torr and 24° C. of at least 3.5 weight percent, the adsorption of water being completely reversible while retaining the same essential framework topology in both the hydrated and dehydrated state. By the term "essential framework topology" is meant the spatial arrangement of the primary Al-O and P-O bond linkages. No change in the framework topology indicates that there is no disruption of these primary bond linkages.

The aluminophosphates are prepared by hydrothermal crystallization of a reaction mixture prepared by combining a reactive source of phosphate, alumina and water and at least one structure directing or templating agent which can include an organic amine and a quaternary ammonium salt. In the as synthesized form, the structure directing agent is contained within the framework structure of the aluminophosphate in amounts which vary from species to species but usually do not exceed one mole per mole of $Al_2O_3$ thereof. This structure-directing agent is readily removed by water washing or calcination and does not appear to be an essential constituent of the aluminophosphate, as evidenced by essentially complete absence of ion-exchangeability of the as-synthesized compositions and also the complete absence of any internally-contained organic molecules in the as-synthesized form of at least one species of the generic class. Evidence that structure directing agent is a critical constituent is contained in certain of the Examples of the U.S. Pat. No. 4,310,440, wherein reaction mixtures, otherwise identical to those which yield the $AlPO_4$ products except for the presence of templating agents, yield instead the previously known aluminophosphate phases $AlPO_4.I.I$- 1.3 $H_2O$, $AlPO_4$ tridymite, $AlPO_4$-quartz and $AlPO_4$-cristobalite.

The $AlPO_4$ aluminophosphates are prepared by forming a reaction mixture which contains, in terms of molar ratios of oxides:

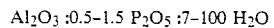
$Al_2O_3$ :0.5–1.5 $P_2O_5$ :7–100 $H_2O$ and contains from about 0.2 to 2.0 moles of templating agent per mole of $Al_2O_3$. The reaction mixture is placed in a reaction vessel inert toward the reaction system and heated at a temperature of at least about 100° C., preferably between 100° C. and 300° C., until crystallized, usually a period from 2 hours to 2 weeks. The solid crystalline reaction product is then recovered by any convenient method, such as filtration or centrifugation, washed with water and dried at a temperature between ambient and 110° C., preferably in air.

MeAPO MOLECULAR SIEVES

MeAPO molecular sieves are crystalline microporous aluminophosphates in which the substituent metal is one of a mixture of two or more divalent metals of the group magnesium, manganese, zinc and cobalt and are disclosed in U.S. Pat. No. 4,567,029. Members of this novel class of compositions have a three dimensional microporous crystal framework structure of $MO_2^{-2}$, $AlO_2^{-}$ and $PO_2^{+}$ tetrahedral units and have an essential empirical chemical composition, on an anhydrous basis, of:

mR: $(M_xAl_yP_z)O_2$ wherein "R" represents at least one organic templating agent present in the intracrystalline pore system; "m" represents the moles of "R" present per mole of $(M_xAl_yP_z)O_2$ and has a value of from zero to 0.3 maximum value in each case depending upon the molecular dimensions of the templating agent and the available void volume of the pore system of the particular metal aluminophosphate involved; "x", "y", and "z" represent the mole fractions of the metal "M", (i.e., magnesium, manganese, zinc and cobalt), aluminum and phosphorus, respectively, present as tetrahedral oxides, said mole fractions being such that they are representing the following values for "x", "y", and "z":

| Point | Mole Fraction | | |
|---|---|---|---|
| | x | y | z |
| A | 0.01 | 0.60 | 0.39 |
| B | 0.01 | 0.39 | 0.60 |
| C | 0.35 | 0.05 | 0.60 |
| D | 0.35 | 0.60 | 0.05 |

When synthesized the minimum value of "m" in the formula above is 0.02. In a preferred subclass of the metal aluminophosphates of this invention, the values of "x", "y" and "z" in the formula above are representing the following values for "x", "y" and "z":

| Point | Mole Fraction | | |
|---|---|---|---|
| | x | y | z |
| a | 0.01 | 0.52 | 0.47 |
| b | 0.01 | 0.39 | 0.60 |
| c | 0.25 | 0.15 | 0.60 |
| d | 0.25 | 0.40 | 0.35 |

The as synthesized compositions are capable of withstanding 350° C. calcination in air for extended periods, i.e., at least 2 hours, without becoming amorphous. While it is believed that the M, Al and P framework constituents are present in tetrahedral coordination with oxygen, it is theoretically possible that some minor fraction of these framework constituents are present in coordination with five or six oxygen atoms. It is not, moreover, necessarily the case that all of the M, Al and/or P content of any given synthesized product is a part of the framework in the aforesaid types of coordination with oxygen. Some of each constituent may be merely occluded or in some as yet undetermined form and may or may not be structurally significant.

Since the term "metal aluminophosphate" is somewhat cumbersome, particularly in view of the need for numerous repetitions thereof in describing such compositions, the "short hand" reference "MeAPO" is employed hereinafter. Also in those cases where the metal "Me" in the composition is magnesium, the acronym MAPO is applied to the composition. Similarly, ZAPO, MnAPO, and CoAPO are applied to the compositions which contain zinc, manganese and cobalt, respectively. To identify the various structural species which make up each of the subgeneric classes MAPO, ZAPO, CoAPO and MnAPO, each species is assigned a number and is identified, for example, as ZAPO-5, MAPO-11, CoAPO-11 and so forth.

The term "essential empirical chemical composition" is meant to include the crystal framework and can include any organic templating agent present in the pore system, but does not include alkali metal or other ions which can be present by virtue of being contained in the reaction mixture or as a result of post synthesis ion-exchange. Such ionic species, when present, function primarily as charge-balancing ions for $AlO_2^{-}$ and/or $MO_2^{-2}$ tetrahedra not associated with $PO_2^{+}$ tetrahedra or an organic ion derived from the organic templating agent.

The metal aluminophosphates ("MeAPOs" are synthesized by hydrothermal crystallization from a reaction mixture containing reactive sources of the metal "M", alumina and phosphate, an organic templating, i.e., structure-directing, agent, preferably a compound of an element of Group VA of the Periodic Table, and optionally an alkali metal. The reaction mixture is placed in a sealed pressure vessel, preferably lined with an inert plastic material such as polytetrafluoroethylene and heated, preferably under autogenous pressure at a temperature between 100° C. and 225° C., and preferably between 100° C. and 200° C., until crystals of the metal aluminophosphate product are obtained, usually a period of from 4 hours to 2 weeks. The product is recovered by any convenient method such as centrifugation or filtration.

In synthesizing the MeAPO compositions, it is preferred to employ a reaction mixture composition expressed in terms of molar ratios as follows:

$aR:(M_xAl_yP_z)O_2:bH_2O$ wherein "R" is an organic templating agent; "a" has a value great enough to constitute an effective concentration of "R" and is within the range of >0 to 6; "b" has a value of from zero to 500, preferably 2 to 30; "M" represents a metal of the group zinc, magnesium, manganese and coalt, "x", "y" and "z" represent the mole fractions, respectively, of "M", aluminum and phosphorus in the $(MAl_yP_z)O_2$ constituent, and each has a value of at least 0.01, the said points E, F, G, H, I, and J representing the following values for "x", "y" and "z":

| Point | Mole Fraction | | |
|---|---|---|---|
| | x | y | z |
| E | 0.01 | 0.70 | 0.29 |
| F | 0.01 | 0.29 | 0.70 |
| G | 0.29 | 0.01 | 0.70 |
| H | 0.40 | 0.01 | 0.59 |
| I | 0.40 | 0.59 | 0.01 |
| J | 0.29 | 0.70 | 0.01 |

In the foregoing expression of the reaction composition, the reactants are normalized with respect to a total of $(M+Al+P)=(x+y+z)=1.00$ mole In forming the reaction mixture from which the metal aluminophosphates are crystallized the organic templating agent can be any of those heretofore proposed for use in the synthesis of conventional zeolite aluminosilicates and microporous aluminophosphates. In general these compounds contain elements of Group VA of the Periodic Table of Elements, particularly nitrogen, phosphorus, arsenic and antimony, preferably N or P and most preferably N, which compounds also contain at least one alkyl or aryl group having from 1 to 8 carbon atoms. Particularly preferred nitrogen-containing compounds for use as templating agents are the amines and quaternary ammonium compounds, the latter being represented generally by the formula $R_4N^+$ wherein each R is an alkyl or aryl group containing from 1 to 8 carbon atoms. Polymeric quaternary ammonium salts such as $[(C_{14}H_{32}N_2)(OH)_2]_x$ wherein "x" has a value of at least 2 are also suitably employed. Both mono , di- and triamines are advantageously utilized, either alone or in combination with a quaternary ammonium compound or other templating compound. Mixtures of two or more templating agents can either produce mixtures of the desired metal aluminophosphates or the more strongly directing templating species may control the course of the reaction with the other templating species serving primarily to establish the pH conditions of the reaction gel. Representative templating agents include tetramethylammonium, tetraethylammonium, tetrapropylammonium or tetrabutylammonium ions; di n-propylamine; tripropylamine; triethylamine; triethanolamine; piperidine; cyclohexylamine; 2 methylpyridine; N,N dimethylbenzylamine; N-N-dimethylethanolamine; choline; N,N'-dimethylpiperazine; 1,4-diazabicyclo (2,2,2) octane; N methyldiethanolamine; N-methylethanolamine; N-methylpiperidine; 3-methylpiperidine; N-methylcyclohexylamine; 3-methylpyridine; 4-methylpyridine; quinuclidine; N,N'-dimethyl-1,4-diazabicyclo (2,2,2) octane ion; di-n-butylamine, neopentylamine; di-n-pentylamine; isopropylamine; t butylamine; ethylenediamine; pyrrolidine; and 2 imidazolidone. Not every templating agent will direct the formation of every species of metal aluminophosphate (MeAPO), i.e., a single templating agent can, with proper manipulation of the reaction conditions, direct the formation of several MeAPO compositions, and a given MeAPO composition can be produced using several different templating agents.

The preferred phosphorus source is phosphoric acid, but organic phosphates such as triethylphosphate have been found satisfactory, and so also have crystalline or amorphous aluminophosphates such as the AlPO₄ composition of U.S. Pat. No. 4,310,440. Organo-phosphorus compounds, such as tetrabutylphosphonium bromide do not, apparently serve as reactive sources of phosphorus, but these compounds do function as templating agents. Conventional phosphorus salts such as sodium metaphosphate, may be used, at least in part, as the phosphorus source, but are not preferred.

The aluminum source is preferably either an aluminum alkoxide, such as aluminum isopropoxide, or pseudoboehmite. The crystalline or amorphous aluminophosphates which are a suitable source of phosphorus are, of course, also suitable sources of aluminum. Other sources of aluminum used in zeolite synthesis, such as gibbsite, sodium aluminate and aluminum trichloride, can be employed but are not preferred.

The metals zinc, cobalt, maqnesium and manganese can be introduced into the reaction system in any form which permits the formation in situ of reactive divalent ions of the respective metals. Advantageously salts, oxides or hydroxides of the metals are employed such as cobalt chloride hexahydrate, alpha cobaltous iodide, cobaltous sulfate, cobalt acetate, cobaltous bromide, cobaltous chloride, zinc acetate, zinc bromide, zinc formate, zinc iodide, zinc sulfate heptahydrate, magnesium acetate, magnesium bromide, magnesium chloride, magnesium iodide, magnesium nitrate, magnesium sulfate, manganous acetate, manganous bromide, manganous sulfate, and the like While not essential to the synthesis of MeAPO compositions, it has been found that in general, stirring or other moderate agitation of the reaction mixture and/or seeding the reaction mixture with seed crystals of either the MeAPO species to be produced or a topologically similar aluminophosphate or aluminosilicate composition, facilitates the crystallization procedure.

After crystallization the MeAPO product is isolated and advantageously washed with water and dried in air. The as-synthesized MeAPO contains within its internal pore system at least one form of the templating agent employed in its formation. Most commonly the organic moiety is present, at least in part, as a charge balancing cation as is generally the case with as-synthesized aluminosilicate zeolites prepared from organic-containing reaction systems. It is possible, however, that some or all of the organic moiety is an occluded molecular species in a particular MeAPO species. As a general rule, the templating agent, and hence the occluded organic species, is too large to move freely through the pore system of the MeAPO product and must be removed by calcining the MeAPO at temperatures of 200° C. to 700° C. to thermally degrade the organic species. In a few instances the pores of the MeAPO product are sufficiently large to permit transport of the templating agent, particularly if the latter is a small molecule, and accordingly complete or partial removal thereof can be accomplished by conventional desorption procedures such as carried out in the case of zeolites. It will be understood that the term "as-synthesized" as used herein does not include the condition of the MeAPO phase wherein the organic moiety occupying the intracrystalline pore system as a result of the hydrothermal crystallization process has been reduced by post synthesis treatment such that the value of "m" in the composition formula:

$$mR: (M_xAl_yP_z)O_2$$

has a value of less than 0.02. The other symbols of the formula are as defined hereinabove. In those preparations in which an aluminum alkoxide is employed as the source of aluminum, the corresponding alcohol is necessarily present in the reaction mixture since it is a hydrolysis product of the alkoxide. It has not been determined whether this alcohol participates in the synthesis process as a templating agent. For the purposes of this application, however, this alcohol is arbitrarily omitted from the class of templating agents, even if it is present in the as synthesized MeAPO material.

Since the MeAPO compositions are formed from $AlO_2$, $PO_2$, and $MO_2$ tetrahedral units which, respectively, have a net charge of $-1$, $+1$, and $-2$, the matter of cation exchangeability is considerably more complicated than in the case of zeolitic molecular sieves in which, ideally, there is a stoichiometric relationship between $AlO_2$ tetrahedra and charge balancing cations. In the MeAPO compositions, an $AlO_2^-$ tetrahedron can be balanced electrically either by association with a $PO_2^+$ tetrahedron or a simple cation such as an alkali metal cation, a cation of the metal "M" present in the reaction mixture, or an organic cation derived from the templating agent. Similarly an $MO_1^{-2}$ tetrahedron can be balanced electrically by association with $PO_2^+$ tetrahedra, a cation of the metal "M", organic cations derived from the templating agent, or other divalent or polyvalent metal cations introduced from an extraneous source. It has also been postulated that non adjacent $AlO_2^-$ and $PO_2^+$ tetrahedral pairs can be balanced by $Na^+$ and $OH^-$, respectively [Flanigen and Grose, Molecular Sieve Zeolites I, ACS, Washington, D.C. (1971)].

FAPO MOLECULAR SIEVES

Ferroaluminophosphates are disclosed in U.S. Pat. No. 4,554,143, incorporated herein by reference, and have a three-dimensional microporous crystal framework structure of $AlO_2^-$, $FeO_2^n$, and $PO_3^+$ tetrahedral units, where "n" is $-2$ or $-1$, and have an essential empirical chemical composition, or an anhydrous basis, of:

$$mR:(Fe_xAl_yP_z)O_2$$

wherein "R" represents at least one organic templating agent present in the intracrystalline pore system; "m" represents the moles of "R" present per mole of $(Fe_xAl_yP_z)O_2$ and has a value of from zero to 0.3 maximum value in each case depending upon the molecular dimensions of the templating agent and the available void volume of the pore system of the particular ferroaluminophosphate involved; "x", "y" and "z" represent the mole fraction of iron, aluminum and phosphorus, respectively, present as tetrahedral oxides, representing the following values for "x", "y" and "z":

| Point | Mole Fraction | | |
|---|---|---|---|
| | x | y | z |
| A | 0.01 | 0.60 | 0.39 |
| B | 0.01 | 0.39 | 0.60 |
| C | 0.35 | 0.05 | 0.60 |
| D | 0.35 | 0.60 | 0.05 |

When synthesized the minimum value of "m" in the formula above is 0.02. In a preferred subclass of the ferroaluminophosphates the values of "x", "y" and "z" in the formula above are representing the following values for "x", "y" and "z":

| Point | Mole Fraction | | |
|---|---|---|---|
| | x | y | z |
| a | 0.01 | 0.52 | 0.47 |
| b | 0.01 | 0.39 | 0.60 |
| c | 0.25 | 0.15 | 0.60 |
| d | 0.25 | 0.40 | 0.35 |

The iron of the $FeO_2$ structural units can be in either the ferric or ferrous valence state, depending largely upon the source of the iron in the synthesis gel. Thus, an $FeO_2$ tetrahedron in the structure can have a net charge of either $-1$ or $-2$. While it is believed that the Fe, Al and P framework constituents are present in tetrahedral coordination with oxygen (and are referred to herein as such), it is theoretically possible that some minor fraction of these framework constituents are present in coordination with five or six oxygen atoms. It is not, moreover, necessarily the case that all of the Fe, Al and/or P content of any given synthesized product is a part of the framework in the aforesaid types of coordination with oxygen. Some of each constituent may be merely occluded or in some as yet undetermined form, and may or may not be structurally significant.

For convenience in describing the ferroaluminophosphates, the "short hand" acronym "FAPO" is sometimes employed hereinafter. To identify the various structural species which make up the generic class FAPO, each species is assigned a number and is identified, for example, as FAPO-11, FAPO-31 and so forth.

The term "essential empirical chemical composition" is meant to include the crystal framework and can include any organic templating agent present in the pore system, but does not include alkali metal or other ions which can be present by virtue of being contained in the reaction mixture or as a result of post-synthesis ion exchange. Such ionic species, when present, function primarily as charge balancing ions for $FeO_2^-$ and/or $AlO_2^{-2}$ tetrahedra, $FeO_2^{-2}$ tetrahedra associated with $PO_2^+$ tetrahedra or not associated with $PO_2^+$ tetrahedra or an organic ion derived from the organic templating agent.

The aforesaid ferroaluminophosphates are synthesized by hydrothermal crystallization from a reaction mixture containing reactive sources of iron oxide, alumina, and phosphate, an organic templating, i.e., structure directing, agent, preferably a compound of an element of Group VA of the Periodic Table, and optionally an alkali metal. The reaction mixture is placed in a sealed pressure vessel, preferably lined with an inert plastic material such as polytetrafluoroethylene and heated, preferably under autogenous pressure at a temperature of at least 100° C., and preferably between 100° C. and 250° C., until crystals of the metal aluminophosphate product are obtained, usually a period of from 2 hours to 2 weeks. The product is recovered by any convenient method such as centrifugation or filtration.

In synthesizing the FAPO compositions, it is preferred to employ a reaction mixture composition expressed in terms of molar ratios as follows:

$$aR: (Fe_xAl_yP_z)O_2 \ bH_2O$$

wherein "R" is an organic templating agent; "a" has a value great enough to constitute an effective concentration of "R" and is within the range of $>0$ to 6; "b" has a value of from zero to 500, preferably 2 to 80; "x", "y" and "z" represent the mole fractions, respectively, of iron, aluminum and phosphorus in the $(Fe_xAl_yP_z)O_2$ constituent, and each has a value o at least 0.01, and representing the following values for "x", "y" and "z":

| Point | Mole Fraction | | |
|---|---|---|---|
| | x | y | z |
| E | 0.01 | 0.70 | 0.29 |
| F | 0.01 | 0.29 | 0.70 |
| G | 0.29 | 0.01 | 0.70 |
| H | 0.40 | 0.01 | 0.59 |
| I | 0.40 | 0.59 | 0.01 |

| Point | Mole Fraction | | |
|---|---|---|---|
| | x | y | z |
| J | 0.29 | 0.70 | 0.01 |

In the foregoing expression of the reaction composition, the reactants are normalized with respect to a total of $(Fe+Al+P)=(x+y+z)=1.00$ mole.

In forming the reaction mixture from which the ferroaluminophosphates are crystallized, the organic templating agent can be any of those heretofore proposed for use in the synthesis of conventional zeolite aluminosilicates and microporous aluminophosphates. In general these compounds contain elements of Group VA of the Periodic Table of Elements, particularly nitrogen, phosphorus, arsenic and antimony, preferably N or P and most preferably N, which compounds also contain at least one alkyl or aryl group having from 1 to 8 carbon atoms. Particularly preferred nitrogen containing compounds for use as templating agents are the amines and quaternary ammonium compounds, the latter being represented generally by the formula $R_4N^{30}$ wherein each R is an alkyl or aryl group containing from 1 to 8 carbon atoms. Polymeric quaternary ammonium salts such as $[C_{14}H_{32}N_2)(OH)_2]_x$ wherein "x" has a value of at least 2 are also suitably employed. Mono-, di- and triamines are advantageously utilized, either alone or in combination with a quaternary ammonium compound or other templating compound. Mixtures of two or more templating agents can either produce mixtures of the desired metal aluminophosphates or the more strongly directing templating species may control the course of the reaction with the other templating species serving primarily to establish the pH conditions of the reaction gel. Representative templating agents include tetramethylammonium, tetraethylammonium, tetrapropylammonium or tetrabutylammonium ions; di-n-propylamine; tri-n-propylamine; triethylamine; triethanolamine; piperidine; cyclohexylamine; 2-methylpyridine; N,N-dimethylbenzylamine; N-N-diemethylethanolamine; choline; N,N'-diemthylpiperazine; 1,4 diazabicyclo (2,2,2) octane; N-methyldiethanolamine; N-methylethanolamine; N-methylpiperidine; 3-methylpiperidine; N-methylcyclohexylamine; 3-methylpyridine; 4-methylpyridine; quinuclidine; N,N'-dimethyl 1,4-diazabicyclo (2,2,2) octane ion; di-n-butylamine; neopentylamine; di-n-pentylamine; isopropylamine; t-butylamine; ethylenediamine; pyrrolidine; and 2-imidazolidone. Not every templating agent will direct the formation of every species of ferroaluminophosphate (FAPO), i.e., a single templating agent can, with proper manipulation of the reaction conditions, direct the formation of several FAPO compositions, and a given FAPO composition can be produced using several different templating agents.

The phosphorus source is preferably phosphoric acid, but organic phosphates such as triethylphosphate have been found satisfactory, and so also have crystalline or amorphous aluminophosphates such as the $AlPO_4$ composition of U.S. Pat. No. 4,310,440. Organo-phosphorus compounds, such as tetrabutylphosphonium bromide do not, apparently serve as reactive sources of phosphorus, but these compounds do function as templating agents. Conventional phosphorus salts such as sodium metaphosphate, may be used, at least in part, as the phosphorus source, but are not preferred.

The aluminum source is preferably either an aluminum alkoxide, such as aluminum isopropoxide, or pseudoboehmite. The crystalline or amorphous aluminophosphates which are a suitable source of phosphorus are, of course, also suitable sources of aluminum. Other sources of aluminum used in zeolite synthesis, such as gibbsite, sodium aluminate and aluminum trichloride, can be employed but are not preferred.

Iron can be introduced into the reaction system in any form which permits the formation in situ of reactive ferrous or ferric ions. Advantageously iron salts, oxides or hydroxides are employed such as iron sulfate, iron acetate, iron nitrate, or the like. Other sources such as a freshly precipitated iron oxide $\tau$-FeOOH, are also suitable.

While not essential to the synthesis of FAPO compositions, it has been found that in general, stirring or other moderate agitation of the reaction mixture and/or seeding the reaction mixture with seed crystals of either the FAPO species to be produced or a topologically similar aluminophosphate or aluminosilicate composition, facilitates the crystallization procedure.

After crystallization the FAPO product is isolated and advantageously washed with water and dried in air. The as-synthesized FAPO contains within its internal pore system at least one form of the templating agent employed in its formation. Most commonly the organic moiety is present, at least in part, as a charge balancing cation as is generally the case with as synthesized aluminosilicate zeolites prepared from organic containing reaction systems. It is possible, however, that some or all of the organic moiety is an occluded molecular species in a particular FAPO species. As a general rule, the templating agent, and hence the occluded organic species, is too large to move freely through the pore system of the FAPO product and must be removed by calcining the FAPO at temperatures of 200° C. to 700° C. to thermally degrade the organic species. In a few instances the pores of the FAPO product are sufficiently large to permit transport of the templating agent, particularly if the latter is a small molecule, and accordingly complete or partial removal thereof can be accomplished by conventional desorption procedures such as carried out in the case of zeolites. It will be understood that the term "as synthesized" as used herein and in the claims does not include the condition of the FAPO phase wherein the organic moiety occupying the intracrystalline pore system as a result of the hydrothermal crystallization process has been reduced by post synthesis treatment such at the value of "m" in the composition formula:

$$mR:(Fe_xAl_yP_z)O_2$$

has a value of less than 0.02. The other symbols of the formula are as defined hereinabove. In those preparations in which an aluminum alkoxide is employed as the source of aluminum, the corresponding alcohol is necessarily present in the reaction mixture since it is a hydrolysis product of the alkoxide. It has not been determined whether this alcohol participates in the syntheses process as a templating agent. For the purposes of this application, however, this alcohol is arbitrarily omitted from the class of templating agents, even if it is present in the as synthesized FAPO material.

Since the FAPO compositions are formed from $AlO_2^-$, $PO_2^+$, $FeO_2^-$ and/or $FeO_2^{-2}$ units the matter of cation exchangeability is considerably complicated than in the case of zeolitic molecular sieves in which, ideally, there is a stoichiometric relationship between AlO₂ tetrahedra and charge balancing cations. In the FAPO compositions, an $AlO_2^-$ tetrahedron can be balanced electrically either by association with a $PO_2^+$ tetrahedron or a simple cation such as alkali metal cation, a $Fe^{+2}$ or $Fe^{+3}$ cation present in the reaction mixture, or an organic cation derived from the templating agent. Similarly an $FeO_2^-$ or $FeO_2^{-2}$ tetrahedron can be balanced electrically by association with $PO_2$ tetrahedron, a $Fe^{+2}$ or $Fe^{+3}$ cation, organic cations derived from the templating agent, or other metal cation introduced from an extraneous source. It has also been postulated that non-adjacent $AlO_2^-$ and $PO_2^+$ tetrahedral pairs can be balanced by $Na^+$ and $OH^-$, respectively [Flanigen and Grose, Molecular Sieve Zeolites I, ACS, Washington, D.C. (1971)].

TAPO MOLECULAR SIEVES

TAPO molecular sieves are disclosed in U.S. Pat. No. 4,500,561, incorporated herein by reference, and comprise a three-dimensional microporous crystal framework structure of $TiO_2$, $AlO_2^-$ and $PO_3^+$ tetrahedral units which has a unit empirical formula on an anhydrous basis of:

$$mR:(Ti_xAl_yP_z)O_2$$

wherein "R" represents at least one organic templating agent present in the intracrystalline pore system; "m" represents the moles of "R" present per mole of $(Ti_xAl_yP_z)O_2$ and has a value of between zero and a 5.0, the maximum value in each case depending upon the molecular dimensions of the templating agent and the available void volume of pore system of the particular titanium molecular sieve; "x", "y" and "z" represent the mole fractions of titanium, aluminum and phosphorus, respectively, present as tetrahedral oxides, representing the following values for "x", "y" and "z":

| Point | Mole Fraction | | |
|---|---|---|---|
| | x | y | z |
| A | 0.001 | 0.45 | 0.549 |
| B | 0.88 | 0.01 | 0.11 |
| C | 0.98 | 0.01 | 0.01 |
| D | 0.29 | 0.70 | 0.01 |
| E | 0.001 | 0.70 | 0.299 |

The parameters "x", "y" and "z" are preferably within the following values for "x", "y" and "z":

| Point | Mole Fraction | | |
|---|---|---|---|
| | x | y | z |
| a | 0.002 | 0.499 | 0.499 |
| b | 0.20 | 0.40 | 0.40 |
| c | 0.20 | 0.50 | 0.30 |
| d | 0.10 | 0.60 | 0.30 |
| e | 0.002 | 0.60 | 0.398 |

The titanium-containing molecular sieves are referred to hereinafter, solely for point of reference herein as "TAPO" molecular sieves, or as "TAPOs" if the reference is to the class as a whole. This designation is simple made for the sake of convenient reference herein and is not meant to designate a particular structure for any given TAPO molecular sieve. The members of the class of TAPO's employed hereinafter in the examples will be characterized simply by referring to such members as TAPO-5, TAPO-11, etc., i.e., a particular species will be referred to as TAPO n where "n" is a number specific to a given class member as its preparation is reported herein. This designation is an arbitrary one and is not intended to denote structural relationship to another material(s) which may also be characterized by a numbering system.

The term "unit empirical formula" is used herein according to its common meaning to designate the simplest formula which gives the relative number of moles of titanium, aluminum and phosphorus which form the $[TiO_2]$, $[PO_2]$ and $[AlO_2]$ tetrahedral unit within a titanium containing molecular sieve and which forms the molecular framework of the TAPO composition(s). The unit empirical formula is given in terms of titanium, aluminum and phosphorus as shown in Formula (1), above, and does not include other compounds, cations or anions which may be present as a result of the preparation or the existence of other impurities or materials in the bulk composition not containing the aforementioned tetrahedral unit. The amount of template R is reported as part of the composition when the as synthesized unit empirical formula is given, and water may also be reported unless such is defined as the anhydrous form. For convenience, coefficient "m" for template "R" is reported as a value that is normalized by dividing the number of moles of organic templating agent by the total moles of titanium, aluminum and phosphorus.

The unit empirical formula for a TAPO may be given on an "as synthesized" basis or may be given after an "as synthesized" TAPO composition has been subjected to some post treatment process, e.g., calcination. The term "as synthesized" herein shall be used to refer to the TAPO composition(s) formed as a result of the hydrothermal crystallization but before the TAPO composition has been subjected to post treatment to remove any volatile components present therein. The actual value of "m" for a post treated TAPO will depend on several factors (including: the particular TAPO, template, severity of the post treatment in terms of its ability to remove the template from the TAPO, the proposed application of the TAPO composition, and etc.) and the value for "m" can be within the range of values as defined for the as synthesized TAPO compositions although such is generally less than the as synthesized TAPO unless such post-treatment process adds template to the TAPO so treated. A TAPO composition which is in the calcined or other post treatment form generally has an empirical formula represented by Formula (1), except that the value of "m" is generally less than about 0.02. Under sufficiently severe post treatment conditions, e.g., roasting in air at high temperature for long periods (over 1 hr.), the value of "m" may be zero (0) or, in any event, the template, R, is undetected by normal analytical procedures.

The TAPO molecular sieves are generally further characterized by an intracrystalline adsorption capacity for water at 4.6 torr and about 24° C. of about 3.0 weight percent. The adsorption of water has been observed to be completely reversible while retaining the same essential framework topology in both the hydrated and dehydrated state. The term "essential framework topology" is meant to designate the spatial arrangement of the primary bond linkages. A lack of change in the framework topology indicates that there is no disruption of these primary bond linkages.

The TAPO molecular sieves are generally synthesized by hydrothermal crystallization from a reaction mixture comprising reactive sources of titanium, aluminum and phosphorus, and one or more organic templating agents. Optionally, alkali metal(s) may be present in the reaction mixture. The reaction mixture is placed in a pressure vessel, preferably lined with an inert plastic material, such as polytetrafluoroethylene, and heated, preferably under autogenous pressure, at a temperature of at least about 100° C., and preferably between 100° C. and 250° C., until crystals of the molecular sieve product are obtained, usually for a period of from 2 hours to 2 weeks. While not essential to the synthesis of the TAPO molecular sieves, it has been found that in general stirring or other moderate agitation of the reaction mixture and/or seeding the reaction mixture with seed crystals of either the TAPO to be produced, or a topologically similar composition, facilitates the crystallization procedure. The product is recovered by any convenient method such as centrifugation or filtration.

After crystallization the TAPO(s) may be isolated and washed with water and dried in air. As a result of the hydrothermal crystallization, the as synthesized TAPO contains within its intracrystalline pore system at least one form of the template employed in its formation. Generally, the template is a molecular species, but it is possible, steric considerations permitting, that at least some of the template is present as a charge-balancing cation. Generally the template is too large to move freely through the intracrystalline pore system of the formed TAPO and may be removed by a post treatment process, such as by calcining the TAPO a temperatures of between about 200° C. and to about 700° C. so as to thermally degrade the template or by employing some other post treatment process for removal of at least part of the template from the TAPO. In some instances the pores of the TAPO are sufficiently large to permit transport of the template, and, accordingly, complete or partial removal thereof can be accomplished by conventional desorption procedures such as carried out in the case of zeolites.

The TAPOs are preferably formed from a reaction mixture having a mole fraction of alkali metal cation which is sufficiently low that it does not interfere with the formation of the TAPO composition. The TAPO compositions are generally formed from a reaction mixture containing reactive sources of $TiO_2$, $Al_2O_3$, and $P_2O_5$ and an organic templating agent, said reaction mixture comprising a composition expressed in terms of molar oxide ratios of:

$fR_2O:(Ti_xAl_yP_z)O_2:g\ H_2O$ wherein "R" is an organic templating agent; "f" has a value large enough to constitute an effective amount of "R", said effective amount being that amount which form said TAPO compositions; "g" has a value of from zero to 500; "x", "y" and "z" represent the mole fractions, respectively of titanium, aluminum and phosphorus in the $(Ti_xAl_yP_z)O_2$ constituent, and each has a value of at least 0.001 and being within the following values for "x", "y" and "z":

| Point | Mole Fraction | | |
|---|---|---|---|
| | x | y | z |
| h | 0.001 | 0.989 | 0.01 |
| i | 0.001 | 0.01 | 0.989 |
| j | 0.32 | 0.24 | 0.44 |
| k | 0.98 | 0.01 | 0.01 |

Although the TAPO compositions will form if higher concentrations of alkali metal cation are present, such reaction mixtures are not generally preferred. A reaction mixture, expressed in terms of molar oxide ratios, comprising the following bulk composition is preferred.

$oR_2O:wM_2O:(Ti_xAl_yP_z)O_2:nH_2O$ wherein "R" is an organic template; "o" has a value great enough to constitute an effective concentration of "R" and is preferably within the range of from greater than zero (0) to about 5.0; "M" is an alkali metal cation; "w" has a value of from zero to 2.5; "n" has a value between about zero (0) and about 500; "x", "y" and "z" represent the mole fractions, respectively, of titanium, aluminum and phosphorus in the $(Ti_xAl_yP_z)O_2$ constituent, and each has a value of at least 0.001 and being within the following values for "x", "y" and "z":

| Point | Mole Fraction | | |
|---|---|---|---|
| | x | y | z |
| h | 0.001 | 0.989 | 0.01 |
| i | 0.001 | 0.01 | 0.989 |
| j | 0.32 | 0.24 | 0.44 |
| k | 0.98 | 0.01 | 0.01 |

When the TAPOs are synthesized by this method the value of "m" in Formula (1) is generally above about 0.02.

Though the presence of alkali metal cations is not preferred, when they are present in the reaction mixture it is preferred to first admix at least a portion (e.g., at least about 10 weight percent) of each of the aluminum and phosphorus sources in the substantial absence (e.g., preferably less than about 20 percent of the total weight of the aluminum source and phosphorus source) of the titanium source. This procedure avoids adding the phosphorus source to a basic reaction mixture containing the titanium source and aluminum source, (as was done in most of the published attempts to substitute isomorphously $[PO_2]$ tetrahedra for $[SiO_2]$ tetrahedra in zeolitic structures). Although the reaction mechanism is by no means clear favor the incorporation of $[PO_2]$ and $[AlO_2]$ tetrahedra in the framework structures of the crystalline products with $[TiO_2]$ tetrahedra isomorphously replacing $[PO_2]$ tetrahedra.

The reaction mixture from which these TAPOs are formed contains one or more organic templating agents (templates) which can be most any of those heretofore proposed for use in the synthesis of aluminosilicates and aluminophosphates. The template preferably contains at least one element of Group VA of the Periodic Table, particularly nitrogen, phosphorus, arsenic and/or antimony, more preferably nitrogen or phosphorus and most preferably nitrogen and is desirably of the formula $R_4X^+$ wherein X is selected from the group consisting of nitrogen, phosphorus, arsenic and/or antimony and R may be hydrogen, alkyl, aryl, aralkyl, or alkylaryl group and is preferably aryl or alkyl containing between 1 and 8 carbon atoms, although more than eight carbon atoms may be present in the group "R" of the template. Nitrogen containing templates are preferred, including amines and quaternary ammonium compounds, the latter being represented generally by the formula R'$_4$N+ wherein each R' is an alkyl, aryl, alkylaryl, or aralkyl group; wherein R preferably contains from 1 to 8 carbon atoms or higher when R' is alkyl and greater than 6 carbon atoms when R' is otherwise, as hereinbefore discussed. Polymeric quaternary ammonium salts such as [(C$_{14}$H$_{32}$N$_2$)(OH)$_2$]$_x$ wherein "x" has a value of at least 2 may also be employed. The mono , di-and triamines, including mixed amines, may also be employed as templates either alone or in combination with a quaternary ammonium compound or another template. The exact relationship of various templates when concurrently employed is not clearly understood. Mixtures of two or more templating agents can produce either mixtures of TAPOs or in the instance where one template is more strongly directing than another template the more strongly directing template may control the course of the hydrothermal crystallization wherein with the other template serving primarily to establish the pH conditions of the reaction mixture.

Representative templates include tetramethylammonium, tetraethylammonium, tetrapropylammonium or tetrabutylammonium ions; di n-propylamine; tripropylamine; triethylamine; triethanolamine; piperidine; cyclohexylamine; 2-methylpyridine; N,N-dimethylbenzylamine; N,N-diethylethanolamine; dicyclohexylamine; N,N-dimethylethanolamine; 1,4-diazabicyclo (2,2,2) octane; N-methyldiethanolamine, N-methyl ethanolamine; N-methylcyclohexylamine; 3-methylpyridine; 4-methylpyridine; quinuclidine; N,N'-dimethyl-1,4-diazabicyclo (2,2,2) octane ion; di-n-butylamine; neopentylamine; di-n-pentylamine; isopropylamine; t-butylamine; ethylenediamine; pyrrolidine; and 2-imidazolidone. Not every template will produce every TAPO composition although a single template can, with proper selection of the reaction conditions, cause the formation of different TAPO compositions, and a given TAPO composition can be produced using different templates.

In those instances where an aluminum alkoxide is the reactive aluminum source, the corresponding alcohol is necessarily present in the reaction mixture since it is a hydrolysis product of the alkoxide. It has not as yet been determined whether this alcohol participates in the synthesis process as a templating agent, or in some other function and, accordingly, is not reported as a template in the unit formula of the TAPOs, although such may be acting as templates.

Alkali metal cations, if present in the reaction mixture, may facilitate the crystallization of certain TAPO phases, although the exact function of such cations, when present, in crystallization, if any, is not presently known. Alkali cations present in the reaction mixture generally appear in the formed TAPO composition, either as occluded (extraneous) cations and/or as structural balancing net negative charges at various sites in the crystal lattice. It should be understood that although the unit formula for the TAPOs does not specifically recite the presence of alkali cations they are not excluded in the same sense that hydrogen cations and/or hydroxyl groups are not specifically provided for in the traditional formulae for zeolitic aluminosilicates.

Almost any reactive titanium source may be employed herein. The preferred reactive titanium sources include titanium alkoxides, water-soluble titanates and titanium chelates.

Almost any reactive phosphorus source may be employed. Phosphoric acid is the most suitable phosphorus source employed to date. Accordingly, other acids of phosphorus are generally believed to be suitable phosphorus sources for use herein. Organic phosphates such as triethyl phosphate have been found satisfactory, and so also have crystalline or amorphous aluminophosphates such as the AlPO$_4$ compositions of U.S. Pat. No. 4,310,440. Organo-phosphorus compounds, such as tetrabutyl-phosphonium bromide have not, apparently, served as reactive sources of phosphorus, but these compounds do function as templating agents and may also be capable of being suitable phosphorus sources under proper process conditions (yet to be ascertained). Organic phosphorus compounds, e.g., esters, are believed to be generally suitable since they can generate acids of phosphorus in situ. Conventional phosphorus salts, such as sodium metaphosphate, may be used, at least in part as the phosphorus source, but they are not preferred.

Almost any reactive aluminum source may be employed herein. The preferred reactive aluminum sources include aluminum alkoxides, such as aluminum isopropoxide, and pseudoboehmite. Crystalline or amorphous aluminophosphates which are a suitable source of phosphorus are, of course, also suitable sources of aluminum. Other sources of aluminum used in zeolite synthesis, such as gibbsite, sodium aluminate and aluminum trichloride, can be employed but as generally not preferred.

Since the exact nature of the TAPO molecular sieves are not clearly understood at present, although all are believed to contain [TiO$_2$] tetrahedra in the three dimensional microporous crystal framework structure, it is advantageous to characterize the TAPO molecular sieves by means of their chemical composition. This is due to the low level of titanium present in certain of the TAPO molecular sieves prepared to date which makes it difficult to ascertain the exact nature of the interaction between titanium, aluminum and phosphorus. As a result, although it is believed that titanium, [TiO$_2$], has substituted isomorphously for [AlO$_2$] or [PO$_2$] tetrahedra, it is appropriate to characterize certain TAPO compositions by reference to their chemical composition in terms of the mole ratios of oxides in the as synthesized and anhydrous form as:

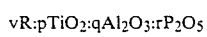

$$vR:pTiO_2:qAl_2O_3:rP_2O_5$$

wherein "R" represents at least one organic templating agent present in the intracrystalline pore system; "v" represents an effective amount of the organic templating agent to form said TAPO compositions and preferably has a value between and including zero and about 3.0; "p", "q" and "r" represent moles, respectively, of titanium, alumina and phosphorus pentoxide, based on said moles being such that they are within the following values for "p", "q" and "r":

| Point | Mole Fraction | | |
|---|---|---|---|
| | p | q | r |
| A | 0.004 | 1.0 | 1.22 |
| B | 176 | 1.0 | 11.0 |
| C | 196 | 1.0 | 1.0 |
| D | 0.828 | 1.0 | 0.0143 |

| | Mole Fraction | | |
|---|---|---|---|
| Point | p | q | r |
| E | 0.003 | 1.0 | 0.427 |

The parameters "p", "q" and "r" are preferably within the following values for "p", "q" and "r":

| | Mole Fraction | | |
|---|---|---|---|
| Point | p | q | r |
| a | 0.008 | 1.0 | 1.0 |
| b | 1.0 | 1.0 | 1.0 |
| c | 0.80 | 1.0 | 0.60 |
| d | 0.333 | 1.0 | 0.50 |
| e | 0.067 | 1.0 | 0.663 |

ELAPO MOLECULAR SIEVES

"ELAPO" molecular sieves are a class of crystalline molecular sieves in which at least one element capable of forming a three dimensional microporous framework forms crystal framework structures of $AlO_2^-$, $PO_2^+$ and $MO_2^n$ tetrahedral oxide units wherein "$MO_2^n$" represents at least one different element (other than Al or P) present as tetrahedral oxide units "$MO_2^n$" with charge "n" where "n" may be $-3$, $-2$, $-1$, 0 or $+1$. The members of this novel class of molecular sieve compositions have crystal framework structures of $AlO_2^-$, $PO_2^+$ and $MO_2^n$ tetrahedral units and have an empirical chemical composition on an anhydrous basis expressed by the formula:

$$mR:(M_xAl_yP_z)O_2$$

wherein "R" represents at least one organic templating agent present in the intracrystalline pore system; "m" represents the molar amount of "R" present per mole of $(M_xAl_yP_z)O_2$; "M" represents at least on e capable of forming framework tetrahedral oxides; and "x", "y" and "z" represent the mole fraction of "M", aluminum and phosphorus, respectively, present as tetrahedral oxides. "M" is at least one different (i.e., not aluminum, phosphorus or oxygen) element such that the molecular sieves contain at least one framework tetrahedral unit in addition to $AlO_2^-$  and $PO_2^+$. "M" is at least one element selected from the group consisting of arsenic, beryllium, boron, cobalt, chromium, gallium, germanium, iron, lithium, magnesium, manganese, titanium and zinc, subject to certain restrictions on the combinations of elements as will appear from the discussions of individual groups of ELAPOs below. ELAPOs and their preparation are disclosed in European Patent Application Ser. Nos. 85104386 9, filed Apr. 11, 1985 (EPC Publication No. 0158976, published Oct. 13, 1985, incorporated herein by reference) and 85104388.5, filed Apr. 11, 1985 (EPC Publication No. 158349, published Oct. 16, 1985, incorporated herein by reference).

The "ELAPO" molecular sieves further include numerous species which are intended herein to be within the scope of the term "non zeolitic molecular sieves" such being disclosed in the following copending and commonly assigned applications, incorporated herein by reference thereto [(A) following a serial number indicates that the application is abandoned, while (CIP) following a serial number indicates that the application is a continuation-in-part of the immediately preceding application, and (C) indicates that the application is a continuation of the immediately preceding application]:

| U.S. Ser. No. | Filed | NZMS |
|---|---|---|
| 600,166(A) | April 13, 1984 | AsAPO |
| 830,889(CIP) | Feb. 19, 1986 | AsAPO |
| 599,812(A) | April 13, 1984 | BAPO |
| 804,248(C)(A) | Dec. 4, 1985 | BAPO |
| 029,540(CIP) | March 24, 1987 | BAPO |
| 599,776(A) | April 13, 1984 | BeAPO |
| 835,293(CIP) | March 3, 1986 | BeAPO |
| 599,813(A) | April 13, 1984 | CAPO |
| 830,756(CIP) | Feb. 19, 1986 | CAPO |
| 599,771(A) | April 13, 1984 | GaAPO |
| 830,890(CIP) | Feb. 19, 1986 | GaAPO |
| 599,807(A) | April 13, 1984 | GeAPO |
| 841,753(CIP) | March 20, 1986 | GeAPO |
| 599,811(A) | April 13, 1984 | LiAPO |
| 834,921(CIP) | Feb. 28, 1986 | LiAPO |
| 600,171 | April 13, 1984 | FCAPO |
| (now U.S. Pat. No. 4,686,093 issued August 11, 1987) | | |
| 600,172(A) | April 13, 1984 | ElAPO (M comprises two different elements) |
| 846,088(CIP) | March 31, 1986 | |
| 599,824(A) | April 13, 1984 | FeTiAPO |
| 902,129(C) | September 2, 1986 | FeTiAPO |
| 599,810(A) | April 13, 1984 | XAPO |
| 902,020(C) | September 2, 1986 | XAPO |

The ELAPO molecular sieves are generally referred to herein by the acronym "ELAPO" to designate element(s) "M" in a framework of $AlO_2^-$, $PO_2^+$ and $MO_2^n$ tetrahedral oxide units. Actual class members will be identified by replacing the "EL" of the acronym with the elements present as $MO_2^n$ tetrahedral units. For example, "MgBeAPO" designates a molecular sieve comprised of $AlO_2^-$, $PO_2^+$, $MgO_2^{-2}$ and $BeO_2^{-2}$ tetrahedral units. To identify various structural species which make up each of the subgeneric classes, each species is assigned a number and is identified as "ELAPO-i" wherein "i" is an integer. The given species designation is not intended to denote a similarity in structure to any other species denominated by a similar identification system.

The ELAPO molecular sieves comprise at least one additional element capable of forming framework tetrahedral oxide units $(MO_2^n)$ to form crystal framework structures with $AlO_2^-$ and $PO_2^+$ tetrahedral oxide units wherein "M" represents at least one element capable of forming tetrahedral units "$M_2^n$" where "n" is $-3$, $-2$, $-1$, 0 or $+1$ and is at least one element selected from the group consisting of arsenic, beryllium, boron, cobalt, chromium, gallium, germanium, iron, lithium, magnesium, manganese, titanium and zinc.

The ELAPO molecular sieves have crystalline three dimensional microporous framework structures of $AlO_2^-$, $PO_2^+$ and $MO_2^n$ tetrahedral units and have an empirical chemical composition on an anhydrous basis expressed by the formula:

$$mR:(M_xAl_yP_z)O_2;$$

wherein "R" represents at leas one organic templating agent present in the intracrystalline pore system; "m" represents the molar amount of "R" present per mole of $(M_xAl_yP_z)O_2$ and has a value of zero to about 0.3; "M" represents at least one element capable of forming framework tetrahedral oxides where "M" is at least one element selected from the group consisting of arsenic, beryllium, boron, cobalt, chromium, gallium, germanium, iron, lithium, magnesium, manganese, titanium and zinc.

The relative amounts of element(s) "M", aluminum and phosphorous are expressed by the empirical chemical formula (anhydrous):

$$mR:(M_xAl_yP_z)O_2$$

where "x", "y" and "z" represent the mole fractions of said "M" aluminum and phosphorous. The individual mole fractions of each "M" (or when M denotes two or more elements, $M_1$, $M_2$, $M_3$, etc.) may be represented by "$x_1$", "$x_2$", "$x_3$", etc. wherein "$x_1$", "$x_2$", and "$x_3$" etc. represent the individual mole fractions of elements $M_1$, $M_2$, $M_3$, and etc. for "M" as above defined. The values of "$x_1$", "$x_2$", "$x_3$", etc. are as defined for "x", hereinafter, where "$x_1$" + "$x_2$" + "$x_3$" ... = "x" and where $x_1$, $x_2$, $x_3$, etc. are each at least 0.01.

The ELAPO molecular sieves have crystalline three dimensional microporous framework structures of $MO_2^n$, $AlO_2^-$ and $PO_2^+$ tetrahedral units having an empirical chemical composition on an anhydrous basis expressed by the formula:

$$mR:(M_xAl_yP_z)O_2$$

wherein "R" represents at least one organic templating agent present in the intracrystalline pore system; "m" represents a molar amount of "R" present per mole of $(M_xAl_yP_z)O_2$ and has a value of zero to about 0.3; "M" represents at least one different element (other than Al or P) capable of forming framework tetrahedral oxides, as hereinbefore defined, and "x", "y" and "z" represent the mole fractions of "M", aluminum and phosphorous, respectively present as tetrahedral oxides; in general, said mole fractions "x", "y" and "z" are within the following values for "x", "y" and "z", although as will appear hereinbelow, the limits for "x", "y" and "z" may vary slightly with the nature of the element "M":

| Point | Mole Fraction | | |
|---|---|---|---|
| | x | y | z |
| A | 0.02 | 0.60 | 0.38 |
| B | 0.02 | 0.38 | 0.60 |
| C | 0.39 | 0.01 | 0.60 |
| D | 0.98 | 0.01 | 0.01 |
| E | 0.39 | 0.60 | 0.01 |

Also, in general, in a preferred sub-class of the ELAPOs of this invention, the values of "x", "y" and "z" in the formula above are within the following values for "x", "y" and "z", although again the relevent limits may vary somewhat with the nature of the element "M", as set forth hereinbelow:

| Point | Mole Fraction | | |
|---|---|---|---|
| | x | y | z |
| a | 0.02 | 0.60 | 0.38 |
| b | 0.02 | 0.38 | 0 60 |
| c | 0.39 | 0.01 | 0.60 |
| d | 0.60 | 0.01 | 0.39 |
| e | 0.60 | 0.39 | 0.01 |
| f | 0.39 | 0.60 | 0.01 |

ELAPO compositions are generally synthesized by hydrothermal crystallization from a reaction mixture containing reactive sources of the elements "M", aluminum and phosphorous, preferably an organic templating, i.e., structure directing, agent, preferably a compound of an element of Group VA of the Periodic Table, and/or optionally an alkali or other metal. The reaction mixture is generally placed in a sealed pressure vessel, preferably lined with an inert plastic material such as polytetrafluoroethylene and heated, preferably under autogenous pressure at a temperature between 50° C. and 250° C., and preferably between 100° C. and 200° C., until crystals of the ELAPO product are obtained, usually a period of from several hours to several weeks. Typical crystallization times are from about 2 hours to about 30 days with from about 2 hours to about 20 days being generally employed to obtain crystals of the ELAPO products. The product is recovered by any convenient method such as centrifugation or filtration.

In synthesizing the ELAPO compositions of the instant invention, it is in general preferred to employ a reaction mixture composition expressed in terms of the molar ratios as follows:

$$aR:(M_xAl_yP_z)O_2:bH_2O$$

wherein "R" is an organic templating agent; "a" is the amount of organic templating agent "R" and has a value of from zero to about 6 and is preferably an effective amount within the range of greater than zero (0) to about 6; "b" has a value of from zero (0) to about 500, preferably between about 2 and 300; "M" represents at least one element, as above described, capable of forming tetrahedral oxide framework units, $MO_2^n$, with $AlO_2^-$ and $PO_2^+$ tetrahedral units; "n" has a value of −3, −2, −1, 0 or +1; and "x", "y" and "z" represent the mole fractions of "M", aluminum and phosphorous, respectively; "y" and "z" each have a value of at least 0.01 and "x" has a value of at least 0.01 with each element "M" having a mole fraction of at least 0.01. In general, the mole fractions "x", "y" and "z" are preferably within the following values for "x", "y" and "z":

| Point | Mole Fraction | | |
|---|---|---|---|
| | x | y | z |
| F | 0.01 | 0.60 | 0.39 |
| G | 0.01 | 0.39 | 0.60 |
| H | 0.39 | 0.01 | 0.60 |
| I | 0.98 | 0.01 | 0.01 |
| J | 0.39 | 0.60 | 0.01 |

Further guidance concerning the preferred reaction mixtures for forming ELAPOs with various elements "M" will be given below.

In the foregoing expression of the reaction composition, the reactants are normalized with respect to a total of $(M+Al+P)=(x+y+z)=1.00$ mole, whereas in other cases the reaction mixtures are expressed in terms of molar oxide ratios and may be normalized to 1.00 mole of $P_2O_5$ and/or $Al_2O_3$. This latter form is readily converted to the former form by routine calculations by dividing the total number of moles of "M", aluminum and phosphorous into the moles of each of "M", aluminum and phosphorous. The moles of template and water are similarly normalized by dividing by the total moles of "M", aluminum and phosphorous.

In forming the reaction mixture from which the instant molecular sieves are formed the organic templating agent can be any of those heretofore proposed for use in the synthesis of conventional zeolite aluminosilicates. In general these compounds contain elements of Group VA of the Periodic Table of Elements, particularly nitrogen, phosphorous, arsenic and antimony, preferably nitrogen or phosphorous and most preferably nitrogen, which compounds also contain at least one alkyl or aryl group having from 1 to 8 carbon atoms. Particularly preferred compounds for use as templating agents are the amines, quaternary phosphonium compounds and quaternary ammonium compounds, the latter two being represented generally by the formula $R_4X^+$ wherein "X" is nitrogen or phosphorous and each R is an alkyl or aryl group containing from 1 to 8 carbon atoms. Polymeric quaternary ammonium salts such as $[(C_{14}H_{32}N_2)(OH_2)]_x$ wherein "x" has a value of at least 2 are also suitably employed. The mono-, di- and tri-amines are advantageously utilized, either alone or in combination with a quaternary ammonium compound or other templating compound. Mixtures of two or more templating agents can either produce mixtures of the desired ELAPOs or the more strongly directing templating species may control the course of the reaction with the other templating species serving primarily to establish the pH conditions of the reaction gel. Representative templating agents include tetramethylammonium, tetraethylammonium, tetrapropylammonium or tetrabutylammonium ions; tetrapentylammonium ion; di-n-propylamine; tripropylamine; triethylamine; triethanolamine; piperidine; cyclohexylamine; 2-methylpyridine; N,N-dimethylbenzylamine; N,N-dimethylethanolamine; choline; N,N'-dimethylpiperazine; 1,4-diazabicyclo (2,2,2,) octane; N-methyldiethanolamine; N-methylethanolamine; N-methylpiperidine; 3-methylpiperidine; n-methylcyclohexylamine; 3-methylpyridine; 4-methylpyridine; quinuclidine; N,N'-dimethyl-1,4-diazabicyclo (2,2,2) octane ion; di-n-butylamine, neopentylamine; di-n-pentylamine; isopropylamine; t-butylamine; ethylenediamine; pyrrolidine; and 2-imidazolidone. Not every templating agent will direct the formation of every species of ELAPO, i.e., a single templating agent can, with proper manipulation of the reaction conditions, direct the formation of several ELAPO compositions, and a given ELAPO composition can be produced using several different templating agents. The phosphorous source is preferably phosphoric acid, but organic phosphates such as triethyl phosphate may be satisfactory, and so also may crystalline or amorphous aluminophosphates such as the $AlPO_4$ composition of U.S. Pat. No. 4,310,440. Organophosphorous compounds, such as tetrabutylphosphonium bromide, do not apparently serve as reactive sources of phosphorous, but these compounds may function as templating agents. Conventional phosphorous salts such as sodium metaphosphate, may be used, at least in part, as the phosphorous source, but are not preferred.

The aluminum source is preferably either an aluminum alkoxide, such as aluminum isopropoxide, or pseudoboehmite. The crystalline or amorphous aluminophosphates which are a suitable source of phosphorous are, of course, also suitable sources of aluminum. Other sources of aluminum used in zeolite synthesis, such as gibbsite, sodium aluminate and aluminum trichloride, can be employed but are not preferred.

The element(s) "M" can be introduced into the reaction system in any form which permits the formation in situ of reactive form of the element, i.e., reactive to form the framework tetrahedral oxide unit of the element. The organic and inorganic salts, of "M" such as oxides, alkoxides, hydroxides, halides and carboxyates, may be employed including the chlorides, bromides, iodides, nitrates, sulfates, phosphates, acetates, formates, and alkoxides, including ethoxides, propoxides and the like. Specific preferred reagents for introducing various elements "M" are discussed hereinbelow.

While not essential to the synthesis of ELAPO compositions, stirring or other moderate agitation of the reaction mixture and/or seeding the reaction mixture with seed crystals of either the ELAPO species to be produced or a topologically similar species, such as aluminophosphate, alumino-silicate or molecular sieve compositions, facilitates the crystallization procedure.

After crystallization the ELAPO product may be isolated and advantageously washed with water and dried in air. The as synthesized ELAPO generally contains within its internal pore system at least one form of the templating agent employed in its formation. Most commonly the organic moiety is present, at least in part, as a charge balancing cation as is generally the case with as synthesized aluminosilicate zeolites prepared from organic-containing reaction systems. It is possible, however, that some or all of the organic moiety is an occluded molecular species in a particular ELAPO species. As a general rule the templating agent, and hence the occluded organic species, is too large to move freely through the pore system of the ELAPO product and must be removed by calcining the ELAPO at temperatures of 200° C. to 700° C. to thermally degrade the organic species. In a few instances the pores of the ELAPO product are sufficiently large to permit transport of the templating agent, particularly if the latter is a small molecule, and accordingly complete or partial removal thereof can be accomplished by conventional desorption procedures such as carried out in the case of zeolites. It will be understood that the term "as synthesized" as used herein does not include the condition of the ELAPO phase wherein the organic moiety occupying the intracrystalline pore system as a result of the hydrothermal crystallization process has been reduced by post-synthesis treatment such that the value of "m" in the composition formula:

$$mR:(M_xAl_yP_z)O_2$$

has a value of less than 0.02. The other symbols of the formula are as defined hereinabove. In those preparations in which an alkoxide is employed as the source of element "M", aluminum or phosphorous, the corresponding alcohol is necessarily present in the reaction mixture since it is a hydrolysis product of the alkoxide. It has not been determined whether this alcohol participates in the synthesis process as a templating agent. For the purposes of this application, however, this alcohol is arbitrarily omitted from the class of templating agents, even if it is present in the as-synthesized ELAPO material.

Since the present ELAPO compositions are formed from $MO_2^n$, $AlO_2^-$ and $PO_2^+$ tetrahedral oxide units which, respectively, have a net charge of "n", (where "n" may be $-3$, $-2$, $-1$, 0 or $+1$), the matter of cation exchangeability is considerably more complicated than in the case of zeolitic molecular sieves in which, ideally, there is stoichiometric relationship between $AlO_2^-$ tetrahedra and charge balancing cations. In the instant compositions, an $AlO_2^-$ tetrahedron can be balanced electrically either by association with a $PO_2^+$ tetrahedron or a simple cation such as an alkali metal cation, a proton (H+), a cation of "M" present in the reaction mixture, or an organic cation derived from the templating agent. Similarly, an MO$_2^n$ tetrahedron, where "n" is negative, can be balanced electrically by association with PO$_2$+ tetrahedra, a cation of "M" present in the reaction mixture, organic cations derived from the templating agent, a simple cation such as an alkali metal cation, or other divalent or polyvalent metal cation, a proton (H+), or anions of cations introduced from an extraneous source. It has also been postulated that non-adjacent AlO$_2^-$ and PO$_2^+$ tetrahedral pairs can be balanced by Na+ and OH- respectively (Flanigen and Grose, Molecular Sieve Zeolites-I, ACS, Washington, D.C. (1971).

AsAPO MOLECULAR SIEVES

The AsAPO molecular sieves of U.S. Ser. Nos. 600,166, filed Apr.13, 1984, and 830,889 filed Feb. 19, 1986 have a framework structure of AsO$_2^n$, AlO$_2^-$ and PO$_2^+$ tetrahedral units (where "n" is −1 or +1) and have an empirical chemical composition on an anhydrous basis expressed by the formula $$mR:(As_xAl_yP_z)O_2$$

wherein "R" represents at least one organic templating agent present in the intracrystalline pore system; "m" represents the molar amount of "R" present per mole of (As$_x$Al$_y$P$_z$)O$_2$ and has a value of zero to about 0. is preferably not greater than 0.15; and "x", "y" and "z" represent the mole fractions of the elements arsenic, aluminum and phosphorous, respectively, present as tetrahedral oxides. The mole fractions "x", "y" and "z" are generally defined as being within the limiting compositional values or points as follows:

| Point | Mole Fraction | | |
|---|---|---|---|
| | x | y | z |
| A | 0.01 | 0.60 | 0.39 |
| B | 0.01 | 0.39 | 0.60 |
| C | 0.39 | 0.01 | 0.60 |
| D | 0.60 | 0.01 | 0.39 |
| E | 0.60 | 0.39 | 0.01 |
| F | 0.39 | 0.60 | 0.01 |

There are two preferred subclasses of the AsAPO molecular sieves, depending upon whether the value of "n" is −1 or +1 (i.e. whether the arsenic is trivalent or pentavalent), it being understood that mixtures of such are permitted in a given AsAPO. When "n" is −1, the preferred values of x, y and z are within the limiting compositional values or points as follows:

| Point | Mole Fraction | | |
|---|---|---|---|
| | x | y | z |
| a | 0.01 | 0.59 | 0.40 |
| b | 0.01 | 0.39 | 0.60 |
| c | 0.39 | 0.01 | 0.60 |
| d | 0.59 | 0.01 | 0.40 |

When "n" is +1, the preferred values of x, y and z are within the limiting compositional values or points as follows:

| Point | Mole Fraction | | |
|---|---|---|---|
| | x | y | z |
| e | 0.01 | 0.60 | 0.39 |
| f | 0.01 | 0.40 | 0.59 |
| g | 0.59 | 0.40 | 0.01 |
| h | 0.39 | 0.60 | 0.01 |

In an especially preferred subclass of the AsAPO molecular sieves in which "n"=+1, the values of x, y and z are as follows:

| Point | Mole Fraction | | |
|---|---|---|---|
| | x | y | z |
| i | 0.03 | 0.52 | 0.45 |
| j | 0.03 | 0.45 | 0.52 |
| k | 0.08 | 0.40 | 0.52 |
| l | 0.33 | 0.40 | 0.27 |
| m | 0.33 | 0.41 | 0.26 |
| n | 0.22 | 0.52 | 0.26 |

AsAPO compositions are generally synthesized by hydrothermal crystallization from a reaction mixture containing reactive sources of arsenic, aluminum and phosphorous, preferably an organic templating, i.e., structure directing, agent, preferably a compound of an element of Group VA of the Periodic Table, and/or optionally an alkali or other metal. The reaction mixture is generally placed in a sealed pressure vessel, preferably lined with an inert plastic material such as polytetrafluoroethylene and heated, preferably under autogenous pressure at a temperature between about 50° C. and about 250° C., and preferably between about 100° C. and about 200° C. until crystals of the AsAPO product are obtained, usually a period of from several hours to several weeks. Typical effective times of from 2 hours to about 30 days, generally from about 2 hours to about 20 days, and preferably about 12 hours to about 7 days, have been observed. The product is recovered by any convenient method such as centrifugation or filtration.

In synthesizing the AsAPO compositions, it is preferred to employ a reaction mixture composition expressed in terms of the molar ratios as follows:

$$aR:(As_xAl_yP_z)O_2:bH_2O$$

wherein "R" is an organic templating agent; "a" is the amount of organic templating agent "R" and has a value of from zero to about 6 and is preferably an effective amount within the range of greater than zero (0) to about 6, and most preferably not more than about 0.5; "b" has a value of from zero (0) to about 500, preferably between about 2 and about 300, most preferably not greater than about 20; and "x", "y" and "z" represent the mole fractions of arsenic, aluminum and phosphorous, respectively, and each has a value of at least 0.01.

In one embodiment the reaction mixture is selected such that the mole fractions "x", "y" and "z" are generally defined as being within the limiting compositional values or points as follows:

| Point | Mole Fraction | | |
|---|---|---|---|
| | x | y | z |
| G | 0.01 | 0.60 | 0.39 |
| H | 0.01 | 0.39 | 0.60 |

-continued

| Point | Mole Fraction | | |
|---|---|---|---|
| | x | y | z |
| I | 0.39 | 0.01 | 0.60 |
| J | 0.98 | 0.01 | 0.01 |
| K | 0.39 | 0.60 | 0.01 |

Especially preferred reaction mixtures are those wherein the mole fractions "x", "y" and "z" are within the limiting compositional values or points as follows:

| Point | Mole Fraction | | |
|---|---|---|---|
| | x | y | z |
| a | 0.20 | 0.55 | 0.25 |
| b | 0.20 | 0.50 | 0.30 |
| c | 0.30 | 0.40 | 0.30 |
| d | 0.40 | 0.40 | 0.20 |
| e | 0.40 | 0.50 | 0.10 |
| f | 0.35 | 0.55 | 0.10 |

In the foregoing expression of the reaction composition, the reactants are normalized with respect to the total of "x", "y" and "z" such that $(x+y+z)=1.00$ mole. Molecular sieve containing arsenic, aluminum and phosphorous as framework tetrahedral oxide units are prepared as follows:

Preparative Reagents

AsAPO compositions may be prepared by using numerous reagents. Reagents which may be employed to prepare AsAPOs include:
(a) aluminum isopropoxide;
(b) pseudoboehmite or other aluminum oxide;
(c) $H_3PO_4$: 85 weight percent aqueous phosphoric acid;
(d) $As_2O_5$, arsenic (V) oxide;
(e) TEAOH: 40 weight percent aqueous solution of tetraethylammonium hydroxide;
(f) TBAOH: 40 weight percent aqueous solution of tetrabutylammonium hydroxide;
(g) $Pr_2NH$: di-n-propylamine, $(C_3H_7)_2NH$;
(h) $Pr_3N$: tri-n-propylamine, $(C_3H_7)_3N$;
(i) Quin: Quinuclidine, $(C_7H_{13}N)$;
(j) MQuin: Methyl Quinuclidine hydroxide, $(C_7H_{13}NCH_3OH)$;
(k) C-hex: cyclohexylamine;
(l) TMAOH: tetramethylammonium hydroxide
(m) TPAOH: tetrapropylammonium hydroxide; and
(n) DEEA: 2-diethylaminoethanol.

Preparative Procedures

AsAPOs may be prepared by forming a starting reaction mixture by dissolving the arsenic (V) oxide and the $H_3PO_4$ in at least part of the water. To this solution the aluminum oxide or isopropoxide is added. This mixture is then blended until a homogeneous mixture is observed. To this mixture the templating agent and the resulting mixture blended until a homogeneous mixture is observed. The mixture is then placed in a lined (polytetrafluoroethylene) stainless steel pressure vessel and digested at a temperature (150° C. or 200° C.) for a time or placed in lined screw top bottles for digestion at 100° C. Digestions are typically carried out under autogenous pressure.

BAPO MOLECULAR SIEVES

The BAPO molecular sieves of U.S. Ser. Nos. 599,812, filed Apr. 13, 1984, 804,248, filed Dec. 4, 1985, and 029,540, filed Mar. 24, 1987, have a framework structure of $BO_2^-$, $AlO_2^-$ and $PO_2^+$ tetrahedral units and have an empirical chemical composition on an anhydrous basis expressed by the formula:

$$mR:(B_xAl_yP_z)O_2$$

wherein "R" represents at least one organic templating agent present in the intracrystalline pore system; "m" represents the molar amount of "R" present per mole of $(B_xAl_yP_z)O_2$ and has a value of zero to about 0.3, "x", "y" and "z" represent the mole fractions of the elements boron, aluminum and phosphorus, respectively, present as tetrahedral oxides. The more fractions "x", "y" and "z" are generally defined as being within the limiting compositional values or points as follows:

| Point | Mole Fraction | | |
|---|---|---|---|
| | x | y | z |
| A | 0.01 | 0.60 | 0.39 |
| B | 0.01 | 0.39 | 0.60 |
| C | 0.39 | 0.01 | 0.60 |
| D | 0.60 | 0.01 | 0.39 |
| E | 0.60 | 0.39 | 0.01 |
| F | 0.39 | 0.60 | 0.01 |

In a preferred subclass of the BAPO molecular sieves the values of x, y, and z are within the limiting compositional values or points as follows:

| Point | Mole Fraction | | |
|---|---|---|---|
| | x | y | z |
| a | 0.01 | 0.59 | 0.40 |
| b | 0.01 | 0.39 | 0.60 |
| c | 0.39 | 0.01 | 0.60 |
| d | 0.59 | 0.01 | 0.40 |

An especially preferred subclass of the BAPO molecular sieves are those in which the mole fraction, "x", of boron is not greater than about 0.3.

BAPO compositions are generally synthesized by hydrothermal crystallization from a reaction mixture containing reactive sources of boron, aluminum and phosphorus, preferably an organic templating, i.e., structure directing, agent, preferably a compound of an element of Group VA of the Periodic Table, and/or optionally an alkali or other metal. The reaction mixture is generally placed in a sealed pressure vessel, preferably lined with an inert plastic material such as polytetrafluoroethylene and heated, preferably under autogenous pressure at a temperature between about 50° C. and about 250° C., and preferably between about 100° C. and about 200° C. until crystals of the BAPO product are obtained, usually a period of from several hours to several weeks. Typical effective times of from 2 hours to about 30 days, generally from about 4 hours to about 14 days, and preferably about 1 to about 7 days, have been observed. The product is recovered by any convenient method such as centrifugation or filtration.

In synthesizing the BAPO compositions, it is preferred to employ a reaction mixture composition expressed in terms of the molar ratios as follows:

$$aR:(B_xAl_yP_z)O_2:bH_2O$$

where "R" is an organic templating agent; "a" is the amount of organic templating agent "R" and is an effective amount preferably within the range of greater than zero (0) to about 6, and most preferably not more than about 1.0; "b" has a value of from zero (0) to about 500, preferably between about 2 and about 300, desirably not greater than about 20, and most desirably not greater than about 10; and "x", "y" and "z" represent the mole fractions of boron, aluminum and phosphorus, respectively, and each has a value of at least 0.01.

In one embodiment the reaction mixture is selected such that the mole fractions "x", "y" and "z" are generally defined as being within the limiting compositional values or points as follows:

| Point | Mole Fraction | | |
|---|---|---|---|
| | x | y | z |
| G | 0.01 | 0.60 | 0.39 |
| H | 0.01 | 0.39 | 0.60 |
| I | 0.39 | 0.01 | 0.60 |
| J | 0.98 | 0.01 | 0.01 |
| K | 0.39 | 0.60 | 0.01 |

Especially preferred reaction mixtures are those containing from 0.5 to 2.0 moles of $B_2O_3$ and from 0.75 to 1.25 moles of $Al_2O_3$ for each mole of $P_2O_5$.

In the foregoing expression of the reaction composition, the reactants are normalized with respect to the total of "x", "y" and "z" such that $(x+y+z) = 1.00$ mole.

The exact nature of the BAPO molecular sieves is not entirely understood at present, although all are believed to contain $BO_2$, $AlO_2$ and $PO_2$ tetrahedra in the three dimensional microporous framework structure. The low level of boron present in some of the instant molecular sieves makes it difficult to ascertain the exact nature of the interactions among boron, aluminum and phosphorus. As a result, although it is believed that $BO_2$ tetrahedra are present in the three-dimensional microporous framework structure, it is appropriate to characterize certain BAPO compositions in terms of the molar ratios of oxides.

Molecular sieves containing boron, aluminum and phosphorus as framework tetrahedral oxide units are prepared as follows:

Preparative Reagents

BAPO compositions may be prepared by using numerous reagents. Reagents which may be employed to prepare BAPOs include:
(a) aluminum isopropoxide;
(b) pseudoboehmite or other aluminum oxide;
(c) $H_3PO_4$: 85 weight percent aqueous phosphoric acid;
(d) boric acid or trimethylborate;
(e) TEAOH: 40 weight percent aqueous solution of tetraethylammonium hydroxide;
(f) TBAOH: 40 weight percent aqueous solution of tetrabutylammonium hydroxide;
(g) $Pr_2NH$: di-n-propylamine, $(C_3H_7)_2NH$;
(h) $Pr_3N$: tri-n-propylamine, $(C_3H_7)_3N$;
(i) Quin: Quinulidine, $(C_7H_{13}N)$,
(j) MQuin: Methyl Quinuclide hydroxide, $(C_7H_{13}NCH_3OH)$;
(k) C-hex: cyclohexylamine;
(l) TMAOH: tetramethylammonium hydroxide;
(m) TPAOH: tetrapropylammonium hydroxide; and
(n) DEEA: 2-diethylaminoethanol.

Preparative Procedures

In the preferred method of synthesizing the BAPO compositions, one first combines sources of boron, aluminum and phosphorus to form an amorphous material containing all three elements, and thereafter heats the amorphous material to produce a crystalline BAPO molecular sieve. It is not necessary that the total quantities of the reactive sources of boron, aluminum and phosphorus to be used in the final reaction mixture be present in the amorphous material, since additional quantities of the elements can be added during the later heat treatment; in particular, it has been found convenient to add additional quantities of phosphorus to the amorphous material before the heat treatment. The preliminary formation of the amorphous material assists in the incorporation of the boron into the final molecular sieve.

For example, BAPOs may be prepared by forming a solution of boric acid in a methanolic solution of the templating agent, then adding a hydrated aluminosphosphate and water and stirring to form a homogeneous reaction slurry. This slurry is then placed in a lined (polytetrafluoroethylene) stainless steel pressure vessel and digested at a temperature (150° C. or 200° C.) for a time or placed in lined screw top bottles for digestion at 100° C. Digestions are typically carried out under autogenous pressure.

BeAPO MOLECULAR SIEVES

The BeAPO molecular sieves of U.S. Ser. Nos. 599,776, filed Apr. 13, 1984, and 835,293 filed Mar. 3, 1986 have a framework structure of $BeO_2^{-2}$, $AlO_2^-$ and $PO_2^+$ tetrahedral units and have an empirical chemical composition on an anhydrous basis expressed by the formula:

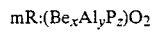

$$mR:(Be_xAl_yP_z)O_2$$

wherein "R" represents at least one organic templating agent present in the intracrystalline pore system; "m" represents the molar amount of "R" present per mole of $(Be_xAl_yP_z)O_2$ and has a value of zero to about 0.3, but is preferably not greater than 0.15; and "x", "y" and "z" represent the mole fractions of the elements beryllium, aluminum and phosphorus, respectively, present as tetrahedral oxides. The mole fractions "x", "y" and "z" are generally defined as being within the limiting compositional values or points as follows:

| Point | Mole Fraction | | |
|---|---|---|---|
| | x | y | z |
| A | 0.01 | 0.60 | 0.39 |
| B | 0.01 | 0.39 | 0.60 |
| C | 0.39 | 0.01 | 0.60 |
| D | 0.60 | 0.01 | 0.39 |
| E | 0.60 | 0.39 | 0.01 |
| F | 0.39 | 0.60 | 0.01 |

In a preferred subclass of the BeAPO molecular sieves the values of x, y and z are within the limiting compositional values or points as follows:

| Point | Mole Fraction | | |
|---|---|---|---|
| | x | y | z |
| a | 0.01 | 0.60 | 0.39 |
| b | 0.01 | 0.39 | 0.60 |

-continued

| Point | Mole Fraction | | |
|---|---|---|---|
| | x | y | z |
| c | 0.35 | 0.05 | 0.60 |
| d | 0.35 | 0.60 | 0.05 |

In an especially preferred subclass of the BeAPO molecular sieves the values of x, y and z are as follows:

| Point | Mole Fraction | | |
|---|---|---|---|
| | x | y | z |
| e | 0.02 | 0.46 | 0.52 |
| f | 0.10 | 0.38 | 0.52 |
| g | 0.10 | 0.46 | 0.44 |

BeAPO compositions are generally synthesized by hydrothermal crystallization from a reaction mixture containing reactive sources of beryllium, aluminum and phosphorus, preferably an organic templating, i.e., structure directing, agent, preferably a compound of an element of Group VA of the Periodic Table, and/or optionally an alkali or other metal. The reaction mixture is generally placed in a sealed pressure vessel, preferably lined with an inert plastic material such as polytetrafluoroethylene and heated, preferably under autogenous pressure at a temperature between about 50° C. and about 250° C., and preferably between about 100° C. and about 200° C. until crystals of the BeAPO product are obtained, usually a period of from several hours to several weeks. Typical effective times of from 2 hours to about 30 days, generally from about 4 hours to about 14 days, and preferably about 1 to about 7 days, have been observed. The product is recovered by any convenient method such as centrifugation or filtration.

In synthesizing the BeAPO compositions, it is preferred to employ a reaction mixture composition expressed in terms of the molar ratios as follows:

wherein "R" is an organic templating agent; "a" is the amount of organic templating agent "R" and has a value of from zero to about 6 and is preferably an effective amount within the range of greater than zero (0) to about 6, and most preferably not more than about 1.5; "b" has a value of from zero (0) to about 500, preferably between about 2 and about 300, most preferably not greater than about 50; and "x", "y" and "z" represent the mole fractions of beryllium, aluminum and phosphorus, respectively, and each has a value of at least 0.01.

In one embodiment the reaction mixture is selected such that the mole fractions "x", "y" and "z" are generally defined as being within the limiting compositional values or points as follows:

| Point | Mole Fraction | | |
|---|---|---|---|
| | x | y | z |
| G | 0.01 | 0.60 | 0.39 |
| H | 0.01 | 0.39 | 0.60 |
| I | 0.39 | 0.01 | 0.60 |
| J | 0.98 | 0.01 | 0.01 |
| K | 0.39 | 0.60 | 0.01 |

Especially preferred reaction mixtures are those wherein the mole fractions "x", "y" and "z" are within the limiting compositional values or points as follows:

| Point | Mole Fraction | | |
|---|---|---|---|
| | x | y | z |
| g | 0.04 | 0.46 | 0.50 |
| h | 0.16 | 0.34 | 0.50 |
| i | 0.17 | 0.34 | 0.49 |
| j | 0.17 | 0.43 | 0.40 |
| k | 0.14 | 0.46 | 0.40 |

In the foregoing expression of the reaction composition, the reactants are normalized with respect to the total of "x", "y" and "z" such that (x+y+z)=1.00 mole. Molecular sieves containing beryllium, aluminum and phosphorus as framework tetrahdedral oxide units are prepared as follows:

Preparative Reagents

BeAPO compositions may be prepared by using numerous reagents. Reagents which may be employed to prepare BeAPOs include:
(a) aluminum isopropoxide;
(b) pseudoboehmite or other aluminum oxide;
(c) $H_3PO_4$: 85 weight percent aqueous phosphoric acid;
(d) beryllium sulfate;
(e) TEAOH: 40 weight percent aqueous solution of tetraethylammonium hydroxide;
(f) TBAOH: 40 weight percent aqueous solution of tetrabutylammonium hydroxide;
(g) $Pr_2NH$: di-n-propylamine, $(C_3H_7)_2NH$;
(h) $Pr_3N$: tri-n-propylamine, $(C_3H_7)_3N$;
(i) Quin: Quinuclidine, $(C_7H_{13}N)$;
(j) MQuin: Methyl Quinuclide hydroxide, $(C_7H_{13}NCH_3OH)$;
(k) C-hex: cyclohexylamine;
(l) TMAOH: tetramethylammonium hydroxide;
(m) TPAOH: tetrapropylammonium hydroxide; and
(n) DEEA: 2-diethylaminoethanol.

Preparative Procedures

BeAPOs may be prepared by forming a starting reaction mixture by dissolving the beryllium sulfate and the $H_3PO_4$ in at least part of the water. To this solution the aluminum oxide or isopropoxide is added. This mixture is then blended until a homogeneous mixture is observed. To this mixture the templating agent and the resulting mixture blended until a homogeneous mixture is observed. The mixture is then placed in a lined (polytetrafluoroethylene) stainless steel pressure vessel and digested at a temperature (150° C. or 200° C. for a time or placed in lined screw top bottles for digestion at 100° C. Digestions are typically carried out under autogenous pressure.

CAPO MOLECULAR SIEVES

The CAPO molecular sieves of U.S. Ser. Nos. 599,813, filed Apr. 13, 1984, and 830,756 filed Feb. 19, 1986 have a framework structure of $CrO_2^n$, $AlO_2^-$ and $PO_2^+$ tetrahedral units (where "n" is $-1$, 0 or $+1$) and have an empirical chemical composition on an anhydrous basis expressed by the formula

wherein "R" represents at least one organic templating agent present in the intracrystalline pore system; "m" represents the molar amount of "R" present per mole of $(Cr_xAl_yP_z)O_2$ and has a value of zero to about 0.3, but is preferably not greater than 0.15; and "x", "y" and "z" represent the mole fractions of the elements chromium, aluminum and phosphorus, respectively, present as tetrahedral oxides. When "n" is −1 or +1, the mole fractions "x", "y" and "z" are generally defined as being within the limiting compositional values or points as follows:

|       | Mole Fraction |      |      |
|-------|---------------|------|------|
| Point | x             | y    | z    |
| A     | 0.01          | 0.60 | 0.39 |
| B     | 0.01          | 0.39 | 0.60 |
| C     | 0.39          | 0.01 | 0.60 |
| D     | 0.60          | 0.01 | 0.39 |
| E     | 0.60          | 0.39 | 0.01 |
| F     | 0.39          | 0.60 | 0.01 |

When "n" is 0, the mole fractions "x", "y" and "z" are generally defined as being within the limiting compositional values or points as follows:

|       | Mole Fraction |      |      |
|-------|---------------|------|------|
| Point | x             | y    | z    |
| G     | 0.01          | 0.60 | 0.39 |
| H     | 0.01          | 0.47 | 0.52 |
| I     | 0.94          | 0.01 | 0.05 |
| J     | 0.98          | 0.01 | 0.01 |
| K     | 0.39          | 0.60 | 0.01 |

There are three preferred subclasses of the CAPO molecular sieves, depending upon whether the value of "n" is −1, 0 or +1 (i.e. whether the chromium has an oxidation number of 3, 4 or 5), it being understood that mixtures of such are permitted is a given CAPO. When "n" is −1, the preferred values of x, y and z are within the limiting compositional values or points as follows:

|       | Mole Fraction |      |      |
|-------|---------------|------|------|
| Point | x             | y    | z    |
| a     | 0.01          | 0.59 | 0.40 |
| b     | 0.01          | 0.39 | 0.60 |
| c     | 0.39          | 0.01 | 0.60 |
| d     | 0.59          | 0.01 | 0.40 |

In a especially preferred subclass of these CAPO molecular sieves in which "n" = −1, the values of x, y and z are as follows:

|       | Mole Fraction |      |      |
|-------|---------------|------|------|
| Point | x             | y    | z    |
| n     | 0.01          | 0.52 | 0.47 |
| o     | 0.01          | 0.42 | 0.57 |
| p     | 0.03          | 0.40 | 0.57 |
| q     | 0.07          | 0.40 | 0.53 |
| r     | 0.07          | 0.47 | 0.46 |
| s     | 0.02          | 0.52 | 0.46 |

When "n" is 0, the preferred values of x, y and z are within the limiting compositional values or points as follows:

|       | Mole Fraction |       |       |
|-------|---------------|-------|-------|
| Point | x             | y     | z     |
| e     | 0.01          | 0.60  | 0.39  |
| f     | 0.01          | 0.47  | 0.52  |
| g     | 0.50          | 0.225 | 0.275 |
| h     | 0.50          | 0.40  | 0.10  |
| i     | 0.30          | 0.60  | 0.10  |

When "n" is +1, the preferred values of x, y and z are within the limiting compositional values or points as follows:

|       | Mole Fraction |      |      |
|-------|---------------|------|------|
| Point | x             | y    | z    |
| j     | 0.01          | 0.60 | 0.39 |
| k     | 0.01          | 0.40 | 0.59 |
| l     | 0.59          | 0.40 | 0.01 |
| m     | 0.39          | 0.60 | 0.10 |

Since the exact nature of the CAPO molecular sieves is not clearly understood at present, although all are believed to contain $CrO_2$ tetrahedra in the three-dimensional microporous crystal framework structure, it is advantageous to characterize the CAPO molecular sieves by means of their chemical composition. This is due to the low level of chromium present in certain of the CAPO molecular sieves prepared to date which makes it difficult to ascertain the exact nature of the interaction between chromium, aluminum and phosphorous. As a result, although it is believed that $CrO_2$ tetrahedra are substituted isomorphously for $AlO_2$ or $PO_2$ tetrahedra, it is appropriate to characterize certain CAPO compositions by reference to their chemical composition in terms of the mole ratios of oxides.

CAPO compositions are generally synthesized by hydrothermal crystallization from a reaction mixture containing reactive sources of chromium, aluminum and phosphorous, preferably an organic templating, i.e., structure directing, agent, preferably a compound of an element of Group VA of the Periodic Table, and/or optionally an alkali or other metal. The reaction mixture is generally placed in a sealed pressure vessel, preferably lined with an inert plastic material such as polytetrafluoroethylene and heated, preferably under autogenous pressure at a temperature between about 50° C. and about 250° C., and preferably between about 100° C. and about 200° C. until crystals of the CAPO product are obtained, usually a period of from several hours to several weeks. Typical effective times of from 2 hours to about 30 days, generally from about 2 hours to about 20 days, and preferably about 1 to about 10 days, have been observed. The product is recovered by any convenient method such as centrifugation or filtration.

In synthesizing the CAPO compositions, it is preferred to employ a reaction mixture composition expressed in terms of the molar ratios as follows:

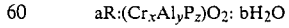

wherein "R" is an organic templating agent; "a" is the amount of organic templating agent "R" and has a value of from zero to about 6 and is preferably an effective amount within the range of greater than zero (0) to about 6, and most preferably not more than about 0.6; "b" has a value of from zero (0) to about 500, preferably between about 2 and about 300, most preferably not greater than about 20; and "x", "y" and "z" represent the mole fractions of chromium, aluminum and phosphorous, respectively, and each has a value of at least 0.01.

In one embodiment the reaction mixture is selected such that the mole fractions "x", "y" and "z" are generally defined as being within the limiting compositional values or points as follows:

| Point | Mole Fraction | | |
|-------|------|------|------|
|       | x    | y    | z    |
| L     | 0.01 | 0.60 | 0.39 |
| M     | 0.01 | 0.39 | 0.60 |
| N     | 0.39 | 0.01 | 0.60 |
| O     | 0.98 | 0.01 | 0.01 |
| P     | 0.39 | 0.60 | 0.01 |

Especially preferred reaction mixtures are those containing from about 0.1 to about 4 moles of chromium, and from about 0.75 to about 1.25 moles of aluminum, per mole of phosphorous.

In the foregoing expression of the reaction composition, the reactants are normalized with respect to the total of "x", "y" and "z" such that $(x+y+z)=1.00$ mole. Molecular sieves containing chromium, aluminum and phosphorous as framework tetrahedral oxide units are prepared as follows:

Preparative Reagents

CAPO compositions may be prepared by using numerous reagents. Reagents which may be employed to prepare CAPOs include:
(a) aluminum isopropoxide, or aluminum chlorhydrol;
(b) pseudoboehmite or other aluminum oxide;
(c) $H_3PO_4$: 85 weight percent aqueous phosphoric acid;
(d) chromium (III) orthophosphate, chromium (III) acetate and chromium acetate hydroxide, $(Cr_3(OH)_2(CH_3COO)_7)$;
(e) TEAOH: 40 weight percent aqueous solution of tetraethylammonium hydroxide;
(f) TBAOH: 40 weight percent aqueous solution of tetrabutylammonium hydroxide;
(g) Pr$_2$NH: di-n-propylamine, $(C_3H_7)_2NH$;
(h) Pr$_3$N: tri-n-propylamine, $(C_3H_7)_3N$;
(i) Quin: Quinuclidine, $(C_7H_{13}N)$;
(j) MQuin: Methyl Quinuclidine hydroxide, $(C_7H_{13}NCH_3OH)$;
(k) C-hex: cyclohexylamine;
(l) TMAOH: tetramethylammonium hydroxide:
(m) TPAOH: tetrapropylammonium hydroxide; and
(n) DEEA: 2-diethylaminoethanol.

Preparative Procedures

CAPOs may be prepared by forming a starting reaction mixture by adding aluminum chlorhydrol or aluminum oxide to a solution of chromium acetate hydroxide in water, then adding successively phosphoric acid and the templating agent. Between each addition, and after formation of the final mixture, the mixture is blended until a homogeneous mixture is observed.

Alternatively, the phosphoric acid may be mixed with at least part of the water, and aluminum oxide or isopropoxide mixed in. A solution of chromium acetate hydroxide is then added, followed by the templating agent, and the resultant mixture mixed until homogeneous.

In a third procedure, amorphous chromium phosphate is ground dry with aluminum oxide and the resultant dry mixture added to an aqueous solution of phosphoric acid in an ice bath. The templating agent is then added, and the final mixture mixed until homogenous.

Whichever technique is employed to produce the reaction mixture, this mixture is then placed in a lined (polytetrafluoroethylene) stainless steel pressure vessel and digested at a temperature (150° C. or 200° C.) for a time or placed in lined screw top bottles for digestion at 100° C. Digestions are typically carried out under autogenous pressure.

GaAPO MOLECULAR SIEVES

The GaAPO molecular sieves of U.S. Ser. Nos. 599,771, filed Apr. 13, 1984, and 830,890 filed Feb. 19, 1986 have a framework structure of $GaO_2^-$, $AlO_2$ and $PO_2^{30}$ tetrahedral units and have an empirical chemical composition on an anhydrous basis expressed by the formula:

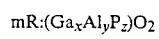
$$mR:(Ga_xAl_yP_z)O_2$$

wherein "R" represents at least one organic templating agent present in the intracrystalline pore system; "m" represents the molar amount of "R" present per mole of $(Ga_xAl_yP_z)O_2$ and has a value of zero to about 0.3, is preferably not greater than 0.15; and "x", "y" and "z" represent the mole fractions of the elements gallium, aluminum and phosphorous, respectively, present as tetrahedral oxides. The mole fractions "x", "y" and "z" are generally defined as being within the limiting compositional values or points as follows:

| Point | Mole Fraction | | |
|-------|------|------|------|
|       | x    | y    | z    |
| A     | 0.01 | 0.60 | 0.39 |
| B     | 0.01 | 0.34 | 0.65 |
| C     | 0.34 | 0.01 | 0.65 |
| D     | 0.60 | 0.01 | 0.39 |
| E     | 0.60 | 0.39 | 0.01 |
| F     | 0.39 | 0.60 | 0.01 |

In general, the value of "z" in the GaAPO molecular sieves is not greater than about 0.60.

In a preferred subclass of the GaAPO molecular sieves the values of x, y and z are within the limiting compositional values or points as follows:

| Point | Mole Fraction | | |
|-------|------|------|------|
|       | x    | y    | z    |
| a     | 0.01 | 0.59 | 0.40 |
| b     | 0.01 | 0.34 | 0.65 |
| c     | 0.34 | 0.01 | 0.65 |
| d     | 0.59 | 0.01 | 0.40 |

In an especially preferred subclass of the GaAPO molecular sieves the values of x, y and z are as follows:

| Point | Mole Fraction | | |
|-------|------|------|------|
|       | x    | y    | z    |
| e     | 0.03 | 0.52 | 0.45 |
| f     | 0.03 | 0.33 | 0.64 |
| g     | 0.16 | 0.20 | 0.64 |
| h     | 0.25 | 0.20 | 0.55 |
| i     | 0.25 | 0.33 | 0.42 |

| | Mole Fraction | | |
|---|---|---|---|
| Point | x | y | z |
| j | 0.06 | 0.52 | 0.42 |

GaAPO compositions are generally synthesized by hydrothermal crystallization from a reaction mixture containing reactive sources of gallium, aluminum and phosphorous, preferably an organic templating, i.e., structure directing, agent, preferably a compound of an element of Group VA of the Periodic Table, and/or optionally an alkali or other metal. The reaction mixture is generally placed in a sealed pressure vessel, preferably lined with an inert plastic material such as polytetrafluoroethylene and heated, preferably under autogenous pressure at a temperature between about 50° C. and about 250° C., and preferably between about 100° C. and about 200° C., until crystals of the GaAPO product are obtained, usually a period of from several hours to several weeks. Typical effective times of from 2 hours to about 30 days, generally from about 4 hours to about 20 days, and preferably about 1 to about 7 days, have been observed. The product is recovered by any convenient method such as centrifugation or filtration.

In synthesizing the GaAPO compositions, it is preferred to employ a reaction mixture composition expressed in terms of the molar ratios as follows:

$$aR:(Ga_xAl_yP_z)O_2:bH_2O$$

wherein "R" is an organic templating agent; "a" is the amount of organic templating agent "R" and has a value of from zero to about 6 and is preferably an effective amount within the range of greater than zero (0) to about 6, and most preferably not more than about 1.0; "b" has a value of from zero (0) to about 500, preferably between about 2 and about 300, most preferably between about 2 and 20; and "x", "y" and "z" represent the mole fractions of gallium, aluminum and phosphorous, respectively, and each has a value of at least 0.01.

In one embodiment the reaction mixture is selected such that the mole fractions "x", "y" and "z" are generally defined as being within the limiting compositional values or points as follows:

| | Mole Fraction | | |
|---|---|---|---|
| Point | x | y | z |
| G | 0.01 | 0.60 | 0.39 |
| H | 0.01 | 0.39 | 0.60 |
| I | 0.39 | 0.01 | 0.60 |
| J | 0.98 | 0.01 | 0.01 |
| K | 0.39 | 0.60 | 0.01 |

Especially preferred reaction mixtures are those containing from 0.2 to 0.5 mole of $Ga_2O_3$ and from 0.3 to 1 mole of $Al_2O_3$ for each mole of $P_2O_5$.

In the foregoing expression of the reaction composition, the reactants are normalized with respect to the total of "x", "y" and "z" such that $(x+y+z)=1.00$ mole. Molecular sieves containing gallium, aluminum and phosphorous as framework tetrahedral oxide units are prepared as follows:

Preparative Reagents

GaAPO compositions may be prepared by using numerous reagents. Reagents which may be employed to prepare GaAPOs include:
(a) aluminum isopropoxide;
(b) pseudoboehmite or other aluminum oxide;
(c) $H_3PO_4$: 85 weight percent aqueous phosphoric acid;
(d) gallium sulfate or gallium (III) hydroxide;
(e) TEAOH: 40 weight percent aqueous solution of tetraethylammonium hydroxide;
(f) TBAOH: 40 weight percent aqueous solution of tetrabutylammonium hydroxide;
(g) $Pr_2NH$: di-n-propylamine, $(C_3H_7)_2NH$;
(h) $Pr_3N$: tri-n-propylamine, $(C_3H_7)_3N$;
(i) Quin: Quinuclidine, $(C_7H_{13}N)$;
(j) MQuin: Methyl Quinuclidine hydroxide, $(C_7H_{13}NCH_3OH)$;
(k) C-hex: cyclohexylamine;
(l) TMAOH: tetramethylammonium hydroxide;
(m) TPAOH: tetrapropylammonium hydroxide; and
(n) DEEA: 2-diethylaminoethanol.

Preparative Procedures

GaAPOs may be prepared by forming a starting reaction mixture by mixing the phosphoric acid with at least part of the water. To this solution the aluminum oxide or isopropoxide is added. This mixture is then blended until a homogenous mixture is observed. To this mixture the gallium sulfate or gallium hydroxide and the templating agent are successively added and the resulting mixture blended until a homogeneous mixture is observed.

Alternatively, the aluminum oxide may be mixed with a solution of the gallium sulfate or hydroxide, and then the phosphoric acid and the templating agent successively added. The resulting mixture is then blended until a homogeneous mixture is observed.

In a third process, the templating agent may be dissolved in water, the gallium hydroxide or sulfate added with stirring, a solution of the phosphoric acid added, and finally the aluminum oxide mixed in. The resulting mixture is then blended until a homogeneous mixture is observed.

Whichever technique is employed to form the reaction mixture, the mixture is then placed in a lined (polytetrafluoroethylene) stainless steel pressure vessel and digested at a temperature (150° C. or 200° C.) for a time or placed in lined screw top bottles for digestion at 100° C. Digestions are typically carried out under autogenous pressures.

GeAPO MOLECULAR SIEVES

The GeAPO molecular sieves of U.S. Ser. Nos. 599,807, filed Apr. 13, 1984, and 841,753 filed Mar. 20, 1986 have a framework structure of $GeO_2$, $AlO_2^{31}$ and $PO_2^+$ tetrahedral units and have an empirical chemical composition on an anhydrous basis expressed by the formula:

$$mR:(Ge_xAl_yP_z)O_2$$

wherein "R" represents at least one organic templating agent present in the intracrystalline pore system; "m" represents the molar amount of "R" present per mole of $(Ge_xAl_yP_z)O_2$ and has a value of zero to about 0.3, is preferably not greater than 0.2; and "x", "y" and "z" represent the mole fractions of the elements germanium, aluminum and phosphorous, respectively, present as tetrahedral oxides. The mole fractions "x", "y" and "z" are generally defined as being within the limiting compositional values or points as follows:

| Point | Mole Fraction | | |
|---|---|---|---|
| | x | y | z |
| A | 0.01 | 0.60 | 0.39 |
| B | 0.01 | 0.47 | 0.52 |
| C | 0.94 | 0.01 | 0.05 |
| D | 0.98 | 0.01 | 0.01 |
| E | 0.39 | 0.60 | 0.01 |

In a preferred subclass of the GeAPO molecular sieves the values of x, y and z are within the limiting compositional values or points as follows:

| Point | Mole Fraction | | |
|---|---|---|---|
| | x | y | z |
| a | 0.01 | 0.60 | 0.39 |
| b | 0.01 | 0.47 | 0.52 |
| c | 0.50 | 0.225 | 0.275 |
| d | 0.50 | 0.40 | 0.10 |
| e | 0.30 | 0.60 | 0.10 |

An especially preferred subclass of the GeAPO molecular sieves are those in which the value of "x" is not greater than about 0.13.

GeAPO compositions are generally synthesized by hydrothermal crystallization from a reaction mixture containing reactive sources of germanium, aluminum and phosphorous, preferably an organic templating, i.e., structure directing, agent, preferably a compound of an element of Group VA of the Periodic Table, and/or optionally an alkali or other metal. The reaction mixture is generally placed in a sealed pressure vessel, preferably lined with an inert plastic material such as polytetrafluoroethylene and heated, preferably under autogenous pressure at a temperature between about 50° C. and about 250° C., and preferably between about 100° C. and about 200° C., until crystals of the GeAPO product are obtained, usually a period of from several hours to several weeks. Typical effective times of from 2 hours to about 30 days, generally from about 2 hours to about 20 days, and preferably about 1 to about 10 days, have been observed. The product is recovered by any convenient method such as centrifugation or filtration.

In synthesizing the GeAPO compositions, it is preferred to employ a reaction mixture composition expressed in terms of the molar ratios as follows:

$$aR:(Ge_xAl_yP_z)O_2:bH_2O$$

wherein "R" is an organic templating agent; "a" is the amount of organic templating agent "R" and has a value of from zero to about 6 and is preferably an effective amount within the range of greater than zero (0) to about 6, and most preferably not more than about 0.6; "b" has a value of from zero (0) to about 500, preferably between about 2 and about 300, most preferably between about 10 and about 60; and "x", "y" and "z" represent the mole fractions of germanium, aluminum and phosphorous, respectively, and each has a value of at least 0.01.

In one embodiment the reaction mixture is selected such that the mole fractions "x", "y" and "z" are generally defined as being within the limiting compositional values or points as follows:

| Point | Mole Fraction | | |
|---|---|---|---|
| | x | y | z |
| F | 0.01 | 0.60 | 0.39 |
| G | 0.01 | 0.39 | 0.60 |
| H | 0.39 | 0.01 | 0.60 |
| I | 0.98 | 0.01 | 0.01 |
| J | 0.39 | 0.60 | 0.01 |

Especially preferred reaction mixtures are those containing from 0.2 to 0.4 mole of GeO$_2$ and from 0.75 to 1.25 mole of Al$_2$O$_3$ for each mole of P$_2$O$_5$.

In the foregoing expression of the reaction composition, the reactants are normalized with respect to the total of "x", "y" and "z" such that $(x+y+z) = 1.00$ mole. Molecular sieves containing germanium, aluminum, and phosphorous as framework tetrahedral oxide units are prepared as follows:

Preparative Reagents

GeAPO compositions may be prepared by using numerous reagents. Reagents which may be employed to prepare GeAPOs include:
(a) aluminum isopropoxide;
(b) pseudoboehmite or other aluminum oxide;
(c) H$_3$PO$_4$: 85 weight percent aqueous phosphoric acid;
(d) germanium tetrachloride, germanium ethoxide and germanium dioxide;
(e) TEAOH: 40 weight percent aqueous solution of tetraethylammonium hydroxide;
(f) TBAOH: 40 weight percent aqueous solution of tetrabutylammonium hydroxide;
(g) Pr$_2$NH: di-n-propylamine, (C$_3$H$_7$)$_2$NH;
(h) Pr$_3$N: tri-n-propylamine, (C$_3$H$_7$)$_3$H;
(i) Quin: Quinuclidine, (C$_7$H$_{13}$N);
(j) MQuin: Methyl Quinuclidine hydroxide, (C$_7$H$_{13}$NCH$_3$OH);
(k) C-hex: cyclohexylamine;
(l) TMAOH: tetramethylammonium hydroxide;
(m) TPAOH: tetrapropylammonium hydroxide; and
(n) DEEA: 2-diethylaminoethanol.

Preparative Procedures

In some cases, it may be advantageous, when synthesizing the GeAPO compositions, to first combine sources of germanium and aluminum, to form a mixed germanium/aluminum compound (this compound typically a mixed oxide) and thereafter to combine this mixed compound with a source of phosphorous to form the final GeAPO composition. Such mixed oxides may be prepared for example by hydrolyzing aqueous solutions containing germanium tetrachloride and aluminum chlorhydrol, or aluminum tri-sec-butoxide.

GeAPOs may be prepared by forming a starting reaction mixture by mixing the phosphoric acid with at least part of the water. To this solution is added the mixed germanium/aluminum oxide prepared as described above. This mixture is then blended until a homogeneous mixture is observed. To this mixture the templating agent is added and the resulting mixture blended until a homogeneous mixture is observed.

Alternatively, to a solution of aluminum isopropoxide may be added germanium ethoxide. The resultant solution may optionally be dried to produce a mixed oxide. To the mixed solution or dried oxide are added successively the phosphoric acid and the templating agent. The resulting mixture is then blended until a homogeneous mixture is observed.

In a third process, a solution is formed by dissolving the phosphoric acid in water, adding aluminum oxide or isopropoxide and mixing thoroughly. To the resultant mixture is added a solution containing the templating agent and germanium dioxide. The resulting mixture is then blended until a homogeneous mixture is observed.

Whichever technique is employed to form the reaction mixture, the mixture is then placed in a lined (polytetrafluoroethylene) stainless steel pressure vessel and digested at a temperature (150° C. or 200° C.) for a time or placed in lined screw top bottles for digestion at 100° C. Digestions are typically carried out under autogenous pressure.

LiAPO MOLECULAR SIEVES

The LiAPO molecular sieves of U.S. Ser. Nos. 599,811, filed Apr. 13, 1984, and 834,921 filed Feb. 28, 1986 have a framework structure of $LiO_2^{-3}$, $AlO_2^{-}$ and $PO_2^{+}$ tetrahedral units and have an empirical chemical composition on an anhydrous basis expressed by the formula:

$$mR:(Li_xAl_yP_z)O_2$$

wherein "R" represents at least one organic templating agent present in the intracrystalline pore system; "m" represents the molar amount of "R" present per mole of $(Li_xAl_{dy}P_z)O_2$ and has a value of zero to about 0.3, is preferably not greater than 0.15; and "x", "y" and "z" represent the mole fractions of the elements lithium, aluminum and phosphorous, respectively, present as tetrahedral oxides. The mole fractions "x", "y" and "z" are generally defined as being within the limiting compositional values or points as follows:

| Point | Mole Fraction | | |
|---|---|---|---|
| | x | y | z |
| A | 0.01 | 0.60 | 0.39 |
| B | 0.01 | 0.39 | 0.60 |
| C | 0.39 | 0.01 | 0.60 |
| D | 0.60 | 0.01 | 0.39 |
| E | 0.60 | 0.39 | 0.01 |
| F | 0.39 | 0.60 | 0.01 |

In a preferred subclass of the LiAPO molecular sieves the values of x, y and z are within the limiting compositional values of points as follows:

| Point | Mole Fraction | | |
|---|---|---|---|
| | x | y | z |
| a | 0.01 | 0.60 | 0.39 |
| b | 0.01 | 0.39 | 0.60 |
| c | 0.35 | 0.05 | 0.60 |
| d | 0.35 | 0.60 | 0.05 |

In a especially preferred subclass of the LiAPO molecular sieves the values of x, y and z are within the following limits:

| Point | Mole Fraction | | |
|---|---|---|---|
| | x | y | z |
| e | 0.01 | 0.52 | 0.47 |
| f | 0.01 | 0.47 | 0.52 |
| g | 0.03 | 0.45 | 0.52 |
| h | 0.10 | 0.45 | 0.45 |
| i | 0.10 | 0.49 | 0.41 |
| j | 0.07 | 0.52 | 0.41 |

LiAPO compositions are generally synthesized by hydrothermal crystallization from a reaction mixture containing reactive sources of lithium, aluminum and phosphorous, preferably an organic templating, i.e., structure directing, agent, preferably a compound of an element of Group VA of the Periodic Table, and/or optionally an alkali or other metal. The reaction mixture is generally placed in a sealed pressure vessel, preferably lined with an inert plastic material such as polytetrafluoroethylene and heated, preferably under autogenous pressure at a temperature between about 50° C. and about 250° C., and preferably between about 100° C. and about 200° C. until crystals of the LiAPO product are obtained, usually a period of from several hours to several weeks. Typical effective times of from 2 hours to about 30 days, generally from about 12 hours to about 5 days, have been observed. The product is recovered by any convenient method such as centrifugation or filtration.

In synthesizing the LiAPO compositions, it is preferred to employ a reaction mixture composition expressed in terms of the molar ratios as follows:

$$aR:(Li_xAl_yP_z)O_2:bH_2O$$

wherein "R" is an organic templating agent; "a" is the amount of organic templating agent "R" and has a value of from zero to about 6 and is preferably an effective amount within the range of greater than zero (0) to about 6, and most preferably not more than about 2; "b" has a value of from zero (0) to about 500, preferably between 2 and 300, most preferably not greater than about 40; and "x", "y" and "z" represent the mole fractions of lithium, aluminum and phosphorous, respectively, and each has a value of at least 0.01.

In one embodiment the reaction mixture is selected such that the mole fractions "x", "y" and "z" are generally defined as being within the limiting compositional values or points as follows:

| Point | Mole Fraction | | |
|---|---|---|---|
| | x | y | z |
| G | 0.01 | 0.60 | 0.39 |
| H | 0.01 | 0.39 | 0.60 |
| I | 0.39 | 0.01 | 0.60 |
| J | 0.98 | 0.01 | 0.01 |
| K | 0.39 | 0.60 | 0.01 |

In an especially preferred subclass of he reaction mixtures, the values of "x", "y" and "z" are within the limiting compositional values or points as follows:

| Point | Mole Fraction | | |
|---|---|---|---|
| | x | y | z |
| l | 0.03 | 0.50 | 0.47 |
| m | 0.03 | 0.45 | 0.52 |
| n | 0.08 | 0.40 | 0.52 |
| o | 0.10 | 0.40 | 0.50 |
| q | 0.04 | 0.50 | 0.46 |

In the foregoing expression of the reaction composition, the reactants are normalized with respect to the total of "x", "y" and "z" such that $(x+y+z)=1.00$ mole.

Since the exact nature of the LiAPO molecular sieves is not clearly understood at present, although all are believed to contain $LiO_2$ tetrahedra in the three dimensional microporous crystal framework structure, it is advantageous to characterize the LiAPO molecular sieves by means of their chemical composition. This is due to the low level of lithium present in certain of the LiAPO molecular sieves prepared to date which makes it difficult to ascertain the exact nature of the interaction between lithium, aluminum and phosphorous. As a result, although it is believed that $LiO_2$ tetrahedra are substituted isomorphously for $AlO_2$ or $PO_2$ tetrahedra, it is appropriate to characterize certain LiAPO compositions by reference to their chemical composition in terms of the mole ratios of oxides.

Molecular sieves containing lithium, aluminum and phosphorous as framework tetrahedral oxide units are prepared as followed:

Preparative Reagents

LiAPO compositions may be prepared by using numerous reagents. Reagents which may be employed to prepare LiAPOs include:

(a) aluminum isopropoxide;
(b) pseudoboehmite or other aluminum oxide;
(c) $H_3PO_4$: 85 weight percent aqueous phosphoric acid;
(d) lithium sulfate or lithium orthophosphate;
(e) TEAOH: 40 weight percent aqueous solution of tetraethylammonium hydroxide;
(f) TBAOH: 40 weight percent aqueous solution of tetrabutylammonium hydroxide;
(g) $Pr_2NH$: di-n-propylamine, $(C_3H_7)_2NH$;
(h) $Pr_3N$: tri-n-propylamine, $(C_3H_7)_3N$;
(i) Quin: Quinuclidine, $(C_7H_{13}N)$;
(j) MQuin: Methyl Quinuclidine hydroxide, $(C_7H_{13}NCH_3OH)$;
(k) C-hex: cyclohexylamine;
(l) TMAOH: tetramethylammonium hydroxide;
(m) TPAOH: tetrapropylammonium hydroxide; and
(n) DEEA: 2-diethylaminoethanol.

Preparative Procedures

LiAPOs may be prepared by forming a starting reaction mixture by suspending aluminum oxide in at least part of the water. To this mixture the templating agent is added. The resultant mixture is then blended until a homogeneous mixture is observed. To this mixture the lithium phosphate or sulfate is added and the resulting mixture blended until a homogeneous mixture is observed. Alternatively, an initial mixture may be formed by mixing aluminum oxide and lithium phosphate or sulfate. To the resultant mixture are added successively phosphoric acid and an aqueous solution of the templating agent, and the resulting mixture blended until a homogeneous mixture is observed.

In a third procedure, the phosphoric acid is mixed with at least part of the water, and the aluminum oxide is mixed in. To the resultant mixture are added lithium sulfate and the templating agent, and the resulting mixture blended until a homogeneous mixture is observed.

Whichever procedure is adopted to form the reaction mixture, the mixture is then placed in a lined (polytetrafluoroethylene) stainless steel pressure vessel and digested at a temperature (150° C. or 200° C.) for a time or placed in lined screw top bottles for digestion at 100° C. Digestions are typically carried out under autogenous pressure.

FeTiAPO MOLECULAR SIEVES

The FeTiAPO molecular sieves of U.S. Ser. Nos. 599,824, filed Apr. 13, 1984, and 902,129 filed Sept. 2, 1986 have three dimensional microporous framework structures of $FeO_2^n$, $TiO_2$, $AlO_2^-$ and $PO_2^+$ tetrahedral oxide units, where "n" is $-2$ or $-1$, and have an empirical chemical composition on an anhydrous basis expressed by the formula:

$mR:(M_xAl_yP_z)O_2$ wherein "R" represents at least one organic templating agent present in the intracrystalline pore system; "M" represents iron and titanium; "m" represents the molar amount of "R" present per mole of $(M_xAl_yP_z)O_2$ and has a value of zero (0) to about 0.3; and "x", "y" and "z" represent the mole fractions of "M", aluminum and phosphorus, respectively present as tetrahedral oxides. The mole fractions "x", "y" and "z" are generally defined as being within the limiting compositional values or points as follows:

| Point | Mole Fraction | | |
|---|---|---|---|
| | x | y | z |
| A | 0.02 | 0.60 | 0.38 |
| B | 0.02 | 0.38 | 0.60 |
| C | 0.39 | 0.01 | 0.60 |
| D | 0.98 | 0.01 | 0.01 |
| E | 0.39 | 0.60 | 0.01 |

In a preferred subclass of the FeTiAPO molecular sieves the values of x, y and z are within the limiting compositional values or points as follows:

| Point | Mole Fraction | | |
|---|---|---|---|
| | x | y | z |
| a | 0.02 | 0.60 | 0.38 |
| b | 0.02 | 0.38 | 0.60 |
| c | 0.39 | 0.01 | 0.60 |
| d | 0.60 | 0.01 | 0.39 |
| e | 0.60 | 0.39 | 0.01 |
| f | 0.39 | 0.60 | 0.01 |

FeTiAPO compositions are generally synthesized by hydrothermal crystallization from a reaction mixture containing reactive sources of iron, titanium, aluminum and phosphorous, preferably an organic templating, i.e., structure directing, agent, preferably a compound of an element of Group VA of the Periodic Table, and/or optionally an alkali or other metal. The reaction mixture is generally placed in a sealed pressure vessel, preferably lined with an inert plastic material such as polytetrafluoroethylene and heated, preferably under autogenous pressure at a temperature between about 50° C. and about 250° C., and preferably between about 100° C. and about 200° C. until crystals of the FeTiAPO product are obtained, usually a period of from several hours to several weeks. Typical effective times of from 2 hours to about 30 days, generally from about 12 hours to about 5 days, have been observed. The product is recovered by any convenient method such as centrifugation or filtration.

In synthesizing the FeTiAPO compositions, it is preferred to employ a reaction mixture composition expressed in terms of the molar ratios as follows:

$$aR:(M_xAl_yP_z)O_2:bH_2O$$

wherein "R" is an organic templating agent; "a" is the amount of organic templating agent "R" and has a value of from zero to about 6 and is preferably an effective amount within the range of greater than zero (0) to about 6; "b" has a value of from zero (0) to about 500, preferably between about 2 and about 300; and "x", "y" and "z" represent the mole fractions of "M" (iron and titanium), aluminum and phosphorous, respectively, and each has a value of at least 0.01.

In one embodiment the reaction mixture is selected such that the mole fractions "x", "y" and "z" are generally defined as being within the limiting compositional values or points as follows:

| Point | Mole Fraction | | |
|---|---|---|---|
| | x | y | z |
| F | 0.02 | 0.60 | 0.38 |
| G | 0.02 | 0.38 | 0.60 |
| H | 0.39 | 0.01 | 0.60 |
| I | 0.98 | 0.01 | 0.01 |
| J | 0.39 | 0.60 | 0.01 |

In the foregoing expression of the reaction composition, the reactants are normalized with respect to the total of "x", "y" and "z" such that $(x+y+z)=1.00$ mole.

Molecular sieves containing iron, titanium, aluminum and phosphorous as framework tetrahedral oxide units are prepared as follows:

Preparative Reagents

FeTiAPO compositions may be prepared by numerous reagents. The preferred sources of iron and titanium for preparing FeTiAPOs are the same as those for preparing the FeAPOs and TiAPOs already described above. Other reagents which may be employed to prepare FeTiAPOs include:

(a) aluminum isopropoxide;
(b) pseudoboehmite or other aluminum oxide;
(c) $H_3PO_4$: 85 weight percent aqueous phosphoric acid;
(d) TEAOH: 40 weight percent aqueous solution of tetraethylammonium hydroxide;
(e) TBAOH: 40 weight percent aqueous solution of tetrabutylammonium hydroxide;
(f) $Pr_2NH$: di-n-propylamine, $(C_3H_7)_2NH$;
(g) $Pr_3N$: tri-n-propylamine, $(C_3H_7)_3N$;
(h) Quin: Quinuclidine, $(C_7H_{13}N)$;
(i) MQuin: Methyl Quinuclidine hydroxide, $(C_7H_{13}NCH_3OH)$;
(j) C-hex: cyclohexylamine;
(k) TMAOH: tetramethylammonium hydroxide;
(l) TPAOH: tetrapropylammonium hydroxide; and
(m) DEEA: 2-diethylaminoethanol.

Preparative Procedures

FeTiAPOs may be prepared by forming a homogeneous reaction mixture containing reactive sources of iron, titanium, aluminum and phosphorous. The reaction mixture is then placed in a lined (polytetrafluoroethylene) stainless steel pressure vessel and digested at a temperature (150° C. or 200° C.) for a time or placed in lined screw top bottles for digestion at 100° C. Digestions are typically carried out under autogenous pressure.

XAPO MOLECULAR SIEVES

The XAPO molecular sieves of U.S. Ser. Nos. 599,810, filed Apr. 13, 1984, and 902,020 filed Sept. 2, 1986 have a three dimensional microporous framework structure of $MO_2^n$, $AlO_2^-$ and $PO_2^+$ tetrahedral oxide units; where "n" is 0, −1 or −2, and have an empirical chemical composition on an anhydrous basis expressed by the formula:

$$mR:(M_xAl_yP_z)O_2$$

wherein "R" represents at least one organic templating agent present in the intracrystalline pore system; "M" represents at least one element from each of the classes of: (1) iron and titanium; and (2) cobalt, magnesium, manganese and zinc; "n" is 0, −1 or −2; "m" represents a molar amount of "R" present per mole of $(M_xAl_yP_z)O_2$ and has a value of zero (0) to about 0.3; and "x", "y" and "z" represent the mole fractions of "M", aluminum and phosphorus, respectively, present as tetrahedral oxides. The mole fractions "x", "y" and "z" are generally defined as being within the limiting compositional values or points as follows:

| Point | Mole Fraction | | |
|---|---|---|---|
| | x | y | z |
| A | 0.02 | 0.60 | 0.38 |
| B | 0.02 | 0.38 | 0.60 |
| C | 0.39 | 0.01 | 0.60 |
| D | 0.98 | 0.01 | 0.01 |
| E | 0.39 | 0.60 | 0.01 |

In a preferred subclass of the XAPO molecular sieves the values of x, y and z are within the limiting compositional values or points as follows:

| Point | Mole Fraction | | |
|---|---|---|---|
| | x | y | z |
| a | 0.02 | 0.60 | 0.38 |
| b | 0.02 | 0.38 | 0.60 |
| c | 0.39 | 0.01 | 0.60 |
| d | 0.60 | 0.01 | 0.39 |
| e | 0.60 | 0.39 | 0.01 |
| f | 0.39 | 0.60 | 0.01 |

XAPO compositions are generally synthesized by hydrothermal crystallization from a reaction mixture containing reactive sources of "M", aluminum and phosphorous, preferably an organic templating, i.e., structure directing, agent, preferably a compound of an element of Group VA of the Periodic Table, and/or optionally an alkali or other metal. The reaction mixture is generally placed in a sealed pressure vessel, preferably lined with an inert plastic material such as polytetrafluoroethylene and heated, preferably under autogenous pressure at a temperature between about 50° C. and about 250° C., and preferably between about 100° C. and about 200° C. until crystals of the XAPO product are obtained, usually a period of from several hours to several weeks. Typical effective times of from 2 hours to about 30 days, generally from about 2 hours to about 20 days, have been observed. The product is recovered by any convenient method such as centrifugation or filtration.

In synthesizing the XAPO compositions, it is preferred to employ a reaction mixture composition expressed in terms of the molar ratios as follows:

$$aR:(M_xAl_yP_z)O_2:bH_2O$$

wherein "R" is an organic templating agent; "a" is the amount of organic templating agent "R" and has a value of from zero to about 6 and is preferably an effective amount within the range of greater than zero (0) to about 6; "M" represents at least one element from each of the classes of: (1) iron and titanium; and (2) cobalt, magnesium, manganese and zinc; "b" has a value of from zero (0) to about 500, preferably between about 2 and about 300; and "x", "y" and "z" represent the mole fractions of "M" (iron and/or titanium, and at least one of cobalt, magnesium, manganese and zinc), aluminum and phosphorous, respectively, and each has a value of at least 0.01, with the proviso that "x" has a value of at least 0.02.

In one embodiment the reaction mixture is selected such that the mole fractions "x", "y" and "z" are generally defined as being within the limiting compositional values or points as follows:

| Point | Mole Fraction | | |
|---|---|---|---|
| | x | y | z |
| F | 0.02 | 0.60 | 0.38 |
| G | 0.02 | 0.38 | 0.60 |
| H | 0.39 | 0.01 | 0.60 |
| I | 0.98 | 0.01 | 0.01 |
| J | 0.39 | 0.60 | 0.01 |

In the foregoing expression of the reaction composition, the reactants are normalized with respect to the total of "x", "y" and "z" such that $(x+y+z)=1.00$ mole.

XAPO molecular sieves are prepared as follows:

Preparative Reagents

XAPO compositions may be prepared by using numerous reagents. The preferred sources of elements "M" for preparing XAPOs are the same as those for preparing other APOs containing the same elements, as described above and below. Other reagents which may be employed to prepare XAPOs include:
(a) aluminum isopropoxide;
(b) pseudoboehmite or other aluminum oxide;
(c) $H_3PO_4$: 85 weight percent aqueous phosphoric acid;
(d) TEAOH: 40 weight percent aqueous solution of tetraethylammonium hydroxide;
(e) TBAOH: 40 weight percent aqueous solution of tetrabutylammonium hydroxide;
(f) $Pr_2NH$: di-n-propylamine, $(C_3H_7)_2NH$;
(g) $Pr_3N$: tri-n-propylamine, $(C_3H_7)_3N$;
(h) Quin: Quinuclidine, $(C_7H_{13}N)$;
(i) MQuin: Methyl Quinuclidine hydroxide, $(C_7H_{13}NCH_3OH)$;
(j) C-hex: cyclohexylamine;
(k) TMAOH: tetramethylammonium hydroxide
(l) TPAOH: tetrapropylammonium hydroxide; and
(m) DEEA: 2-diethylaminoethanol.

Preparative Procedures

XAPOs may be prepared by forming a homogenous reaction mixture containing reactive sources of element "M", aluminum and phosphorous. The reaction mixture is then placed in a lined (polytetrafluoroethylene) stainless steel pressure vessel and digested at a temperature (150° C. or 200° C.) for a time or placed in lined screw top bottles for digestion at 100° C. Digestions are typically carried out under autogenous pressure.

MIXED ELEMENT APO MOLECULAR SIEVES

The mixed element APO molecular sieves of U.S. Ser. Nos. 599,978, filed Apr. 13, 1984, and 846,088 filed Mar. 31, 1986 have a framework structure of $MO_2^n$, $AlO_2^-$ and $PO_2^+$ tetrahedral units, wherein $MO_2$ represents at least two different elements present as tetrahedral units "$MO_2^n$" with charge "n", where "n" may be $-3$, $-2$, $-1$, or 0 or $+1$. One of the elements "M" is selected from the group consisting of arsenic, beryllium, boron, chromium, gallium, germanium, lithium and vanadium, while a second one of the elements "M" is selected from the group consisting of cobalt, iron, magnesium, manganese, titanium and zinc. Preferably, "M" is a mixture of lithium and magnesium. The mixed element molecular sieves have an empirical chemical composition on an anhydrous basis expressed by the formula:

$$mR:(M_xAl_yP_z)O_2$$

wherein "R" represents at least one organic templating agent present in the intracrystalline pore system; "m" represents the molar amount of "R" present per mole of $(M_xAl_yP_z)O_2$ and has a value of zero to about 0.3, but is preferably not greater than 0.15; and "x", "y" and "z" represent the mole fractions of the elements "M" (i.e. "x" is the total of the mole fractions of the two or more elements "M"), aluminum and phosphorous, respectively, present as tetrahedral oxides. The mole fractions "x", "y" and "z" are generally defined as being within the limiting compositional values or points as follows:

| Point | Mole Fraction | | |
|---|---|---|---|
| | x | y | z |
| A | 0.02 | 0.60 | 0.38 |
| B | 0.02 | 0.38 | 0.60 |
| C | 0.39 | 0.01 | 0.60 |
| D | 0.98 | 0.01 | 0.01 |
| E | 0.39 | 0.60 | 0.01 |

In a preferred subclass of the mixed element APO molecular sieves the values of x, y and z are within the limiting compositional values or points as follows:

| Point | Mole Fraction | | |
|---|---|---|---|
| | x | y | z |
| a | 0.02 | 0.60 | 0.38 |
| b | 0.02 | 0.38 | 0.60 |
| c | 0.39 | 0.01 | 0.60 |
| d | 0.60 | 0.01 | 0.39 |
| e | 0.60 | 0.39 | 0.01 |
| f | 0.39 | 0.60 | 0.01 |

An especially preferred subclass of the mixed element APO molecular sieves are those in which the value of x is not greater than about 0.10.

A second group (FCAPO's) of mixed element APO molecular sieves described in U.S. Ser. No. 600,171, filed Apr. 13, 1984 (now U.S. Pat. No. 4,686,093 issued Aug. 11, 1987), have a framework structure of $MO_2^n$, $AlO_2^-$ and $PO_2^+$ tetrahedral units, wherein $MO_2^n$ represents at least two different elements which are present as tetrahedral units "$MO_2^n$" with charge "n", where "n" may be $-3$, $-2$, $-1$, 0 or $+1$ and which are selected from the group consisting of arsenic, beryllium, boron, chromium, gallium, germanium, lithium and vanadium. These mixed element molecular sieves have an empirical chemical composition on an anhydrous basis expressed by the formula:

$$mR:(M_xAl_yP_z)O_2$$

wherein "R" represents at least one organic templating agent present in the intracrystalline pore system; "m" represents the molar amount of "R" present per mole of $(M_xAl_yP_z)O_2$ and has a value of zero to about 0.3; and "x", "y" and "z" represent the mole fractions of the elements "M" (i.e. "x" is the total of the mole fractions of the two or more elements "M"), aluminum and phosphorous, respectively, present as tetrahedral oxides. The mole fractions "x", "y" and "z" are generally defined as being within the limiting compositional values or points as follows:

| Point | Mole Fraction | | |
|---|---|---|---|
| | x | y | z |
| A | 0.02 | 0.60 | 0.38 |
| B | 0.02 | 0.38 | 0.60 |
| C | 0.39 | 0.01 | 0.60 |
| D | 0.98 | 0.01 | 0.01 |
| E | 0.39 | 0.60 | 0.01 |

In a preferred subclass of these mixed element APO molecular sieves the values of x, y and z are within the limiting compositional values or points as follows:

| Point | Mole Fraction | | |
|---|---|---|---|
| | x | y | z |
| a | 0.02 | 0.60 | 0.38 |
| b | 0.02 | 0.38 | 0.60 |
| c | 0.39 | 0.01 | 0.60 |
| d | 0.60 | 0.01 | 0.39 |
| e | 0.60 | 0.39 | 0.01 |
| f | 0.39 | 0.60 | 0.01 |

The mixed-element APO compositions are generally synthesized by hydrothermal crystallization from a reaction mixture containing reactive sources of the elements "M", aluminum and phosphorous, preferably an organic templating, i.e., structure directing, agent, preferably a compound of an element of Group VA of the Periodic Table, and/or optionally an alkali or other metal. The reaction mixture is generally placed in a sealed pressure vessel, preferably lined with an inert plastic material such as polytetrafluoroethylene and heated, preferably under autogenous pressure at a temperature between about 50° C. and about 250° C., and preferably between about 100° C. and about 200° C. until crystals of the APO product are obtained, usually a period of from several hours to several weeks. Typical effective times of from 2 hours to about 30 days, generally from about 2 hours to about 20 days, and preferably about 12 hours to about 5 days, have been observed. The product is recovered by any convenient method such as centrifugation or filtration.

In synthesizing the mixed element APO compositions, it is preferred to employ a reaction mixture composition expressed in terms of the molar ratios as follows:

$$aR:(M_xAl_yP_z)O_2:bH_2O$$

wherein "R" is an organic templating agent, "a" is the amount of organic templating agent "R" and has a value of from zero to about 6 and is preferably an effective amount within the range of greater than zero (0) to about 6, and most preferably not more than 0.5; "b" has a value of from zero (0) to about 500, preferably between about 2 and about 300, most preferably not greater than about 20, and most desirably not more than about 10; and "x", "y" and "z" represent the mole fractions of "M", aluminum and phosphorous, respectively, "y" and "z" each having a value of at least 0.01 and "x" having a value of at least 0.02, with each element "M" having a mole fraction of at least 0.01.

In one embodiment the reaction mixture is selected such that the mole fractions "x", "y" and "z" are generally defined as being within the limiting compositional values or points as follows:

| Point | Mole Fraction | | |
|---|---|---|---|
| | x | y | z |
| F | 0.02 | 0.60 | 0.38 |
| G | 0.02 | 0.38 | 0.60 |
| H | 0.39 | 0.01 | 0.60 |
| I | 0.98 | 0.01 | 0.01 |
| J | 0.39 | 0.60 | 0.01 |

Preferred reaction mixtures are those containing not more than about 0.2 moles of the metals "M" per mole of phosphorous.

In the foregoing expression of the reaction composition, the reactants are normalized with respect to the total of "x" "y" and "z" such that $(x+y+z)=1.00$ mole.

Since the exact nature of the mixed element APO molecular sieves is not clearly understood at present, although all are believed to contain $MO_2$ tetrahedra in the three dimensional microporous crystal framework structure, it is advantageous to characterize the mixed-element APO molecular sieves by means of their chemical composition. This is due to the low level of the elements "M" present in certain of the mixed element APO molecular sieves prepared to date which makes it difficult to ascertain the exact nature of the interaction between the metals "M", aluminum and phosphorous. As a result, although it is believed that $MO_2$ tetrahedra are substituted isomorphously for $AlO_2$ or $PO_2$ tetrahedra, it is appropriate to characterize certain mixed element APO compositions by reference to their chemical composition in terms of the mole ratios of oxides.

Molecular sieves containing the metals "M", aluminum and phosphorous as framework tetrahedral oxide units are prepared as follows:

Preparative Reagents

Mixed-element APO compositions may be prepared by using numerous reagents. Reagents which may be employed to prepare mixed element APOs include:
(a) aluminum isopropoxide;
(b) pseudoboehmite or other aluminum oxide;
(c) $H_3PO_4$: 85 weight percent aqueous phosphoric acid;
(d) lithium phosphate or magnesium hydroxide or appropriate salts of the other elements "M", as described above;

(e) TEAOH: 40 weight percent aqueous solution of tetraethylammonium hydroxide;
(f) TBAOH: 40 weight percent aqueous solution of tetrabutylammonium hydroxide;
(g) Pr$_2$NH: di-n propylamine, (C$_3$H$_7$)$_2$NH;
(h) Pr$_3$N: tri-n-propylamine, (C$_3$H$_7$)$_3$N;
(i) Quin: Quinuclidine, (C$_7$H$_{13}$N);
(j) MQuin: Methyl Quinuclidine hydroxide, (C$_7$H$_{13}$NCH$_3$OH);
(k) C hex: cyclohexylamine;
(l) TMAOH: tetramethylammonium hydroxide;
(m) TPAOH: tetrapropylammonium hydroxide; and
(n) DEEA: 2-diethylaminoethanol.

Preparative Procedures

Mixed element APOs may be prepared by forming a starting reaction mixture by mixing aluminum oxide, magnesium hydroxide, lithium phosphate (or the corresponding salts of the other elements "M"). To this mixture the phosphoric acid is added. The resultant mixture is then blended until a homogeneous mixture is observed. To this mixture the templating agent is added and the resulting mixture blended until a homogeneous mixture is observed.

The reaction mixture is then placed in a lined (polytetrafluoroethylene) stainless steel pressure vessel and digested at a temperature (150° C. or 200° C.) for a time or placed in lined screw top bottles for digestion at 100° C. Digestions are typically carried out under autogenous pressure.

SILICOALUMINOPHOSPHATE MOLECULAR SIEVES

The silicoaluminophosphate molecular sieves of U.S. Pat. No. 4,440,871 and the aforementioned application Ser. No. 575,745, are disclosed as microporous crystalline silicoaluminophosphates, the pores of which are uniform and have nominal diameters of greater than about 3 Angstroms and whose essential empirical chemical composition in the as synthesized and anhydrous form is:

mR:(Si$_x$Al$_y$P$_z$)O$_2$ wherein "R" represents at least one organic templating agent present in the intracrystalline pore system; "m" represents the moles of "R" present per mole of (Si$_x$Al$_y$P$_z$)O$_2$ and has a value of from 0.02 to 0.3 , "y" and "z" represent the mole fractions of silicon, aluminum and phosphorous, respectively, present as tetrahedral oxides, said mole fractions being such that they are within the pentagonal compositional area defined by points A, B, C, D and E of the ternary diagram of FIG. 5 of the aforementioned U.S. Pat. No. 4,440,871, and preferably within the pentagonal compositional area defined by points a, b, c, d and e of FIG. 6 of the patent. The SAPO molecular sieves of U.S. Pat. No. 4,440,871 and the aforementioned application Ser. No. 575,745 are also described as silicoaluminophosphates having a three dimensional microporous framework structure of PO$_2$+, AlO$_2$− and SiO$_2$ tetrahedral units, and whose essential empirical chemical composition on an anhydrous basis is:

mR:(Si$_x$Al$_y$P$_z$)O$_2$ wherein "R" represents at least one organic templating agent present in the intracrystalline pore system; "m" represents the mole of "R" present per mole of (Si$_x$Al$_y$P$_z$)O$_2$ and has a value of from zero to 0.3; "x", "y" and "z" represent, respectively, the mole fractions of silicon, aluminum and phosphorous present in the oxide moiety, said mole fractions being within the compositional area bounded by points A, B, C, D and E on the ternary diagram which is FIG. 5 of the aforementioned patent, said silicoaluminophosphate having a characteristic X-ray powder diffraction pattern which contains at least the d-spacings set forth below in any one of Tables I, III, V, VII, IX, XIII, XVII, XXI, XXIII or XXV of U.S. Pat. No. 4,440,871. Further, the as synthesized crystalline silicoaluminophosphates of U.S. Pat. No. 4,440,871 may be calcined at a temperature sufficiently high to remove at least some of any organic templating agent present in the intracrystalline pore system as a result of such synthesis. The silicoaluminophosphates of U.S. Pat. No. 4,440,871 are generally referred to therein as "SAPO", as a class, or as "SAPO-n" wherein "n" is an integer denoting a particular SAPO as its preparation is reported in U.S. Pat. No. 4,440,871. The preparation of the SAPOs is disclosed in U.S. Pat. No. 4,440,871, incorporated herein by reference.

Medium pore (MP)-SAPOs include SAPO-11, SAPO-31, SAPO-40 and SAPO 41.

The species SAPO-11 as referred to herein is a silicoaluminophosphate material having a three dimensional microporous crystal framework structure of PO$_2$+, AlO$_2$− and SiO$_2$ tetrahedral units, and whose essential empirical chemical composition on an anhydrous basis is:

mR:(Si$_x$Al$_y$P$_z$)O$_2$ wherein "R" represents at least one organic templating agent present in the intracrystalline pore system; "m" represents the moles of "R" present per mole of (Si$_x$Al$_y$P$_z$)O$_2$ and has a value of from zero to 0.3; , "y" and "z" represent, respectively, the mole fractions of silicon, aluminum and phosphorus present in the oxide moiety, said mole fractions being within the compositional area bounded by points A, B, C, D and E on the ternary diagram which is FIG. 5 of the patent, and preferably within the area bounded by points a, b, c, d and e on the ternary diagram which is FIG. 6 of the patent, said silicoaluminophosphate having a characteristic X-ray powder diffraction pattern which contains at least the d spacings set forth below:

| SAPO-11 | | |
|---|---|---|
| 2θ | d(Å) | Relative Intensity |
| 9.4–9.65 | 9.41–9.17 | m |
| 20.3–20.6 | 4.37–4.31 | m |
| 21.0–21.3 | 4.23–4.17 | vs |
| 21.1–22.35 | 4.02–3.99 | m |
| 22.5–22.9 (doublet) | 3.95–3.92 | m |
| 23.15–23.35 | 3.84–3.81 | m–s |

The species SAPO-31 as referred to herein is a silicoaluminophosphate having a three-dimensional microporous crystal framework structure of PO$_2$+, AlO$_2$− and SiO$_2$ tetrahedral units, and whose essential empirical chemical composition on an anhydrous basis is:

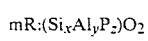
mR:(Si$_x$Al$_y$P$_z$)O$_2$ wherein "R" represents at least one organic templating agent present in the intracrystalline pore system; "m" represents the moles of "R" present per mole of $(Si_xAl_yP_z)O_2$ and has a value of from zero to 0.3, "y" and "z" represent, respectively, the mole fractions of silicon, aluminum and phosphorus present in the oxide moiety, said mole fractions being within the compositional area bounded by points A, B, C, D and E on the ternary diagram which is FIG. 5 of the patent, and preferably within the area bounded by points a, b, c, d and e on the ternary diagram which is FIG. 6 of the patent, said silicoaluminophosphate having a characteristic X ray powder diffraction pattern which contains at least the d spacings set forth below:

| SAPO-31 | | |
|---|---|---|
| 2θ | d(Å) | Relative Intensity |
| 8.5–8.6 | 10.40–10.28 | m–s |
| 20.2–20.3 | 4.40–4.37 | m |
| 21.9–22.1 | 4.06–4.02 | w–m |
| 22.6–22.7 | 3.93–3.92 | vs |
| 31.7–31.8 | 2.823–2.814 | w–m |

The species SAPO-40 as referred to herein is a silicoaluminophosphate material having a three dimensional microporous crystal framework structure of $PO_2^+$, $AlO_2^-$ and $SiO_2$ tetrahedral units, and whose essential empirical chemical composition on an anhydrous basis is:

$$mR:(Si_xAl_yP_x)O_2$$

wherein "R" represenrs at least one organic templating agent present in the intracrystalline pore system; "m" represents the moles of "R" present per mole of $(Si_xAl_yP_z)O_2$ and has a value of from zero to 0.3, "x", "y" and "z" represent respectively, the mole fractions of silicon, aluminum and phosphorus present in the oxide moiety, said mole fractions being within the compositional area bounded by points A, B, C, D and E on the ternary diagram which is FIG. 5 of the patent, or preferably within the area bounded by points a, b, c, d and e on the ternary diagram which is FIG. 6 of the patent, said silicoaluminophosphate having a characteristic X ray powder diffraction pattern which contains at least the d spacings set forth below:

| SAPO-40 | | |
|---|---|---|
| 2θ | d(Å) | Relative Intensity |
| 7.5–7.7 | 11.79–11.48 | vw–m |
| 8.0–8.1 | 11.05–10.94 | s–vs |
| 12.4–12.5 | 7.14–7.08 | w–vs |
| 13.6–13.8 | 6.51–6.42 | m–s |
| 14.0–14.1 | 6.33–6.28 | w–m |
| 27.8–28.0 | 3.209–3.18 | w–m |

The species SAPO-41 as referred to herein is a silicoaluminophosphate having a three dimensional microporous crystal framework structure of $PO_2^+$, $AlO_2^-$ and $SiO_2$ tetrahedral units, and whose essential empirical chemical composition on an anhydrous basis is:

$$mR:(Si_xAl_yP_z)O_2$$

wherein "R" represents at least one organic templating agent present in the intracrystalline pore system; "m" represents the moles of "R" present per mole of $(Si_xAl_yP_z)O_2$ and has a value of from zero to 0.3, "x", "y" and "z" represent, respectively, the mole fractions of silicon, aluminum and phosphorus present in the oxide moiety, said mole fractions being within the compositional area bounded by points A, B, C, D and E on the ternary diagram which is FIG. 5 of the patent, or preferably within the area bounded by points a, b, c, d and e on the ternary diagram which is FIG. 6 of the patent, said silicoaluminophosphate having a characteristic X-ray powder diffraction pattern which contains at least the d-spacings set forth below:

| SAPO-41 | | |
|---|---|---|
| 2θ | d(Å) | Relative Intensity |
| 13.6–13.8 | 6.51–6.42 | w–m |
| 20.5–20.6 | 4.33–4.31 | w–m |
| 21.1–21.3 | 4.21–4.17 | vs |
| 22.1–22.3 | 4.02–3.99 | m–s |
| 22.8–23.0 | 3.90–3.86 | m |
| 23.1–23.4 | 3.82–3.80 | w–m |
| 25.5–25.9 | 3.493–3.44 | w–m |

Large pore(LP)-SAPOs include SAPO-5 and SAPO 37.

The species SAPO-5 as referred to herein is a silicoaluminophosphate material having a three-dimensional microporous crystal framework structure of $PO_2^+$, $AlO_2^-$ and $SiO_2$ tetrahedral units, and whose essential empirical chemical composition on an anhydrous basis is:

$$mR:(Si_xAl_yP_z)O_2$$

wherein "R" represents at least one organic templating agent present in the intracrystalline pore system; "m" represents the moles of "R" present per mole of $(Si_xAl_yP_z)O_2$ and has a value of from zero to 0.3, , "y" and "z" represent respectively, the mole fractions of silicon, aluminum and phosphorus present in the oxide moiety, said mole fractions being within the compositional area bounded by points A, B, C, D and E on the ternary diagram which is FIG. 5 of the patent, or preferably within the area bounded by points a, b, c, d and e on the ternary diagram which is FIG. 6 of the patent, said silicoaluminophosphate having a characteristic X-ray powder diffraction pattern which contains at least the d-spacings set forth below:

| SAPO-5 | | |
|---|---|---|
| 2θ | d(Å) | Relative Intensity |
| 13.6–13.8 | 6.51–6.42 | w–m |
| 7.35–7.65 | 11.79–11.48 | vw–m |
| 19.6–19.95 | 11.05–10.94 | s–vs |
| 20.9–21.3 | 7.14–7.08 | w–vs |
| 22.3–22.6 | 6.51–6.42 | m–s |
| 25.85–26.15 | 3.46–3.40 | w–m |
| 27.8–28.0 | 3.209–3.18 | w–m |

The species SAPO-37 as referred to herein is a silicoaluminophosphate having a microporous crystalline framework structure and whose essential empirical chemical composition in the as-synthesized form and on an anhydrous basis is:

$$mR:(Si_xAl_yP_z)O_2$$

wherein "R" represents at least one organic templating agent present in the intracrystalline pore system; "m" has a value of from 0.02 to 0.3, "x","y" and "z" represent respectively, the mole fractions of silicon, aluminum and phosphorus present in the oxide moiety, said mole fractions being within the compositional area bounded by points A, B, C, D and E on the ternary diagram which is FIG. 5 of the patent, or preferably within the area bounded by points a, b, c, d and e on the ternary diagram which is FIG. 6 of the patent, said silicoaluminophosphate having a characteristic X-ray powder diffraction pattern which contains at least the d-spacings set forth below:

| SAPO-37 | | |
|---|---|---|
| 2θ | d(Å) | Relative Intensity |
| 13.6–13.8 | 6.51–6.42 | w–m |
| 6.1–6.3 | 14.49–14.03 | vs |
| 15.5–15.7 | 5.72–5.64 | w–m |
| 18.5–18.8 | 4.80–4.72 | w–m |
| 23.5–23.7 | 3.79–3.75 | w–m |
| 26.9–27.1 | 3.31–3.29 | w–m |

The adsorption characterization of the NZMSs employed in this invention relates to a characterization that is carried out on a NZMS which has been subjected to a post synthesis treatment, e.g., calcination or chemical treatment, to remove a substantial portion of the template "R" which is present as a result of synthesis. Although a particular NZMS is characterized herein by reference to its adsorption of isobutane as being to the adsorption characteristics of the NZMS in its calcined form, this invention necessarily includes the use of a non-calcined or modified NZMSs which may be characterized by such adsorption in its calcined form, since upon use of such a non-calcined NZMS in the instant process at effective isomerization process conditions the NZMS may be calcined or hydrothermally treated in situ so as to have the characteristic adsorption of isobutane. Thus, the NZMS may be rendered in situ to a form characterized by the aforementioned adsorption characteristics. For example, an as-synthesized MgAPO-11 or MgAPSO-11 may not be characterized by the aforementioned adsorption of isobutane due to the presence of template "R" which is present as a result of synthesis, although the calcined form of MgAPO-11 and MgAPSO-11 will be characterized by the aforementioned adsorption of isobutane. Thus, reference to a NZMS having a particular adsorption characteristic in its calcined or anhydrous form is not intended to exclude the use of the NZMS in its as-synthesized form which upon in situ calcination, hydrothermal treatment and/or other treatment, e.g., ion exchange with suitable atoms, would have such adsorption characteristics.

The following Examples are provided to further illustrate the process of the present invention, but are not limitative thereof. The non zeolitic molecular sieve catalysts used in the following Examples were calcined in air following synthesis to remove the organic templating agent. Unless otherwise specified, all parts, proportions etc. are by weight.

EXAMPLE 1

This experiment illustrates the use of SAPO-34 as a non zeolitic molecular sieve catalyst in the process of this invention. SAPO-34 was prepared as described hereinabove and then heated for one hour under nitrogen at a temperature of 400° C. prior to use. SAPO-34 has a characteristic X-ray powder diffraction pattern which contains at least the d-spacings set forth below:

| SAPO-34 | | |
|---|---|---|
| 2θ | d(Å) | Relative Intensity |
| 9.45–9.65 | 9.36–9.17 | s–vs |
| 10.0–16.2 | 5.54–5.47 | w–m |
| 17.85–18.15 | 4.97–4.89 | w–s |
| 20.55–20.9 | 4.32–4.25 | m–vs |
| 24.95–25.4 | 3.57–3.51 | w–s |
| 30.5–30.7 | 2.931–2.912 | w–s |

This experiment was conducted using a reactor consisting of an 8 inch length by 0.25 inch diameter stainless steel tube. Approximately 0.5 rams of the SAPO-34 catalyst as a powder was dispersed among about 2.5 grams of 20-30 U.S. mesh quartz chips. This mixture was charged to the reactor and the reactor was then immersed in a sand bath and heated to a temperature of 400° C. Connected to the inlet of the reactor was a source of ammonia which was fed at a rate of 15 cubic centimeters/minute in the gas phase at about atmospheric pressure. Also connected to the inlet of the reactor was a liquid feed line of methanol connected to a high pressure liquid chromatography (HPLC) type solvent pump. The methanol was fed as a liquid at a rate of 1.6 milliliters/hour. The methanol:ammonia (C:N) mole ratio was 1.0 and the weight hourly space velocity of methanol was 2.8. The liquid products of the reaction were collected immediately downstream from the reactor in a cold trap at a temperature of 0° C. and the gaseous products were sampled directly to a gas chromatograph. The material collected in the cold trap and the gaseous products were analyzed by gas chromatography on a 10 foot length by ⅛ inch diameter column containing 4% Carbowax ® 20M+0.6% KOH on Carbopack B (Supelco). Analysis of the products of the reaction (samples taken from 3 to 4 hours into the run) showed a 50% methanol conversion, a 29% yield of dimethylether and a methylamine distribution as follows: monomethylamine 41%, dimethylamine 17% and trimethylamine 42%.

EXAMPLE 2

This experiment illustrates the use of SAPO-11 as a non zeolitic molecular sieve catalyst in the process of this invention. SAPO-11 was prepared as described hereinabove and then heated for one hour under nitrogen at a temperature of 400° C. prior to use. SAPO-11 has a characteristic X-ray powder diffraction pattern which contains at least the d-spacings set forth below:

| SAPO-11 | | |
|---|---|---|
| 2θ | d(Å) | Relative Intensity |
| 9.4–9.65 | 9.41–9.17 | m |
| 20.3–20.6 | 4.37–4.31 | m |
| 21.0–21.3 | 4.23–4.17 | vs |
| 21.1–22.35 | 4.02–3.99 | m |
| 22.5–22.9 (doublet) | 3.95–3.92 | m |
| 23.15–23.35 | 3.84–3.81 | m–s |

This experiment was conducted using a reactor consisting of an 8 inch length by 0.25 inch diameter stainless steel tube. Approximately 0.5 grams of the SAPO-11 catalyst as a powder was dispersed among about 2.5 grams of 20–30 U.S. mesh quartz chips. This mixture was charged to the reactor and the reactor was then immersed in a sand bath and heated to a temperature of 400° C. Connected to the inlet of the reactor was a source of ammonia which was fed at a rate of 15 cubic centimeters/minute in the gas phase at about atmospheric pressure. Also connected to the inlet of the reactor was a liquid feed line of methanol connected to a high pressure liquid chromatography (HPLC) type solvent pump. The methanol was fed as a liquid at a rate of 1.6 milliliters/hour. The methanol:ammonia (C:N) mole ratio was 1.0 and the weight hourly space velocity of methanol was 2.8. The liquid products of the reaction were collected immediately downstream from the reactor in a cold trap at a temperature of 0° C. and the gaseous products were sampled directly to a gas chromatograph. The material collected in the cold trap and the gaseous products were analyzed by gas chromatography on a 10 foot length by ⅛ inch diameter column containing 4% Carbowax ® 20M + 0.6% KOH on Carbopack B (Supelco). Analysis of the products of the reaction (samples taken from 3 to 4 hours into the run) showed a 50% methanol conversion, a 27% yield of dimethylether and a methylamine distribution as follows: monomethylamine 32%, dimethylamine 17% and trimethylamine 51%.

EXAMPLE 3

This experiment illustrates the use of SAPO-34 as a non zeolitic molecular sieve catalyst in the process of this invention. SAPO-34 was prepared as described hereinabove and then heated for one hour under nitrogen at a temperature of 400° C. prior to use. SAPO-34 has a characteristic X-ray powder diffraction pattern which contains at least the d-spacings set forth in Example 1.

This experiment was conducted using a reactor consisting of an 8 inch length by 0.25 inch diameter stainless steel tube. Approximately 0.5 grams of the SAPO-34 catalyst as a powder was dispersed among about 2.5 grams of 20–30 U.S. mesh quartz chips. This mixture was charged to the reactor and the reactor was then immersed in a sand bath and heated to a temperature of 400° C. Connected to the inlet of the reactor was a source of ammonia which was fed at a rate of 30 cubic centimeters/minute in the gas phase at about atmospheric pressure. Also connected to the inlet of the reactor was a liquid feed line of methanol connected to a high pressure liquid chromatography (HPLC) type solvent pump. The methanol was fed as a liquid at a rate of 1.6 milliliters/hour. The methanol:ammonia (C:N) mole ratio was 0.5 and the weight hourly space velocity of methanol was 2.8. The liquid products of the reaction were collected immediately downstream from the reactor in a cold trap at a temperature of 0° C. and the gaseous products were sampled directly to a gas chromatograph. The material collected in the cold chromatography on a 10 foot length by ⅛ inch diameter column containing 4% Carbowax ® 20M + 0.6% KOH on Carbopack B (Supelco). Analysis of the products of the reaction (samples taken 4.5 hours into the run) showed a 47% methanol conversion, a 20% yield of dimethylether and a methylamine distribution as follows: monomethylamine 58%, dimethylamine 21% and trimethylamine 21%.

EXAMPLE 4

This experiment illustrates the use of SAPO-34 as a non zeolitic molecular sieve catalyst in the process of this invention. SAPO-34 was prepared as described hereinabove and then heated for one hour under nitrogen at a temperature of 325° C. prior to use. SAPO-34 has a characteristic X-ray powder diffraction pattern which contains at least the d-spacings set forth in Example 1.

This experiment was conducted using a reactor consisting of an 8 inch length by ⅜ inch diameter stainless steel tube encased in a 1 inch diameter stainless steel sheath. Approximately 1.5 grams of the SAPO-34 catalyst as a powder was dispersed among about 4.5 grams of 20–30 U.S. mesh quartz chips. This mixture was charged to the reactor and the reactor was then heated to a temperature of 325° C. with a split furnace heater. Connected to the inlet of the reactor was a source of ammonia which was fed at a rate of 18 cubic centimeters/minute in the gas phase at about atmospheric pressure. Also connected to the inlet of the reactor was a liquid feed line of methanol connected to a high pressure liquid chromatography (HPLC) type solvent pump. The methanol was fed as a liquid at a rate of 1.8 milliliters/hour. The methanol:ammonia (C:N) mole ratio was 1.0 and the weight hourly space velocity of methanol was 1.0. The liquid products of the reaction were collected immediately downstream from the reactor in a cold trap at a temperature of 0° C. and the gaseous products were sampled directly to a gas chromatograph. Gas chromatography analysis of the reactor off gas downstream from the cold trap indicated that virtually all the products of the reaction and the unreacted methanol were collected in the cold trap. The material collected in the cold trap was analyzed by gas chromatography on a 10 foot length by ⅛ inch diameter column containing 4% Carbowax ® 20M + 0.6% KOH on Carbopack B (Supelco). Analysis of the products of the reaction (samples taken 3 hours into the run) showed a 65% methanol conversion, a 13% yield of dimethylether and a methylamine distribution as follows: monomethylamine 63%, dimethylamine 32% and trimethylamine 5%.

EXAMPLE 5

This experiment illustrates the use of SAPO-11 as a non zeolitic molecular sieve catalyst in the process of this invention. SAPO-11 was prepared as described hereinabove and then heated for one hour under nitrogen at a temperature of 400° C. prior to use. SAPO-11 has a characteristic X-ray powder diffraction pattern which contains at least the d spacings set forth in Example 2.

This experiment was conducted using a reactor consisting of an 8 inch length by 0.25 inch diameter stainless steel tube. Approximately 0.5 grams of the SAPO-11 catalyst as a powder was dispersed among about 2.5 grams of 20–30 U.S. mesh quartz chips. This mixture was charged to the reactor and the reactor was then immersed in a sand bath and heated to a temperature of 400° C. Connected to the inlet of the reactor was a source of ammonia which was fed at a rate of 15 cubic centimeters/minute in the gas phase at about atmospheric pressure. Also connected to the inlet of the reactor was a liquid feed line of ethanol connected to a high pressure liquid chromatography (HPLC) type solvent pump. The ethanol was fed as a liquid at a rate of 1.6 milliliters/hour. The liquid products of the reaction were collected immediately downstream from the reactor in a cold trap at a temperature of 0° C. and the gaseous products were sampled directly to a gas chromatograph. Gas chromatography analysis of the reactor off gas downstream from the cold trap indicated that virtually all the products of the reaction and the unreacted methonal were collected in the cold trap. The material collected in the cold trap was analyzed by gas chromatography on a 10 foot length by  inch diameter column containing 4% Carbowax ® 20M+0.6% KOH on Carbopack B (Supelco). Analysis of the products of the reaction showed that monoethylamine was formed.

Although the invention has been illustrated by the preceding examples, it is not to be construed as being limited thereby; but rather, the invention encompasses the generic area as hereinbefore disclosed. Various modifications and embodiments can be made without departing from the spirit and scope thereof.

We claim:

1. A process for preparing an alkylamine which comprises contacting an alcohol with at least one compound having the formula:

$$N-(R')_3$$

wherein each R' group is a member selected from hydrogen or an alkyl radical containing from 1 to 12 carbon atoms, each of said R' groups being the same or different from other R' groups in the said compound, with a non-zeolitic molecular sieve under conditions effective to produce the alkylamine.

2. A process according to claim 1 wherein the alcohol contains from about 1 to about 6 carbon atoms.

3. A process according to claim 2 wherein the alcohol is methanol and the alkylamine is a mixture of monomethylamine, dimethylamine and trimethylamine.

4. A process according to claim 1 wherein the non zeolitic molecular sieve has, in its calcined form, an adsorption of isobutane of less than about 2 percent by weight of the non zeolitic molecular sieve at a partial pressure of 500 torr and a temperature of 20° C.

5. A process according to claim 1 wherein the non zeolitic molecular sieve has, in its calcined form, an adsorption of isobutane of at least about 2 percent by weight and an adsorption of triethylamine of less than 5 percent by weight of the non zeolitic molecular sieve at a partial pressure of 2.6 torr and a temperature of 22° C.

6. A process according to claim 1 wherein the non zeolitic molecular sieve has, in its calcined form, an adsorption of isobutane of at least about 2 percent by weight and an adsorption of triethylamine of at least 5 percent by weight of the non zeolitic molecular sieve at a partial pressure of 2.6 torr and a temperature of 22° C.

7. A process according to claim 1 wherein the non-zeolitic molecular sieve comprises a silicoaluminophosphate (SAPO) molecular sieve.

8. A process according to claim 7 wherein the silicoaluminophosphate molecular sieve comprises any one or more of SAPO-5, SAPO-11, SAPO-31, SAPO-34 and SAPO-41.

9. A process according to claim 8 wherein the silicoaluminophosphate molecular seive comprises SAPO-11.

10. A process according to claim 8 wherein the silicoaluminophosphate molecular seive comprises SAPO-34.

11. A process according to claim 1 wherein the non-zeolitic molecular sieve has a three-dimensional microporous framework structure containing tetrahedral oxide units of silicon, aluminum, phosphorus and at least one element selected from the group consisting of arsenic, beryllium, boron, chromium, cobalt, gallium, germanium, iron, lithium, magnesium, manganese, titanium and zinc.

12. A process according to claim 11 wherein the non-zeolitic molecular sieve has three-dimensional microporous framework structures of $TiO_2$, $AlO_2$, $PO_2$ and $SiO_2$ tetrahedral units having an empirical chemical composition on an anhydrous basis expressed by the formula:

$$mR : (Ti_w Al_x P_y Si_z)O_2$$

wherein "R" represents at least one organic templating agent present in the intracrystalline pore system; "m" represents the molar amount of "R" present per mole of $(Ti_w Al_x P_y Si_z)O_2$ and has a value of zero to about 0.3; and "w", "x", "y" and "z" represent the mole fractions of titanium, aluminum, phosphorus and silicon, respectively, present as tetrahedral oxides and each have a value of at least 0.01, the mole fractions "w", "x", "y" and "z" being such that they are within the pentagonal compositional area defined by points A, B, C, D and E, said points A, B, C, D and E representing the following values for "w", "x", "y" and "z":

| Point | Mole Fraction | | |
| --- | --- | --- | --- |
| | x | y | (z + w) |
| A | 0.60 | 0.38 | 0.02 |
| B | 0.38 | 0.60 | 0.02 |
| C | 0.01 | 0.60 | 0.39 |
| D | 0.01 | 0.01 | 0.98 |
| E | 0.60 | 0.01 | 0.39 |

13. A process acoording to claim 12 wherein the non-zeolitic molecular sieve comprises TiAPSO-5.

14. A process according to claim 11 wherein the non-zeolitic molecular sieve has three-dimensional microporous framework structures of $MgO_2$, $AlO_2$, $PO_2$ and $SiO_2$ tetrahedral units having an empirical chemical composition on an anhydrous basis expressed by the formula:

$$mR : (Mg_w Al_x P_y Si_z)O_2$$

wherein "R" represents at least one organic templating agent present in the intracrystalline pore system; "m" represents the molar amount of "R" present per mole of $(Mg_w Al_x P_y Si_z)O_2$ and has a value of zero to about 0.3; and "w", "x", "y" and "z" represent the mole fractions of magnesium, aluminum, phosphorus and silicon, respectively, present as tetrahedral oxides and each have a value of at least 0.01, the mole fractions "w", "x", "y" and "z" being such that they are within the pentagonal compositional area defined by points A, B, C, D and E, said points A, B, C, D and E representing the following values for "w", "x", "y" and "z":

| Point | Mole Fraction | | |
|---|---|---|---|
| | x | y | (z + w) |
| A | 0.60 | 0.38 | 0.02 |
| B | 0.39 | 0.59 | 0.02 |
| C | 0.01 | 0.60 | 0.39 |
| D | 0.01 | 0.01 | 0.98 |
| E | 0.60 | 0.01 | 0.39 |

15. A process according to claim 14 wherein the non-zeolitic molecular sieve comprises MgAPSO-5 or MgAPSO-36.

16. A process according to claim 11 wherein the non-zeolitic molecular sieve has three-dimensional microporous framework structures of $MnO_2$, $AlO_2$, $PO_2$ and $SiO_2$ tetrahedral units having an empirical chemical composition on an anhydrous basis expressed by the formula:

$$mR : (Mn_wAl_xP_ySi_z)O_2$$

wherein "R" represents at least one organic templating agent present in the intracrystalline pore system; "m" represents the molar amount of "R" present per mole of $(MnAl_xP_ySi_z)O_2$ and has a value of zero to abou 0.3; and "w", "x", "y" and "z" represent the mole fractions of manganese, aluminum, phosphorus and silicon, respectively, present as tetrahedral oxides and each have a value of at least 0.01, the mole fractions "w", "x", "y" and "z" being such that they are within the pentagonal compositional area defined by points A, B, C, D and E, said points A, B, C, D and E representing the following values for "w", "x", "y" and "z":

| Point | Mole Fraction | | |
|---|---|---|---|
| | x | y | (z + w) |
| A | 0.60 | 0.38 | 0.02 |
| B | 0.38 | 0.60 | 0.02 |
| C | 0.01 | 0.60 | 0.39 |
| D | 0.01 | 0.01 | 0.98 |
| E | 0.60 | 0.01 | 0.39 |

17. A process according to claim 16 wherein the non-zeolitic molecular sieve comprises MnAPSO-11 or MnAPSO-31.

18. A process according to claim 11 wherein the non-zeolitic molecular sieve has three-dimensional microporous framework structures of $CoO_2$, $AlO_2$, $PO_2$ and $SiO_2$ tetrahedral units having an empirical chemical composition on an anhydrous basis expressed by the formula:

$$mR : (Co_wAl_xP_ySi_z)O_2$$

wherein "R" represents at least one organic templating agent present in the intracrystalline pore system; "m" represents the molar amount of "R" present per mole of $(Co_wAl_xP_ySi_z)O_2$ and has a value of zero to about 0.3; and "w", "x", "y" and "z" represent the mole fractions of cobalt, aluminum, phosphorus and silicon, respectively, present as tetrahedral oxides and each have a value of at least 0.01, the mole fractions "w", "x", "y" and "z" being such that they are within the pentagonal compositional area defined by points A, B, C, D and E, said points A, B, C, D and E representing the following values for "w", "x", "y" and "z":

| Point | Mole Fraction | | |
|---|---|---|---|
| | x | y | (z + w) |
| A | 0.60 | 0.38 | 0.02 |
| B | 0.38 | 0.60 | 0.02 |
| C | 0.01 | 0.60 | 0.39 |
| D | 0.01 | 0.01 | 0.98 |
| E | 0.60 | 0.01 | 0.39 |

19. A process according to claim 18 wherein the non-zeolitic molecular sieve comprises CoAPSO-11 or CoAPSO-31.

20. A process according to claim 11 wherein the non-zeolitic molecular sieve has three-dimensional microporous framework structures of $ZnO_2$, $AlO_2$, $PO_2$ and $SiO_2$ tetrahedral unit having an empirical chemical composition on an anhydrous basis expressed by the formula:

$$mR : (Zn_wAl_xP_ySi_z)O_2$$

wherein "R" represents at least one organic templating agent present in the intracrystalline pore system; "m" represents the molar amount of "R" present per mole of $(Zn_wAl_xP_ySi_z)O_2$ and has a value of zero to about 0.3; and "w", "x", "y" and "z" represent the mole fractions of zinc, aluminum, phosphorus and silicon, respectively, present as tetrahedral oxides and each have a value of at least 0.01, the mole fractions "w", "x", "y" and "z" being such that they are within the pentagonal compositional area defined by points A, B, C, D and E, said points A, B, C, D and E representing the following values for "w", "x", "y" and "z":

| Point | Mole Fraction | | |
|---|---|---|---|
| | x | y | (z + w) |
| A | 0.60 | 0.38 | 0.02 |
| B | 0.38 | 0.60 | 0.02 |
| C | 0.01 | 0.60 | 0.39 |
| D | 0.01 | 0.01 | 0.98 |
| E | 0.60 | 0.01 | 0.39 |

21. A process according to claim 20 wherein the non-zeolitic molecular sieve comprises ZnAPSO-5.

22. A process according to claim 11 wherein the non-zeolitic molecular sieve has three-dimensional microporous framework structures of $FeO_2$, $AlO_2$, $PO_2$ and $SiO_2$ tetrahedral units having an empirical chemical composition on an anhydrous basis expressed by the formula:

$$mR : (Fe_wAl_xP_ySi_z)O_2$$

wherein "R" represents at least one organic templating agent present in the intracrystalline pore system; "m" represents the molar amount of "R" present per mole of $(Fe_wAl_xP_ySi_z)O_2$ and has a value of zero to about 0.3; and "w", "x", "y" and "z" represent the mole fractions of iron, aluminum, phosphorus and silicon, respectively, present as tetrahedral oxides and each have a value of at least 0.01, the mole fractions "w", "x", "y" and "z" being such that they are within the pentagonal compositional area defined by points A, B, C, D and E, said points A, B, C, D and E representing the following values for "w", "x", "y" and "z":

| Point | Mole Fraction | | |
|---|---|---|---|
| | x | y | (z + w) |
| A | 0.60 | 0.38 | 0.02 |
| B | 0.38 | 0.60 | 0.02 |
| C | 0.01 | 0.60 | 0.39 |
| D | 0.01 | 0.01 | 0.98 |
| E | 0.60 | 0.01 | 0.39 |

23. A process according to claim 22 wherein the non-zeolitic molecular sieve comprises FeAPSO-11.

24. A process according to claim 11 wherein the non-zeolitic molecular sieve has three-dimensional microporous framework structures of $CoO_2$, $MnO_2$, $AlO_2$, $PO_2$ and $SiO_2$ tetrahedral units having an empirical chemical composition on an anhydrous basis expressed by the formula:

$$mR : (Co_uMn_vAl_xP_ySi_z)O_2$$

wherein "R" represents at least one organic templating agent present in the intracrystalline pore system; "m" represents the molar amount of "R" present per mole of $(Co_uMn_vAl_xP_ySi_z)O_2$ and has a value of zero to about 0.3; and "u", "v", "x", "y" and "z" represent the mole fractions of cobalt, manganese, aluminum, phosphorus and silicon, respectively, present as tetrahedral oxides and each have a value of at least 0.01, the mole fractions "u", "v", "x", "y" and "z" being such that they are within the pentagonal compositional area defined by points A, B, C, D and E, said points A, B, C, D and E representing the following values for "w", "x", "y" and "z" (where $w = u + v$):

| Point | Mole Fraction | | |
|---|---|---|---|
| | x | y | (z + w) |
| A | 0.60 | 0.37 | 0.03 |
| B | 0.37 | 0.60 | 0.03 |
| C | 0.01 | 0.60 | 0.39 |
| D | 0.01 | 0.01 | 0.98 |
| E | 0.60 | 0.01 | 0.39 |

25. A process according to claim 11 wherein the non-zeolitic molecular sieve has three-dimensional microporous framework structures of $CoO_2$, $MnO_2$, $MgO_2$, $AlO_2$, $PO_2$ and $SiO_2$ tetrahedral units having an empirical chemical composition on an anhydrous basis expressed by the formula:

$$mR : (Co_tMn_uMg_vAl_xP_ySi_z)O_2$$

wherein "R" represents at least one organic templating agent present in the intracrystalline pore system; "m" represents the molar amount of "R" present per mole of $(Co_tMn_uMg_vAl_xP_ySi_z)O_2$ and has a value of zero to about 0.3; and "t", "u", "v", "x", "y" and "z" represent the mole fractions of cobalt, manganese, magnesium, aluminum, phosphorus and silicon, respectively, present as tetrahedral oxides and each have a value of at least 0.01, the mole fractions "w", "x", "y" and "z" being such that they are within the pentagonal compositional area defined by points A, B, C, D and E, said points A, B, C, D and E representing the following values for "w", "x", "y" and "z" (where $w = t + u + v$):

| Point | Mole Fraction | | |
|---|---|---|---|
| | x | y | (z + w) |
| A | 0.60 | 0.36 | 0.04 |
| B | 0.36 | 0.60 | 0.04 |
| C | 0.01 | 0.60 | 0.39 |
| D | 0.01 | 0.01 | 0.98 |
| E | 0.60 | 0.01 | 0.39 |

26. A process according to claim 11 wherein the non-zeolitic molecular sieve has three-dimensional microporous framework structures of $AsO_2$, $AlO_2$, $PO_2$ and $SiO_2$ tetrahedral units having an empirical chemical composition on an anhydrous basis expressed by the formula:

$$mR : (As_wAl_xP_ySi_z)O_2$$

wherein "R" represents at least one organic templating agent present in the intracrystalline pore system; "m" represents the molar amount of "R" present per mole of $(As_wAl_xP_ySi_z)O_2$ and has a value of zero to about 0.3; and "w", "x", "y" and "z" represent the mole fractions of arsenic, aluminum, phosphorus and silicon, respectively, present as tetrahedral oxides and each have a value of at least 0.01, the mole fractions "w", "x", "y" and "z" being such that they are within the pentagonal compositional area defined by points A, B, C, D and E, said points A, B, C, D and E representing the following values for "w", "x", "y" and "z":

| Point | Mole Fraction | | |
|---|---|---|---|
| | x | y | (z + w) |
| A | 0.60 | 0.38 | 0.02 |
| B | 0.38 | 0.60 | 0.02 |
| C | 0.01 | 0.60 | 0.39 |
| D | 0.01 | 0.01 | 0.98 |
| E | 0.60 | 0.01 | 0.39 |

27. A process according to claim 11 wherein the non-zeolitic molecular sieve has three-dimensional microporous framework structures of $BO_2$, $AlO_2$, $PO_2$ and $SiO_2$ tetrahedral units having an empirical chemical composition on an anhydrous basis expressed by the formula:

$$mR : (B_wAl_xP_ySi_z)O_2$$

wherein "R" represents at least one organic templating agent present in the intracrystalline pore system; "m" represents the molar amount of "R" present per mole of $(B_wAl_xP_ySi_z)O_2$ and has a value of zero to about 0.3; and "w", "x", "y" and "z" represent the mole fractions of boron, aluminum, phosphorus and silicon, respectively, present as tetrahedral oxides and each have a value of at least 0.01, the mole fractions "w", "x", "y" and "z" being such that they are within the pentagonal compositional area defined by points A, B, C, D and E, said points A, B, C, D and E representing the following values for "w", "x", "y" and "z":

| Point | Mole Fraction | | |
|---|---|---|---|
| | x | y | (z + w) |
| A | 0.60 | 0.38 | 0.02 |
| B | 0.38 | 0.60 | 0.02 |
| C | 0.01 | 0.60 | 0.39 |
| D | 0.01 | 0.01 | 0.98 |

| | Mole Fraction | | |
|---|---|---|---|
| Point | x | y | (z + w) |
| E | 0.60 | 0.01 | 0.39. |

28. A process according to claim 27 wherein the non-zeolitic molecular sieve comprises BAPSO-35.

29. A process according to claim 11 wherein the non-zeolitic molecular sieve has three-dimensional microporous framework structures of $BeO_2$, $AlO_2$, $PO_2$ and $SiO_2$ tetrahedral units having an empirical chemical composition on an anhydrous basis expressed by the formula:

$$mR : (Be_wAl_xP_ySi_z)O_2$$

wherein "R" represents at least one organic templating agent present in the intracrystalline pore system; "m" represents the molar amount of "R" present per mole of $(Be_wAl_xP_ySi_z)O_2$ and has a value of zero to about 0.3; and "w", "x", "y" and "z" represent the mole fractions of beryllium, aluminum, phosphorus and silicon, respectively, present as tetrahedral oxides and each have a value of at least 0.01, the mole fractions "w", "x", "y" and "z" being such that they are within the pentagonal compositional area defined by points A, B, C, D and E, said points A, B, C, D and E representing the following values for "w", "x", "y" and "z":

| | Mole Fraction | | |
|---|---|---|---|
| Point | x | y | (z + w) |
| A | 0.60 | 0.38 | 0.02 |
| B | 0.38 | 0.60 | 0.02 |
| C | 0.01 | 0.60 | 0.39 |
| D | 0.01 | 0.01 | 0.98 |
| E | 0.60 | 0.01 | 0.39. |

30. A process according to claim 11 wherein the non-zeolitic molecular sieve has three-dimensional microporous framework structures of $CrO_2$, $AlO_2$, $PO_2$ and $SiO_2$ tetrahedral units having an empirical chemical composition on an anhydrous basis expressed by the formula:

$$mR : (Cr_wAl_{xy}P_ySi_z)O_2$$

wherein "R" represents at least one organic templating agent present in the intracrystalline pore system; "m" represents the molar amount of "R" present per mole of $(Cr_wAl_xP_ySi_z)O_2$ and has a value of zero to about 0.3; and "w", "x", "y" and "z" represent the mole fractions of chromium, aluminum, phosphorus and silicon, respectively, present as tetrahedral oxides and each have a value of at least 0.01, the mole fractions "w", "x", "y" and "z" being such that they are within the pentagonal compositional area defined by points A, B, C, D and E, said points A, B, C, D and E representing the following values for "w", "x", "y" and "z":

| | Mole Fraction | | |
|---|---|---|---|
| Point | x | y | (z + w) |
| A | 0.60 | 0.38 | 0.02 |
| B | 0.38 | 0.60 | 0.02 |
| C | 0.01 | 0.60 | 0.39 |
| D | 0.01 | 0.01 | 0.98 |

| | Mole Fraction | | |
|---|---|---|---|
| Point | x | y | (z + w) |
| E | 0.60 | 0.01 | 0.39. |

31. A process according to claim 11 wherein the non-zeolitic molecular sieve has three-dimensional microporous framework structures of $GaO_2$, $AlO_2$, $PO_2$ and $SiO_2$ tetrahedral units having an empirical chemical composition on an anhydrous basis expressed by the formula:

$$mR : (Ga_wAl_xP_ySi_z)O_2$$

wherein "R" represents at least one organic templating agent present in the intracrystalline pore system; "m" represents the molar amount of "R" present per mole of $(Ga_wAl_xP_ySi_z)O_2$ and has a value of zero to about 0.3; and "w", "x", "y" and "z" represent the mole fractions of gallium, aluminum, phosphorus and silicon, respectively, present as tetrahedral oxides and each have a value of at least 0.01, the mole fractions "w", "x", "y" and "z" being such that they are within the pentagonal compositional area define by points A, B, C, D and E, said points A, B, C, D and E representing the following values for "w", "x", "y" and "z":

| | Mole Fraction | | |
|---|---|---|---|
| Point | x | y | (z + w) |
| A | 0.60 | 0.38 | 0.02 |
| B | 0.38 | 0.60 | 0.02 |
| C | 0.01 | 0.60 | 0.39 |
| D | 0.01 | 0.01 | 0.98 |
| E | 0.60 | 0.01 | 0.39. |

32. A process according to claim 11 wherein the non-zeolitic molecular sieve has three-dimensional microporous framework structures of $GeO_2$, $AlO_2$, $PO_2$ and $SiO_2$ tetrahedral units having an empirical chemical composition on an anhydrous basis expressed by the formula:

$$mR : (Ge_wA_xP_ySi_z)O_2$$

wherein "R" represents at least one organic templating agent present in the intracrystalline pore system; "m" represents the molar amount of "R" present per mole of $(Ge_wAl_xP_ySi_z)O_2$ and has a value of zero to abou 0.3; and "w", "x", "y" and "z" represent the mole fractions of germanium, aluminum, phosphorus and silicon, respectively, present as tetrahedral oxides and each have a value of at least 0.01, the mole fractions "w", "x", "y" and "z" being such that they are within the pentagonal compositional area defined by points A, B, C, D and E, said points A, B, C, D and E representing the following values for "w", "x", "y" and "z":

| | Mole Fraction | | |
|---|---|---|---|
| Point | x | y | (z + w) |
| A | 0.60 | 0.38 | 0.02 |
| B | 0.38 | 0.60 | 0.02 |
| C | 0.01 | 0.60 | 0.39 |
| D | 0.01 | 0.01 | 0.98 |
| E | 0.60 | 0.01 | 0.39. |

33. A process according to claim 11 wherein the non-zeolitic molecular sieve has three-dimensional microporous framework structures of $LiO_2$, $AlO_2$, $PO_2$ and $SiO_2$ tetrahedral units having an empirical chemical composition on an anhydrous basis expressed by the formula:

$$mR : (Li_wAl_xP_ySi_z)O_2$$

wherein "R" represents at least one organic templating agent present in the intracrystalline pore system; "m" represents the molar amount of "R" present per mole of $(Li_wAl_{xy}P_ySi_z)O_2$ and has a value of zero to about 0.3; and "w", "x", "y" and "z" represent the mole fractions of lithium, aluminum, phosphorus and silicon, respectively, present as tetrahedral oxides and each have a value of at least 0.01, the mole fractions "w", "x", "y" and "z" being such that they are within the pentagonal compositional area defined by points A, B, C, D and E, said points A, B, C, D and E representing the following values for "w", "x", "y" and "z":

| Point | Mole Fraction | | |
|---|---|---|---|
| | x | y | (z + w) |
| A | 0.60 | 0.38 | 0.02 |
| B | 0.38 | 0.60 | 0.02 |
| C | 0.01 | 0.60 | 0.39 |
| D | 0.01 | 0.01 | 0.98 |
| E | 0.60 | 0.01 | 0.39. |

34. A process according to claim 1 wherein the non-zeolitic molecular sieve comprises an aluminophosphate (AlPO₄) molecular sieve.

35. A process according to claim 34 wherein the aluminophosphate molecular sieve comprises any one or more of AlPO₄-5, AlPO₄-11 and AlPO₄-31.

36. A process according to claim 1 wherein the non-zeolitic molecular sieve comprises a metal aluminophosphate (MeAPO) molecular sieve.

37. A process according to claim 36 wherein the metal aluminophosphate molecular sieve comprises MgAPO-5, MgAPO-11, MnAPO-5, MnAPO-11 or CoAPO-5.

38. A process according to claim 1 wherein the non-zeolitic molecular sieve comprises an iron aluminophosphate (FeAPO) molecular sieve.

39. A process according to claim 38 wherein the iron aluminophosphate molecular sieve comprises FeAPO-11.

40. A process according to claim 1 wherein the non-zeolitic molecular sieve comprises a titanium aluminophosphate (TAPO) molecular sieve.

41. A process according to claim 40 wherein the titanium aluminophosphate molecular sieve comprises TiAPO-11.

42. A process according to claim 1 wherein the non-zeolitic molecular sieve has a three-dimensional microporous framework structure containing tetrahedral oxide units of aluminum, phosphorus and at least one element "M" selected from the group consisting of arsenic, beryllium, boron, chromium, gallium, germanium, lithium and vanadium, subject to the proviso that, when "M" denotes two elements the second element is selected from the group consisting of arsenic, beryllium, boron, chromium, gallium, germanium, lithium, vanadium, cobalt, iron, magnesium, manganese, titanium and zinc.

43. A process according to claim 42 wherein the non-zeolitic molecular sieve has three-dimensional microporous framework structures of $AsO_2$, $AlO_2$ and $PO_2$ tetrahedral units having an empirical chemical composition on an anhydrous basis expressed by the formula:

$$mR : (As_xAl_yP_z)O_2$$

wherein "R" represents at least one organic templating agent present in the intracrystalline pore system; "m" represents the molar amount of "R" present per mole of $(As_xAl_yP_z)O_2$ and has a value of zero to about 0 and "x", "y" and "z" represent the mole fractions of arsenic, aluminum and phosphorus, respectively, present as tetrahedral oxides and each have a value of at least 0.01, the mole fractions "x", "y" and "z" being such that they are within the hexagonal compositional area defined by points A, B, C, D, E and F, said points A, B, C, D, E and F representing the following values for "x", "y" and "z":

| Point | Mole Fraction | | |
|---|---|---|---|
| | x | y | z |
| A | 0.01 | 0.60 | 0.39 |
| B | 0.01 | 0.39 | 0.60 |
| C | 0.39 | 0.01 | 0.60 |
| D | 0.60 | 0.01 | 0.39 |
| E | 0.60 | 0.39 | 0.01 |
| F | 0.39 | 0.60 | 0.01. |

44. A process according to claim 42 wherein the non-zeolitic molecular sieve has three-dimensional microporous framework structures of $BO_2$, $AlO_2$ and $PO_2$ tetrahedral units having an empirical chemical composition on an anhydrous basis expressed by the formula:

$$mR : (B_xAl_yP_z)O_2$$

wherein "R" represents at least one organic templating agent present in the intracrystalline pore system; "m" represents the molar amount of "R" present per mole of $(B_xAl_yP_z)O_2$ and has a value of zero to about 0.3; and "x", "y" and "z" represent the mole fractions of boron, aluminum and phosphorus, respectively, present as tetrahedral oxides and each have a value of at least 0.01, the mole fractions "x", "y" and "z" being such that they are within the pentagonal compositional area defined by points A, B, C, D and E, the points A, B, C, D and E representing the following values for "x", "y" and "z":

| Point | Mole Fraction | | |
|---|---|---|---|
| | x | y | z |
| A | 0.02 | 0.60 | 0.38 |
| B | 0.02 | 0.38 | 0.60 |
| C | 0.39 | 0.01 | 0.60 |
| D | 0.98 | 0.01 | 0.01 |
| E | 0.39 | 0.60 | 0.01. |

45. A process according to claim 42 wherein the non-zeolitic molecular sieve has three-dimensional microporous framework structures of $BeO_2$, $AlO_2$ and $PO_2$ tetrahedral units having an empirical chemical composition on an anhydrous basis expressed by the formula:

mR : (Be$_x$Al$_y$P$_z$)O$_2$ wherein "R" represents at least one organic templating agent present in the intracrystalline pore system; "m" represents the molar amount of "R" present per mole of (Be$_x$Al$_y$P$_z$)O$_2$ and has a value of zero to about and "x", "y" and "z" represent the mole fractions of beryllium, aluminum and phosphorus, respectively, present as tetrahedral oxides and each have a value of at least 0.01, the mole fractions "x", "y" and "z" being such that they are within the hexagonal compositional area defined by points A, B, C, D, E and F, the points A, B, C, D, E and F representing the following values for "x", "y" and "z":

| Point | Mole Fraction | | |
|---|---|---|---|
| | x | y | z |
| A | 0.01 | 0.60 | 0.39 |
| B | 0.01 | 0.39 | 0.60 |
| C | 0.39 | 0.01 | 0.60 |
| D | 0.60 | 0.01 | 0.39 |
| E | 0.60 | 0.39 | 0.01 |
| F | 0.39 | 0.60 | 0.01. |

46. A process according to claim 42 wherein the non-zeolitic molecular sieve has three-dimensional microporous framework structures of CrO$_2$, AlO$_2$ and PO$_2$ tetrahedral units having an empirical chemical composition on an anhydrous basis expressed by the formula:

mR : (Cr$_x$Al$_y$P$_z$)O$_2$ wherein "R" represents at least one organic templating agent present in the intracrystalline pore system; "m" represents the molar amount of "R" present per mole of (Cr$_x$Al$_y$P$_z$)O$_2$ and has a value of zero to about 0.3; and "x", "y" and "z" represent the mole fractions of chromium, aluminum and phosphorus, respectively, present as tetrahedral oxides and each have a value of at least 0.01, the mole fractions "x", "y" and "z" being such that they are within the hexagonal compositional area defined by points A, B, C, D, E and F, the points A, B, C, D, E and F representing the following values for "x", "y" and "z":

| Point | Mole Fraction | | |
|---|---|---|---|
| | x | y | z |
| A | 0.01 | 0.60 | 0.39 |
| B | 0.01 | 0.39 | 0.60 |
| C | 0.39 | 0.01 | 0.60 |
| D | 0.60 | 0.01 | 0.39 |
| E | 0.60 | 0.39 | 0.01 |
| F | 0.39 | 0.60 | 0.01. |

47. A process according to claim 42 wherein the non-zeolitic molecular sieve has three dimensional microporous framework structures of GaO$_2$, AlO$_2$ and PO$_2$ tetrahedral units having an empirical chemical composition on an anhydrous basis expressed by the formula:

mR : (Ga$_x$Al$_y$P$_z$)O$_2$ wherein "R" represents at least one organic templating agent present in the intracrystalline pore system; "m" represents the molar amount of "R" present per mole of (Ga$_x$Al$_y$P$_z$)O$_2$ and has a value of zero to about 0.3; and "x", "y" and "z" represent the mole fractions of gallium, aluminum and phosphorus, respectively, present as tetrahedral oxides and each have a value of at least 0.01, the mole fractions "x", "y" and "z" being such that they are within the hexagonal compositional area defined by points A, B, C, D, E and F, the points A, B, C, D, E and F representing the following values for "x", "y" and "z":

| Point | Mole Fraction | | |
|---|---|---|---|
| | x | y | z |
| A | 0.01 | 0.60 | 0.39 |
| B | 0.01 | 0.34 | 0.65 |
| C | 0.34 | 0.01 | 0.65 |
| D | 0.60 | 0.01 | 0.39 |
| E | 0.60 | 0.39 | 0.01 |
| F | 0.39 | 0.60 | 0.01. |

48. A process according to claim 42 wherein the non-zeolitic molecular sieve has three-dimensional microporous framework structures of GeO$_2$, AlO$_2$ and PO$_2$ tetrahedral units having an empirical chemical composition on an anhydrous basis expressed by the formula:

mR : (Ge$_x$Al$_y$P$_z$)O$_2$ wherein "R" represents at least one organic templating agent present in the intracrystalline pore system; "m" represents the molar amount of "R" present per mole of (Ge$_x$Al$_y$P$_z$)O$_2$ and has a value of zero to about ; and "x", "y" and "z" represent the mole fractions of germanium, aluminum and phosphorus, respectively, present as tetrahedral oxides and each have a value of at least 0.01, the mole fractions "x", "y" and "z" being such that they are within the pentagonal compositional area defined by points A, B, C, D and E, the points A, B, C, D and E representing the following values for "x", "y" and "z":

| Point | Mole Fraction | | |
|---|---|---|---|
| | x | y | z |
| A | 0.01 | 0.60 | 0.39 |
| B | 0.01 | 0.47 | 0.52 |
| C | 0.94 | 0.01 | 0.05 |
| D | 0.98 | 0.01 | 0.01 |
| E | 0.39 | 0.60 | 0.01 |

49. A process according to claim 42 wherein the non-zeolitic molecular sieve has threedimensional microporous framework structures of LiO$_2$, AlO$_2$ and PO$_2$ tetrahedral units having an empirical chemical composition on an anhydrous basis expressed by the formula:

mR : (Li$_x$Al$_y$P$_z$)O$_2$ wherein "R" represents at least one organic templating agent present in the intracrystalline pore system; "m" represents the molar amount of "R" present per mole of (Li$_x$Al$_y$P$_z$)O$_2$ and has a value of zero to about 0.3; and "x", "y" and "z" represent the mole fractions of lithium, aluminum and phosphorus, respectively, present as tetrahedral oxides and each have a value of at least 0.01, the mole fractions "x", "y" and "z" being such that they are within the hexagonal compositional area defined by points A, B, C, D, E and F, the points A, B, C, D, E and F representing the following values for "x", "y" and "z":

| Point | Mole Fraction | | |
|---|---|---|---|
| | x | y | z |
| A | 0.01 | 0.60 | 0.39 |
| B | 0.01 | 0.39 | 0.60 |
| C | 0.39 | 0.01 | 0.60 |
| D | 0.60 | 0.01 | 0.39 |
| E | 0.60 | 0.39 | 0.01 |
| F | 0.39 | 0.60 | 0.01. |

50. A process according to claim 42 wherein the non-zeolitic molecular sieve has three-dimensional microporous framework structures of $MO_2$, $AlO_2$ and $PO_2$ tetrahedral units having an empirical chemical composition on an anhydrous basis expressed by the formula:

$$mR : (M_xAl_yP_z)O_2$$

wherein "R" represenrs at least one organic templating agent present in the intracrystalline pore system; "m" represents the molar amount of "R" present per mole of $(M_xAl_yP_z)O_2$ and has a value of zero to about 0.3; "M" represents at least two elements, one selected from the group consisting of arsenic, beryllium, boron, chromium, gallium, germanium, lithium and vanadium, while the second is selected from the group consisting of cobalt, iron, magnesium, manganese, titanium and zinc; and "x", "y" and "z" represent the mole fractions of "M", aluminum and phosphorus, respectively, present as tetrahedral oxides and are within the pentagonal compositional area defined by points A, B, C, D and E, the points A, B, C, D and E representing the following values for "x", "y" and "z":

| Point | Mole Fraction | | |
|---|---|---|---|
| | x | y | z |
| A | 0.02 | 0.60 | 0.38 |
| B | 0.02 | 0.38 | 0.60 |
| C | 0.39 | 0.01 | 0.60 |
| D | 0.98 | 0.01 | 0.01 |
| E | 0.39 | 0.60 | 0.01. |

51. A process according to claim 42 wherein the non-zeolitic molecular sieve has three dimensional microporous framework structures of $MO_2$, $AlO_2$ and $PO_2$ tetrahedral units having an empirical chemical composition on an anhydrous basis expressed by the formula:

$$mR : (M_xAl_yP_z)O_2$$

wherein "R" represents at least one organic templating agent present in the intracrystalline pore system; "m" represents the molar amount of "R" present per mole of $(M_xAl_yP_z)O_2$ and has a value of zero to about "M" represents at least two elements, $M_1$ and $M_2$, selected from the group consisting of arsenic, beryllium, boron, chromium, gallium, germanium, lithium and vanadium; and "x", "y" and "z" represent the mole fractions of M ($=M_1+M_2$ etc.), aluminum and phosphorus, respectively, present as tetrahedral oxides, said mole fractions being such that they are within the pentagonal compositional area defined by points A, B, C, D and E, the points A, B, C, D and E representing the following values for "x", "y" and "z":

| Point | Mole Fraction | | |
|---|---|---|---|
| | x | y | z |
| A | 0.02 | 0.60 | 0.38 |
| B | 0.02 | 0.38 | 0.60 |
| C | 0.39 | 0.01 | 0.60 |
| D | 0.98 | 0.01 | 0.01 |
| E | 0.39 | 0.60 | 0.01. |

52. A process according to claim 1 which is carried out at a weight hourly space velocity, based on the alcohol, of from about 0.1 to about 50.

53. A process according to claim 52 which is carried out at a weight hourly space velocity, based on the alcohol, of from about 0.5 to about 10.

54. A process according to claim 1 which is carried out at a temperature of about 250° C. to about 500° C.

55. A process according to claim 54 which is carried out at a temperature of about 300° C. to about 450° C.

56. A process according to claim 1 which is carried out at a pressure of from sub-atmospheric to about 1000 psig.

57. A process according to claim 56 which is carried out at a pressure of from about atmospheric to about 500 psig.

58. A process according to claim 56 which is carried out at substantially atmospheric pressure.

59. A process according to claim 1 which is carried out at an alcohol conversion of at least about 10%.

60. A process according to claim 3 which is carried out at a selectivity to monomethylamine of at least about 50%.

61. A process for selectively producing monomethylamine which process comprises contacting methanol and ammonia with a non-zeolitic molecular sieve under conditions effective to selectively produce monomethylamine.

62. A process according to claim 61 which is carried out at a selectivity to monomethylamine of at least about 50%.

* * * * *